(12) United States Patent
Poulsen et al.

(10) Patent No.: US 12,415,789 B2
(45) Date of Patent: Sep. 16, 2025

(54) MACROCYCLES COMPRISING A 4-AMIDO-2,4-PENTADIENOATE MOIETY FOR THE TREATMENT OF HYPOXIC CANCERS

(71) Applicant: Aarhus Universitet, Aarhus C (DK)

(72) Inventors: Thomas Bjørnskov Poulsen, Højbjerg (DK); Per Hjerrild, Aarhus C (DK); Kristian Mark Jacobsen, Harlev J (DK); Thomas Tørring, Højbjerg (DK)

(73) Assignee: Aarhus Universitet, Aarhus C (DK)

( * ) Notice: Subject to any disclaimer, the term of this patent is extended or adjusted under 35 U.S.C. 154(b) by 453 days.

(21) Appl. No.: 17/756,737

(22) PCT Filed: Dec. 4, 2020

(86) PCT No.: PCT/EP2020/084736
§ 371 (c)(1),
(2) Date: Jun. 1, 2022

(87) PCT Pub. No.: WO2021/110968
PCT Pub. Date: Jun. 10, 2021

(65) Prior Publication Data
US 2023/0020952 A1    Jan. 19, 2023

(30) Foreign Application Priority Data
Dec. 4, 2019 (EP) .................................... 19213635

(51) Int. Cl.
| | | |
|---|---|---|
| *C07D 273/00* | (2006.01) | |
| *C07D 413/06* | (2006.01) | |
| *C07D 498/04* | (2006.01) | |

(52) U.S. Cl.
CPC ......... *C07D 273/00* (2013.01); *C07D 413/06* (2013.01); *C07D 498/04* (2013.01)

(58) Field of Classification Search
CPC ... C07D 273/00; C07D 413/06; C07D 498/04
USPC ........................................................ 540/467
See application file for complete search history.

(56) References Cited

FOREIGN PATENT DOCUMENTS

| WO | WO 03/076424 A1 | 9/2003 |
|---|---|---|
| WO | WO 2017/166812 A1 | 10/2017 |

OTHER PUBLICATIONS

Cancer [online], [retrieved on Jul. 6, 2007] Retrieved from the Internet, URL: http://www.nlm.nih.gov/medlineplus/cancer.html (Year: 2007).*

(Continued)

*Primary Examiner* — Kristin A Vajda
(74) *Attorney, Agent, or Firm* — Knobbe Martens Olson & Bear LLP

(57) ABSTRACT

The present disclosure provides macrocyclic compounds comprising a 4-amido-2,4-pentadienoate (APD) moiety. The compounds exhibit toxicity that is selective to the hypoxic micro-environments often found in cancerous tissues. The disclosed compounds are therefore suitable for treatment of hypoxic cancer cells.

20 Claims, 17 Drawing Sheets

(56) References Cited

OTHER PUBLICATIONS

Lala et al., Role of nitric oxide in tumor progression: Lessons from experimental tumors, Cancer and Metastasis Reviews (1998), 17, 91-106 (Year: 1998).*
Golub et al., Molecular Classification of Cancer: Class Discovery and Class Prediction by Gene Expression Monitoring, Science ( 1999), vol. 286, 531-537 (Year: 1999).*
Chen, Jian et al., "Syntheses and anti-pancreatic cancer activities of rakicidin A analogues" European Journal of Medicinal Chemistry, 2018, pp. 601-627, vol. 151.
Emdin, Connor A. et al., "A missense variant in Mitochondrial Amidoxime Reducing Component 1 gene and protection against liver disease" BioRxiv, 2019, https://www.biorxiv.org/content/10.1101/594523v1.
Hu, Jinsong et al., "Targeting the multiple hypoxic niche with TH-302, a hypoxia-activated prodrug" Blood, Sep. 2010, pp. 1524-1527, vol. 116, No. 9.
Jacobsen, Kristian Mark et al., "APD-Containing Cyclolipodepsipeptides Target Mitochondrial Function in Hypoxic Cancer Cells" Cell Chemical Biology, pp. 1337-1349, vol. 25, 2018.
Rixen, Sophia et al., "Mitochondrial amidoxime-reducing component 2 (mARC2) has a significant role in N-reductive activity and energy metabolism" J. Biol. Chem., 2019, pp. 17593-17602, vol. 294.
Rowinsky, Eric K. et al., "Novel Radiation Sensitizers Targeting Tissue Hypoxia" Oncology, Oct. 1999, pp. 61-70, vol. 13, No. 10, Supp No. 5.
Sang, Feng et al., "Structure-Activity Relationship Study of Rakicidins: Overcoming Chronic Myeloid Leukemia Resistance to Imatinib with 4-Methylester-Rakicidin A" Journal of Medicinal Chemistry, 2016, pp. 1184-1196, vol. 59.
Sun, Yuanjun et al., "Syntheses and biological evaluation of BE-43547A2 analogues modified at O35 ester and C15-OH sites" Tetrahedron, 2019, pp. 1808-1818, vol. 75.
Teslovich, Tany M. et al., "Biological, clinical and population relevance of 95 loci for blood lipids" Nature, Aug. 2010, pp. 707-713, vol. 466.
Tsakos, Michail et al., "Total Synthesis and Biological Evaluation of Rakicidin A and Discovery of a Simplified Bioactive Analogue" Angew. Chem. Int. Ed., 2016, pp. 1030-1035, vol. 55.
Villadsen, Nikolaj L. et al., "Synthesis of ent-BE-43547A1 reveals a potent hypoxia-selective anticancer agent and uncovers the biosynthetic origin of the APD-CLD natural products" Nature Chemistry, Mar. 2017, pp. 264-272, vol. 9.
International Preliminary Report on Patentability for PCT/EP2020/084736 dated May 17, 2022.
International Search Report for PCT/EP2020/084736 dated Jan. 26, 2021.

* cited by examiner

A)

B)

A)

B)

A)

B)

A)

B)

MACROCYCLES COMPRISING A 4-AMIDO-2,4-PENTADIENOATE MOIETY FOR THE TREATMENT OF HYPOXIC CANCERS

CROSS REFERENCE TO RELATED APPLICATIONS

This application is a U.S. National Phase Application of PCT International Application Number PCT/EP2020/084736, filed on Dec. 4, 2020, designating the United States of America and published in the English language, which is an International Application of and claims the benefit of priority to European Patent Application No. 19213635.6, filed on Dec. 4, 2019. The disclosures of the above-referenced applications are hereby expressly incorporated by reference in their entireties.

TECHNICAL FIELD OF THE INVENTION

The present invention relates to compounds for treatment of cancer. In particular, the present invention relates to compounds that selectively kill hypoxic cancer cells. Furthermore, the compounds are macrocycles comprising a 4-amido-2,4-pentadienoate (APD) moiety.

BACKGROUND OF THE INVENTION

Cancerous tissues provoke the formation of hypoxic regions resulting from disorganization of vasculature by impeded growth regulation and accelerated oxygen consumption of cancer-associated tissues. Especially solid tumors are known to form hypoxic regions caused by an obstructed supply of oxygen, with the tumor oxygenation being heterogeneously distributed. Hypoxic cancer cells experience minimal oxygenation from aberrant blood flow, which results in transcriptional adaptions of said cells. Significant difficulties in treatment of hypoxic cancer in solid tumors results from a combined effect of aversion from programmed cell death, poor drug delivery due to ineffective arterial blood supply throughout tumor tissues, and hypoxia-induced de-differentiation of cancer cells to a stem-like state further complicating any permanent abolishment of the cancer. Hypoxic cancer is coupled to traits of inefficient radiation therapy, metastatic dissemination, and disease relapse, communally resulting in poor patient prognosis.

Locally advanced solid tumors contain regions of low oxygen pressure (hypoxia), due to inefficient blood supply from functionally abnormal tumor vasculature and the resultant hypoxic cancer cells are often found to be resistant to chemo- and radiotherapy.

In the hostile microenvironment of the hypoxic tumor there is a selective pressure towards high tolerance cells and/or motile cells that can actively escape. Such phenotypic plasticity may be mediated by epithelial-mesenchymal transition (EMT)—a latent developmental transcriptional program that appears to be re-activated in a number of human malignancies and which results in increased resistance to chemotherapy as well as to a motile and invasive phenotype. Recently it was found that Twist, a transcriptional driver of EMT, is directly controlled by HIF-1, thus linking hypoxia to EMT. The effects of hypoxia and EMT may in fact converge upon direct effects on the sub-population of tumor initiating cells that have now been characterized from many cancer subtypes and which are believed to be the cells causative for relapse after initial therapy-induced disease remission. This area is currently seeing intense research effort. Taken together, several lines of evidence indicate that tumor hypoxia is playing a critical role in the events that eventually lead to cancer progression, chemo- and radioresistance, and metastasis and thus that intervention targeted to hypoxic cells may have significant therapeutic potential.

Compounds with the ability to selectively target hypoxic cancer cells are exceedingly rare. Previously, so-called bio-reductively activated cytotoxins, also known as hypoxia-activated prodrugs (HAPs), have been developed in the attempt of obtaining effective and nonviolent methods to safely treat patients with hypoxic tumors. Such compounds, exemplified e.g. by TH302 and tirapazamine, have made it to clinical tests. A limitation of bio-reductively activated cytotoxins, however, is that their activity can vary significantly across different cell lines and that they all rely on an enzymatic mechanism for activation, which could impact the sensitivity of individual cancer cells to the action of compounds. Thus, it is clear that compounds with ability to selectively target hypoxic cells via alternative mechanisms are highly desired. One starting point for such development, is the secondary natural metabolites called the 4-amido-2,4-pentadienoate-cyclolipodepsipeptide (APD-CLD) compounds. The natural compounds comprise the 4-amido-2,4-pentadienoate (APD) electrophilic moiety that appears to mediate their biological activity. Especially, the rakicidins and BE-43547 congeners have been reported to possess cytotoxic activity towards cancer cells cultured under hypoxic conditions. Any drug developed should be well tolerated, highly toxic to the cancer cells, and resistant to hydrolytic degradation.

M. Tsakos et al., Angew. Chem. Int. Ed., 2015, 55, 1030, discloses a synthetic pathway for obtaining compounds derived from rakicidin A, thus comprising the biologically active APD moiety. All the compounds of the prior art document comprise a lactone connection within the macrocyclic backbone, being a common feature of the natural rakicidins. However, the compounds of the present application does not comprise any lactone moiety within the macrocycle in order to increase their resistance towards hydrolytic degradation.

WO03/076424, discloses a generic formula for a range of macrocyclic compounds useful for treatment of e.g. malignancy related disorders. The compounds are related to those of the present application by having a benzene ring within the macrocyclic backbone. However, the compounds in the prior art document are challenged by the fact that they do not comprise the biologically active electrophilic APD moiety.

Thus, the prior art does not provide solutions for the above-mentioned problems in treating hypoxic cancer. An improved hypoxia selective compound comprising the APD-moiety would therefore be advantageous, and in particular a more efficient and stable compound would be advantageous.

SUMMARY OF THE INVENTION

An object of the present application relates to the provision of compounds suitable for treatment of hypoxic cancer cells, especially in solid tumors. The disclosed compounds are analogs of cyclolipodepsipeptides (CLDs) having a macrocyclic backbone comprising a 4-amido-2,4-pentadienoate (APD) moiety. The APD moiety is an electrophilic functionality that is considered to possess the biological activity towards hypoxic cancer cells and which moiety is a known substructure in the naturally occurring APD-CLD class of compounds, such as the Rakicidins.

A particular object of the present application is to provide compounds that solve the problems of safe and efficient treatment of hypoxic cancers. Thus, unlike the naturally occurring cyclolipodepsipeptides, the compounds of the present application do not comprise a lactone moiety in the macrocyclic backbone, which is considered to increase the resistance to hydrolytic degradation. An embodiment of the compounds of the present application may also be viewed as derivatives of the naturally occurring rakicidins, wherein the lactone moiety (—C(O)O—) in the macrocyclic backbone is exchanged with an ether connection (—O—), thus to protect the structure from hydrolysis. The introduced protection is considered to increase the residence time of the drugs within tumor tissue and thus to provide a more effective treatment regime. In addition, a benzene ring has been incorporated into the macrocycles of the present application for further increasing their chemical stability.

Thus, one aspect of the invention of the present application relates to a compound of Formula (1)

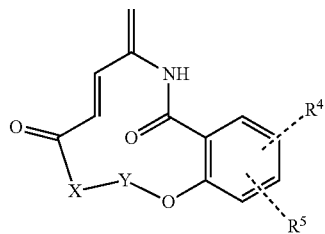

(1)

wherein, X is selected from the group consisting of a bond, or —$NR^{N1}CHR^{1}C(O)$—' for which —' denotes the bond connecting X to Y, Y is selected from the group consisting of —$NR^{N2}CR^{2}R^{2'}CHR^{3}$—*, —$NR^{N2}CR^{2}R^{2'}CHR^{3}CH_{2}$—*, for which —* denotes the bond connecting Y to O, $R^{N1}$ and $R^{N2}$ are each optionally substituted groups independently selected from the group consisting of hydrogen, $(C_{1}-C_{10})$alkyl, $(C_{2}-C_{10})$alkenyl, $(C_{2}-C_{10})$alkynyl, $(C_{1}-C_{10})$alkoxy, $(C_{1}-C_{10})$alkyloxy$(C_{1}-C_{10})$alkyl, methoxy$(C_{1}-C_{6})$alkyl, carboxy$(C_{1}-C_{10})$alkyl, carbamoyl$(C_{1}-C_{10})$alkyl, $(C_{1}-C_{10})$alkyloxycarbonyl$(C_{3}-C_{10})$alkyl, $(C_{1}-C_{10})$alkylcarbonyl, cyclo$(C_{3}-C_{6})$alkyl, cyclo$(C_{3}-C_{6})$alkyl$(C_{1}-C_{10})$alkyl, fused bicyclyl, heterocyclyl, heterocyclyl$(C_{1}-C_{10})$alkyl, aryl, aralkyl, heteroaryl, $(C_{1}-C_{10})$alkylaryl, aryl$(C_{1}-C_{10})$alkyl, heteroaryl$(C_{1}-C_{10})$alkyl, $(C_{1}-C_{10})$alkylheteroaryl, aryloxyaryl, heteroaryloxyheteroaryl, heteroaryloxyaryl, aryloxyheteroaryl, heteroarylaryl, arylheteroaryl, biaryl, oxocyclo$(C_{1}-C_{6})$alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or $R^{N2}$ is forming an optionally substituted 3-, 4-, 5-, or 6-membered heterocycle together with $R^{2'}$ and the atoms to which they are connected, $R^{1}$ is selected from the group consisting of halogen, hydrogen, formyl, azido, nitro, cyano, hydroxy, sulfanyl, amino, carboxy, carbamoyl, —$N(R^{1a})_{2}$, —$C(O)OR^{1a}$, —$(CH_{2})_{q}C(O)OR^{1a}$, —$C(O)N(R^{1a})_{2}$, —$(CH_{2})_{q}C(O)N(R^{1a})_{2}$, an optionally substituted group selected from the group consisting of $(C_{1}-C_{10})$alkyl, $(C_{2}-C_{10})$alkenyl, $(C_{2}-C_{10})$alkynyl, $(C_{1}-C_{10})$alkoxy, $(C_{1}-C_{10})$alkyloxy$(C_{1}-C_{10})$alkyl, methoxy$(C_{1}-C_{6})$alkyl, carboxy$(C_{1}-C_{10})$alkyl, carbamoyl$(C_{1}-C_{10})$alkyl, $(C_{1}-C_{10})$alkyloxycarbonyl$(C_{3}-C_{10})$alkyl, $(C_{1}-C_{10})$alkylcarbonyl, cyclo$(C_{3}-C_{6})$alkyl, cyclo$(C_{3}-C_{6})$alkyl$(C_{1}-C_{10})$alkyl, fused bicyclyl, heterocyclyl, heterocyclyl$(C_{1}-C_{10})$alkyl, aryl, aralkyl, heteroaryl, $(C_{1}-C_{10})$alkylaryl, aryl$(C_{1}-C_{10})$alkyl, heteroaryl$(C_{1}-C_{10})$alkyl, $(C_{1}-C_{10})$alkylheteroaryl, aryloxyaryl, heteroaryloxyheteroaryl, heteroaryloxyaryl, aryloxyheteroaryl, heteroarylaryl, arylheteroaryl, biaryl, oxocyclo$(C_{1}-C_{6})$alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, $R^{2}$ and $R^{2'}$ are each independently selected from the group consisting of halogen, hydrogen, formyl, azido, nitro, cyano, hydroxy, sulfanyl, amino, carboxy, carbamoyl, —$N(R^{2a})_{2}$, —$C(O)OR^{2a}$, —$(CH_{2})_{q}C(O)OR^{2a}$, —$C(O)N(R^{2a})_{2}$, —$(CH_{2})_{q}C(O)N(R^{2a})_{2}$, —$(CH_{2})_{q}OC(O)R^{2a}$, —$(CH_{2})_{q}NHC(O)R^{2a}$, an optionally substituted group selected from the group consisting of $(C_{1}-C_{10})$alkyl, $(C_{2}-C_{10})$alkenyl, $(C_{2}-C_{10})$alkynyl, $(C_{1}-C_{10})$alkoxy, $(C_{1}-C_{10})$alkyloxy$(C_{1}-C_{10})$alkyl, methoxy$(C_{1}-C_{6})$alkyl, carboxy$(C_{1}-C_{10})$alkyl, carbamoyl$(C_{1}-C_{10})$alkyl, $(C_{1}-C_{10})$alkyloxycarbonyl$(C_{3}-C_{10})$alkyl, $(C_{1}-C_{10})$alkylcarbonyl, cyclo$(C_{3}-C_{6})$alkyl, cyclo$(C_{3}-C_{6})$alkyl$(C_{1}-C_{10})$alkyl, fused bicyclyl, heterocyclyl, heterocyclyl$(C_{1}-C_{10})$alkyl, $(C_{1}-C_{10})$alkyl heterocyclyl, aryl, aralkyl, heteroaryl, $(C_{1}-C_{10})$alkylaryl, aryl$(C_{1}-C_{10})$alkyl, heteroaryl$(C_{1}-C_{10})$alkyl, $(C_{1}-C_{10})$alkylheteroaryl, aryloxyaryl, heteroaryloxyheteroaryl, heteroaryloxyaryl, aryloxyheteroaryl, heteroarylaryl, arylheteroaryl, biaryl, oxocyclo$(C_{1}-C_{6})$alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or $R^{2}$ is forming an optionally substituted 3-, 4-, 5-, or 6-membered ring together with $R^{3}$ and the atoms to which they are connected, or $R^{2'}$ is forming an optionally substituted 3-, 4-, 5-, or 6-membered heterocycle together with $R^{2N}$ and the atoms to which they are connected, $R^{3}$ is selected from the group consisting of halogen, hydrogen, formyl, azido, nitro, cyano, hydroxy, sulfanyl, amino, carboxy, carbamoyl, —$N(R^{3a})_{2}$, —$C(O)OR^{3a}$, —$(CH_{2})_{q}C(O)OR^{3a}$, —$C(O)N(R^{3a})_{2}$, —$(CH_{2})_{q}C(O)N(R^{3a})_{2}$, —$(CH_{2})_{q}OC(O)R^{3a}$, —$(CH_{2})_{q}NHC(O)R^{3a}$, an optionally substituted group selected from the group consisting of $(C_{1}-C_{10})$alkyl, $(C_{2}-C_{10})$alkenyl, $(C_{2}-C_{10})$alkynyl, $(C_{1}-C_{10})$alkoxy, $(C_{1}-C_{10})$alkyloxy$(C_{1}-C_{10})$alkyl, methoxy$(C_{1}-C_{6})$alkyl, carboxy$(C_{1}-C_{10})$alkyl, carbamoyl$(C_{1}-C_{10})$alkyl, $(C_{1}-C_{10})$alkyloxycarbonyl$(C_{3}-C_{10})$alkyl, $(C_{1}-C_{10})$alkylcarbonyl, cyclo$(C_{3}-C_{6})$alkyl, cyclo$(C_{3}-C_{6})$alkyl$(C_{1}-C_{10})$alkyl, fused bicyclyl, heterocyclyl, heterocyclyl$(C_{1}-C_{10})$alkyl, $(C_{1}-C_{10})$alkyl heterocyclyl, aryl, aralkyl, heteroaryl, $(C_{1}-C_{10})$alkylaryl, aryl$(C_{1}-C_{10})$alkyl, heteroaryl$(C_{1}-C_{10})$alkyl, $(C_{1}-C_{10})$alkylheteroaryl, aryloxyaryl, heteroaryloxyheteroaryl, heteroaryloxyaryl, aryloxyheteroaryl, heteroarylaryl, arylheteroaryl, biaryl, oxocyclo$(C_{1}-C_{6})$alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or $R^{3}$ is forming an optionally substituted 3-, 4-, 5-, or 6-membered ring together with $R^{2}$ and the atoms to which they are connected, R⁴ and R⁵ are each independently selected from the group consisting of halogen, hydrogen, formyl, azido, nitro, cyano, hydroxy, sulfanyl, amino, carboxy, carbamoyl, —N($R^{4a}$)$_2$, —O$R^{4a}$, —C(O)O$R^{4a}$, —(CH$_2$)$_q$C(O)O$R^{4a}$, —C(O)N($R^{4a}$)$_2$, —(CH$_2$)$_q$C(O)N($R^{4a}$)$_2$, —(CH$_2$)$_q$OC(O)$R^{4a}$, —(CH$_2$)$_q$NHC(O)$R^{4a}$, an optionally substituted group selected from the group consisting of (C$_1$-C$_{18}$)alkyl, (C$_2$-C$_{18}$)alkenyl, (C$_2$-C$_{18}$)alkynyl, (C$_1$-C$_{18}$)alkoxy, (C$_1$-C$_{18}$)alkyloxy(C$_1$-C$_{18}$)alkyl, methoxy(C$_1$-C$_6$)alkyl, carboxy(C$_1$-C$_{10}$)alkyl, carbamoyl(C$_1$-C$_{10}$)alkyl, (C$_1$-C$_{10}$)alkyloxycarbonyl(C$_3$-C$_{10}$)alkyl, (C$_1$-C$_{10}$)alkylcarbonyl, cyclo(C$_3$-C$_6$)alkyl, cyclo(C$_3$-C$_6$)alkyl(C$_1$-C$_{18}$)alkyl, fused bicyclyl, heterocyclyl, heterocyclyl(C$_1$-C$_{18}$)alkyl, aryl, aralkyl, heteroaryl, (C$_1$-C$_{18}$)alkylaryl, aryl(C$_1$-C$_{18}$)alkyl, heteroaryl(C$_1$-C$_{18}$)alkyl, (C$_1$-C$_{18}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo(C$_1$-C$_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, $R^{1a}$, $R^{2a}$, $R^{3a}$, and $R^{4a}$ are each optionally substituted groups independently selected from the group consisting of hydrogen, (C$_1$-C$_{10}$)alkyl, (C$_2$-C$_{10}$)alkenyl, (C$_2$-C$_{10}$)alkynyl, (C$_1$-C$_{10}$)alkoxy, (C$_1$-C$_{10}$)alkyloxy(C$_1$-C$_{10}$)alkyl, methoxy(C$_1$-C$_6$)alkyl, carboxy(C$_1$-C$_{10}$)alkyl, carbonyl(C$_1$-C$_{10}$)alkyl, N—(C$_1$-C$_{10}$)alkyl-N—(C$_1$-C$_{10}$)alkylaminocarbonyl(C$_1$-C$_{10}$)alkyl, (C$_1$-C$_{10}$)alkyloxycarbonyl(C$_1$-C$_{10}$)alkyl, (C$_1$-C$_{10}$)alkylcarbonyl, cyclo(C$_3$-C$_6$)alkyl, cyclo(C$_3$-C$_6$)alkyl(C$_1$-C$_{10}$)alkyl, fused bicyclyl, heterocyclyl, heterocyclyl(C$_1$-C$_{10}$)alkyl, aryl, aralkyl, heteroaryl, (C$_1$-C$_{10}$)alkylaryl, aryl(C$_1$-C$_{10}$)alkyl, heteroaryl(C$_1$-C$_{10}$)alkyl, (C$_1$-C$_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo(C$_1$-C$_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or wherein two identical $R^{1a}$, $R^{2a}$, $R^{3a}$, or $R^{4a}$ together form an optionally substituted 4-, 5- or 6-membered heterocycle comprising the heteroatom to which both groups are connected; q is an integer selected from the group consisting of 1, 2, 3, 4, 5, 6, 7, 8, 9 and 10.

Another aspect of the present invention relates to a pharmaceutical composition comprising the compound described herein, or a pharmaceutically acceptable salt thereof.

Yet another aspect of the present invention is the compound described herein or a pharmaceutical composition described herein, for use as a medicament.

Still another aspect of the present invention is the compound described herein or a pharmaceutical composition described herein, for use in the treatment of cancer.

Figure 1:
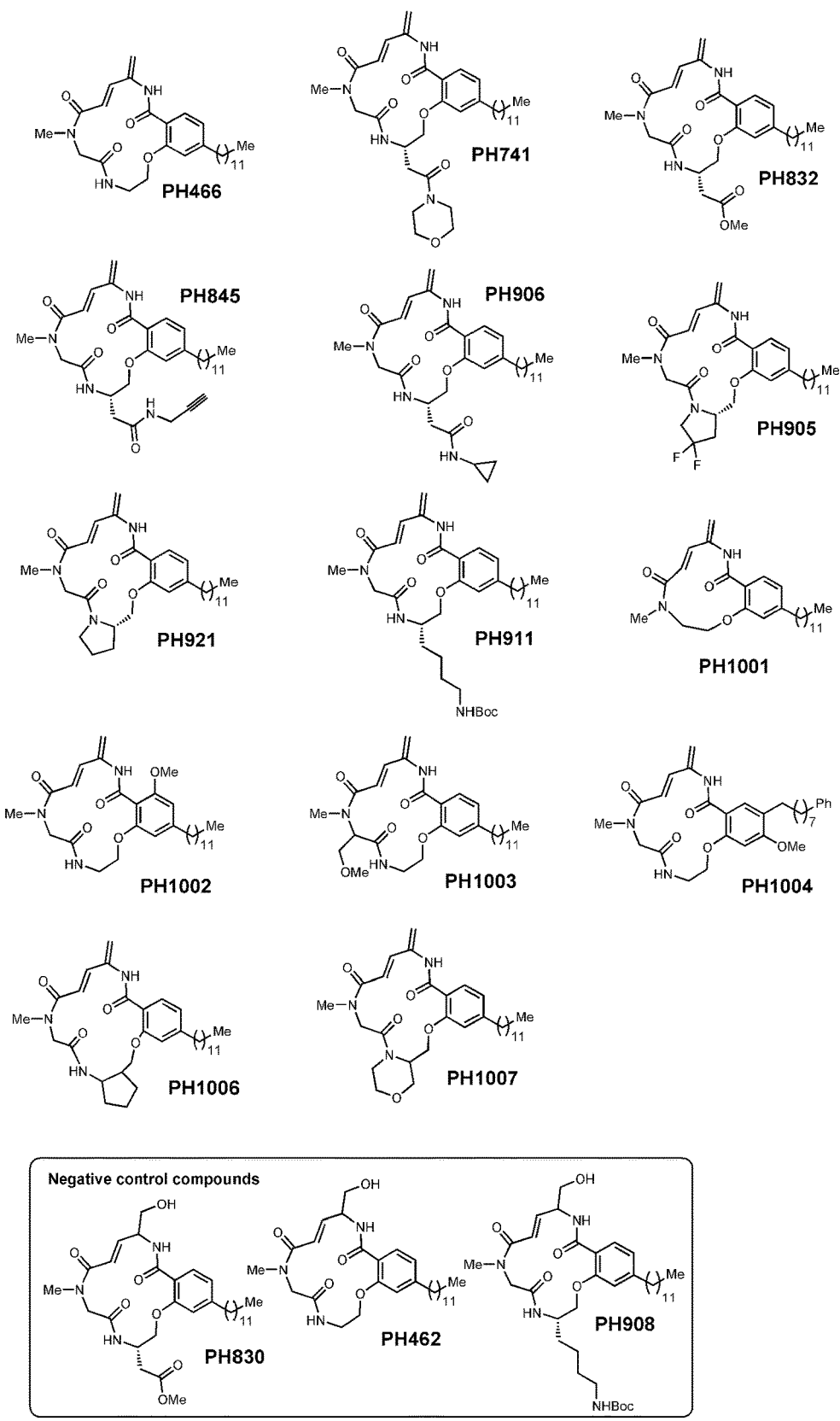
FIG. 1 shows the APD-CLD analogs and negative control compounds.

The present invention will now be described in more detail in the following.

DETAILED DESCRIPTION OF THE INVENTION

Definitions

Prior to discussing the present invention in further details, the following terms and conventions will first be defined:

Adjuvant

In the present context, the term "adjuvant" refers to a compound or mixture that enhances the immune response to an antigen. An adjuvant can serve as a tissue depot that slowly releases the antigen and as a lymphoid system activator, which non-specifically enhances the immune response. Often, a primary challenge with an antigen alone, in the absence of an adjuvant, will fail to elicit a humoral or cellular immune response.

Alkyl

In the present context, the term "alkyl" refers to a radical of a hydrocarbon, such as a linear or branched hydrocarbon.

Aryl

In the present context, the term "aryl" refers to a radical of an aromatic rings structure, such as, but not limited to benzene, naphthalene, and toluene.

Aralkyl

In the present context, the term "aralkyl" refers to an alkyl wherein one or more hydrogen atoms have been replaced by aryl groups.

Carrier

In the present context, the term "carrier" refers to any solvents, dispersion media, vehicles, coatings, diluents, antibacterial and antifungal agents, isotonic and absorption delaying agents, buffers, carrier solutions, suspensions, colloids, and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

Diluent

In the present context, the term "diluent" refers to a substance that serves as a vehicle or medium for a drug or other active substance.

Excipient

In the present context, the term "excipient" refers to a diluent, adjuvant, carrier, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Halogen

In the present context, the term "halogen" refers to any of chloro, fluoro, bromo, and iodo.

Heteroatom

In the present context, the term "heteroatom" refers to any atom that is not carbon or hydrogen, such as, but not limited to N, O, and S.

Heterocyclyl

In the present context, the term "heterocyclyl" refers to a radical of an aliphatic saturated or unsaturated rings structure comprising one or more heteroatoms.

Heteroaryl

In the present context, the term "heteroaryl" refers to a radical of an aromatic rings structure comprising one or more heteroatoms.

Hypoxic Cancer

In the present context, the term "hypoxic cancer" refers to cancer cells in a region of the body wherein the oxygen content is lower than normal. Cancerous tissues, and especially solid tumors, are known to rapidly outgrow their own blood supply and thus to form hypoxic regions.

The term "hypoxic cells" refers to cells, which reside in a low oxygenated environment, such as but not limited to, an oxygen tension of less than pO2 of 20 mmHg.

The term "hypoxic tumors" refers to tumors which have areas of hypoxia or hypoxia-like conditions.

Normoxic

In the present context, the term "normoxic" refers to situations/conditions wherein the oxygen content is at a normal level usually found in tissues.

Radical

In the present context, the term "radical" refers to a compound wherein a hydrogen has been removed thereby forming a radical of said compound, which compound is thereby able to form a bond to another radical.

Pharmaceutical Composition

In the present context, the term "pharmaceutical composition" refers to a composition suspended in a suitable amount of a pharmaceutical acceptable diluent or excipient.

Pharmaceutically Acceptable Salt

In the present context, the term "pharmaceutically acceptable salt" refers to a salt that can be formulated into a composition for pharmaceutical use including, e.g., metal salts (sodium, potassium, magnesium, calcium, etc.) and salts of ammonia or organic amines.

Subject

The term "subject" comprises humans of all ages, other primates (e.g., cynomolgus monkeys, rhesus monkeys) and mammals in general. Preferred subjects are humans.

The term "subject" primarily is a subject suffering from cancer or another disease with a hypoxia or hypoxia-like condition in need of a treatment that selectively kills hypoxic or hypoxia-like cells, such that the hypoxic cells in the subject are depleted. However, the term "subject" also includes healthy subjects of the population.

Therapeutic Agents

In the present context, a "therapeutic agent" refers to a compound capable to causing a therapeutic effect in the body. Examples of therapeutic agents include, but are not limited to, proteins, peptides, small molecule drugs, anti-cancer agents and pharmaceutically acceptable salts thereof.

Furthermore, in the present context any one of (O) refers to an oxygen atom connected with a double bond. Also, the chemical nomenclature used herein may be exemplified by the group of substituents termed "cyclo($C_3$-$C_6$)alkyl($C_1$-$C_{18}$)alkyl", which group includes structures such as, but not limited to: cyclohexanylethyl and cyclohexanylnonyl, and such as cyclopropylethyl.

The invention of the present application provides compounds that are specifically active against cancer cells in a hypoxic micro-environment. The effect is a consequence of the compounds becoming toxic when transported to cancerous tissues known to create regions depleted of oxygen. In addition, the compounds of the invention comprise specific structural features resulting in good pharmacokinetic properties, such as being hypoxia selective, stable towards hydrolytic degradation, and efficient at killing the targeted cells.

Another important factor to consider is the availability of the compounds. Whereas access to the naturally occurring APD-CLDs is delimited by their biological occurrence, the compounds of the present invention are readily available by chemical synthesis, thus potentially reaching a larger group of patients in need thereof. The compounds of the present invention exercise the attractive hypoxia selectivity of the natural APD-CLDs, yet also include additional stabilizing features further increasing their pharmacokinetic properties. In this regard, the natural compounds exhibit a poor stability profile, so although they are very hypoxia selective, their inherent instability eliminates chances of synthesis thereof and seemingly reduces their therapeutic potential.

Thus, one aspect of the invention of the present application relates to a compound of Formula (1)

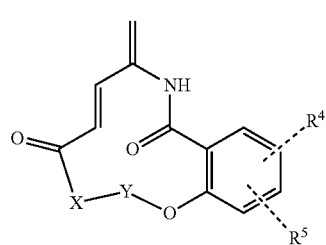

(1)

wherein, X is selected from the group consisting of a bond, or —NR$^{N1}$CHR$^1$C(O)—' for which —' denotes the bond connecting X to Y, Y is selected from the group consisting of
—NR$^{N2}$CR$^2$R$^{2'}$CHR$^3$—*,
—NR$^{N2}$CR$^2$R$^{2'}$CHR$^3$CH$_2$—*, for which —* denotes the bond connecting Y to O R$^{N1}$ and R$^{N2}$ are each optionally substituted groups independently selected from the group consisting of hydrogen, (C$_1$-C$_{10}$)alkyl, (C$_2$-C$_{10}$)alkenyl, (C$_2$-C$_{10}$)alkynyl, (C$_1$-C$_{10}$)alkoxy, (C$_1$-C$_{10}$)alkyloxy(C$_1$-C$_{10}$)alkyl, methoxy(C$_1$-C$_6$)alkyl, carboxy(C$_1$-C$_{10}$)alkyl, carbamoyl(C$_1$-C$_{10}$)alkyl, (C$_1$-C$_{10}$)alkyloxycarbonyl(C$_3$-C$_{10}$) alkyl, (C$_1$-C$_{10}$)alkylcarbonyl, cyclo(C$_3$-C$_6$)alkyl, cyclo (C$_3$-C$_6$)alkyl(C$_1$-C$_{10}$)alkyl, fused bicyclyl, heterocyclyl, heterocyclyl(C$_1$-C$_{10}$)alkyl, aryl, aralkyl, heteroaryl, (C$_1$-C$_{10}$)alkylaryl, aryl(C$_1$-C$_{10}$)alkyl, heteroaryl(C$_1$-C$_{10}$)alkyl, (C$_1$-C$_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo(C$_1$-C$_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or R$^{N2}$ is forming an optionally substituted 3-, 4-, 5-, or 6-membered heterocycle together with R$^{2'}$ and the atoms to which they are connected, R$^1$ is selected from the group consisting of halogen, hydrogen, formyl, azido, nitro, cyano, hydroxy, sulfanyl, amino, carboxy, carbamoyl, —N(R$^{1a}$)$_2$, —C(O)OR$^{1a}$, —(CH$_2$)$_q$C(O)OR$^{1a}$, —C(O)N(R$^{1a}$)$_2$, —(CH$_2$)$_q$C(O)N(R$^{1a}$)$_2$, an optionally substituted group selected from the group consisting of (C$_1$-C$_{10}$)alkyl, (C$_2$-C$_{10}$)alkenyl, (C$_2$-C$_{10}$)alkynyl, (C$_1$-C$_{10}$)alkoxy, (C$_1$-C$_{10}$)alkyloxy(C$_1$-C$_{10}$)alkyl, methoxy(C$_1$-C$_6$)alkyl, carboxy (C$_1$-C$_{10}$)alkyl, carbamoyl(C$_1$-C$_{10}$)alkyl, (C$_1$-C$_{10}$)alkyloxycarbonyl(C$_3$-C$_{10}$)alkyl, (C$_1$-C$_{10}$)alkylcarbonyl, cyclo(C$_3$-C$_6$)alkyl, cyclo(C$_3$-C$_6$)alkyl(C$_1$-C$_{10}$)alkyl, fused bicyclyl, heterocyclyl, heterocyclyl(C$_1$-C$_{10}$)alkyl, aryl, aralkyl, heteroaryl, (C$_1$-C$_{10}$)alkylaryl, aryl(C$_1$-C$_{10}$)alkyl, heteroaryl(C$_1$-C$_{10}$)alkyl, (C$_1$-C$_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo(C$_1$-C$_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, R$^2$ and R$^{2'}$ are each independently selected from the group consisting of halogen, hydrogen, formyl, azido, nitro, cyano, hydroxy, sulfanyl, amino, carboxy, carbamoyl, —N(R$^{2a}$)$_2$, —C(O)OR$^{2a}$, —(CH$_2$)$_q$C(O)OR$^{2a}$, —C(O)N(R$^{2a}$)$_2$, —(CH$_2$)$_q$C(O)N(R$^{2a}$)$_2$, —(CH$_2$)$_q$OC(O)R$^{2a}$, —(CH$_2$)$_q$NHC(O)R$^{2a}$, an optionally substituted group selected from the group consisting of (C$_1$-C$_{10}$)alkyl, (C$_2$-C$_{10}$)alkenyl, (C$_2$-C$_{10}$)alkynyl, (C$_1$-C$_{10}$)alkoxy, (C$_1$-C$_{10}$)alkyloxy(C$_1$-C$_{10}$)alkyl, methoxy(C$_1$-C$_6$)alkyl, carboxy(C$_1$-C$_{10}$)alkyl, carbamoyl(C$_1$-C$_{10}$)alkyl, (C$_1$-C$_{10}$)alkyloxycarbonyl(C$_3$-C$_{10}$)alkyl, (C$_1$-C$_{10}$)alkylcarbonyl, cyclo(C$_3$-C$_6$)alkyl, cyclo(C$_3$-C$_6$)alkyl(C$_1$-C$_{10}$) alkyl, fused bicyclyl, heterocyclyl, heterocyclyl(C$_1$-C$_{10}$)alkyl, (C$_1$-C$_{10}$)alkyl heterocyclyl, aryl, aralkyl, heteroaryl, (C$_1$-C$_{10}$)alkylaryl, aryl(C$_1$-C$_{10}$)alkyl, heteroaryl(C$_1$-C$_{10}$)alkyl, (C$_1$-C$_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo(C$_1$-C$_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or R$^2$ is forming an optionally substituted 3-, 4-, 5-, or 6-membered ring together with R$^3$ and the atoms to which they are connected, or R$^{2'}$ is forming an optionally substituted 3-, 4-, 5-, or 6-membered heterocycle together with R$^{2N}$ and the atoms to which they are connected, R$^3$ is selected from the group consisting of halogen, hydrogen, formyl, azido, nitro, cyano, hydroxy, sulfanyl, amino, carboxy, carbamoyl, —N(R$^{3a}$)$_2$, —C(O)OR$^{3a}$, —(CH$_2$)$_q$C(O)OR$^{3a}$, —C(O)N(R$^{3a}$)$_2$, —(CH$_2$)$_q$C(O)N(R$^{3a}$)$_2$, —(CH$_2$)$_q$OC(O)R$^{3a}$, —(CH$_2$)$_q$NHC(O)R$^{3a}$, an optionally substituted group selected from the group consisting of (C$_1$-C$_{10}$)alkyl, (C$_2$-C$_{10}$)alkenyl, (C$_2$-C$_{10}$)alkynyl, (C$_1$-C$_{10}$)alkoxy, (C$_1$-C$_{10}$)alkyloxy (C$_1$-C$_{10}$)alkyl, methoxy(C$_1$-C$_6$)alkyl, carboxy(C$_1$-C$_{10}$) alkyl, carbamoyl(C$_1$-C$_{10}$)alkyl, (C$_1$-C$_{10}$)alkyloxycarbonyl(C$_3$-C$_{10}$)alkyl, (C$_1$-C$_{10}$)alkylcarbonyl, cyclo(C$_3$-C$_6$)alkyl, cyclo(C$_3$-C$_6$)alkyl(C$_1$-C$_{10}$)alkyl, fused bicyclyl, heterocyclyl, heterocyclyl(C$_1$-C$_{10}$)alkyl, (C$_1$-C$_{10}$)alkyl heterocyclyl, aryl, aralkyl, heteroaryl, (C$_1$-C$_{10}$)alkylaryl, aryl(C$_1$-C$_{10}$)alkyl, heteroaryl(C$_1$-C$_{10}$)alkyl, (C$_1$-C$_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo(C$_1$-C$_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or R$^3$ is forming an optionally substituted 3-, 4-, 5-, or 6-membered ring together with R$^2$ and the atoms to which they are connected, R$^4$ and R$^5$ are each independently selected from the group consisting of halogen, hydrogen, formyl, azido, nitro, cyano, hydroxy, sulfanyl, amino, carboxy, carbamoyl, —N(R$^{4a}$)$_2$, —OR$^{4a}$, —C(O)OR$^{4a}$, —(CH$_2$)$_q$C(O)OR$^{4a}$, —C(O)N(R$^{4a}$)$_2$, —(CH$_2$)$_q$C(O)N(R$^{4a}$)$_2$, —(CH$_2$)$_q$OC(O)R$^{4a}$, —(CH$_2$)$_q$NHC(O)R$^{4a}$, an optionally substituted group consisting of (C$_1$-C$_{18}$)alkyl, (C$_2$-C$_{18}$)alkenyl, (C$_2$-C$_{18}$)alkynyl, (C$_1$-C$_{18}$)alkoxy, (C$_1$-C$_{18}$)alkyloxy(C$_1$-C$_{18}$)alkyl, methoxy(C$_1$-C$_6$)alkyl, carboxy(C$_1$-C$_{10}$)alkyl, carbamoyl(C$_1$-C$_{10}$)alkyl, (C$_1$-C$_{10}$)alkyloxycarbonyl(C$_3$-C$_{10}$) alkyl, (C$_1$-C$_{10}$)alkylcarbonyl, cyclo(C$_3$-C$_6$)alkyl, cyclo (C$_3$-C$_6$)alkyl(C$_1$-C$_{18}$)alkyl, fused bicyclyl, heterocyclyl, heterocyclyl(C$_1$-C$_{18}$)alkyl, aryl, aralkyl, heteroaryl, (C$_1$-C$_{18}$)alkylaryl, aryl(C$_1$-C$_{18}$)alkyl, heteroaryl(C$_1$-C$_{18}$)alkyl, (C$_1$-C$_{18}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo(C$_1$-C$_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, R$^{1a}$, R$^{2a}$, R$^{3a}$, and R$^{4a}$ are each optionally substituted groups independently selected from the group consisting of hydrogen, (C$_1$-C$_{10}$)alkyl, (C$_2$-C$_{10}$)alkenyl, (C$_2$-C$_{10}$)alkynyl, (C$_1$-C$_{10}$)alkoxy, (C$_1$-C$_{10}$)alkyloxy(C$_1$-C$_{10}$)alkyl, methoxy(C$_1$-C$_6$)alkyl, carboxy(C$_1$-C$_{10}$) alkyl, carbonyl(C$_1$-C$_{10}$)alkyl, N—(C$_1$-C$_{10}$)alkyl-N—(C$_1$-C$_{10}$)alkylaminocarbonyl(C$_1$-C$_{10}$)alkyl, (C$_1$-C$_{10}$) alkyloxycarbonyl(C$_1$-C$_{10}$)alkyl, (C$_1$-C$_{10}$) alkylcarbonyl, cyclo(C$_3$-C$_6$)alkyl, cyclo(C$_3$-C$_6$)alkyl (C$_1$-C$_{10}$)alkyl, fused bicyclyl, heterocyclyl, heterocyclyl(C$_1$-C$_{10}$)alkyl, aryl, aralkyl, heteroaryl, ($C_1$-$C_{10}$)alkylaryl, aryl($C_1$-$C_{10}$)alkyl, heteroaryl($C_1$-$C_{10}$)alkyl, ($C_1$-$C_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo ($C_1$-$C_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or wherein two identical $R^{1a}$, $R^{2a}$, $R^{3a}$, or $R^{4a}$ together form an optionally substituted 4-, 5- or 6-membered heterocycle comprising the heteroatom to which both groups are connected; q is an integer selected from the group consisting of 1, 2, 3, 4, 5, 6, 7, 8, 9 and 10.

An embodiment of the present invention relates to the compound as described herein, wherein the compound is the compound as described herein or pharmaceutically acceptable salt, stereoisomer, solvate, or hydrate thereof.

The compounds are characterized in that they comprise the biologically active 4-amido-2,4-pentadienoate (APD) moiety having two conjugated double bonds, wherein one of the double bonds is in a terminal position. The features of the compounds being especially important for the hydrolytic stability and ease of handling are the incorporated benzene ring and the ether connection.

Thus, the APD-moiety, benzene ring, and ether connection are all important features of the invention and together establish the general concept for all macrocycles of the invention.

A more specific embodiment of the present invention relates to the compound as described herein, wherein $R^{N1}$ is selected from the group consisting of hydrogen, methyl, ethyl, isopropyl, benzyl, trifluoromethyl, and trifluoroethyl, $R^{N2}$ is selected from the group consisting of hydrogen, methyl, ethyl, isopropyl, benzyl, trifluoromethyl, and trifluoroethyl, or $R^{N2}$ is forming an optionally substituted 3-, 4-, 5-, or 6-membered heterocycle together with $R^{2'}$ and the atoms to which they are connected, $R^1$ is hydrogen or methyl, $R^2$ and $R^{2'}$ are each independently selected from the group consisting of hydrogen, cyano, carboxy, carbamoyl, —(CH$_2$)$_q$C(O)OR$^{2a}$, —(CH$_2$)$_q$C(O)N(R$^{2a}$)$_2$, —(CH$_2$)$_q$OC(O)R$^{2a}$, —(CH$_2$)$_q$NHC(O)R$^{2a}$, an optionally substituted group consisting of ($C_1$-$C_{10}$)alkyl, ($C_2$-$C_{10}$)alkenyl, ($C_2$-$C_{10}$)alkynyl, ($C_1$-$C_{10}$)alkyloxy($C_1$-$C_{10}$)alkyl, cyclo($C_3$-$C_6$)alkyl, heterocyclyl, heterocyclyl($C_1$-$C_{10}$)alkyl, ($C_1$-$C_{10}$)alkyl heterocyclyl, aryl, aralkyl, heteroaryl, ($C_1$-$C_{10}$)alkylaryl, aryl($C_1$-$C_{10}$)alkyl, heteroaryl($C_1$-$C_{10}$)alkyl, ($C_1$-$C_{10}$)alkylheteroaryl, oxocyclo($C_1$-$C_6$)alkyl, radical of (α-, β-, γ-, or δ-)lactam, and a radical of (α-, β-, γ-, or δ-)lactone, or $R^2$ is forming an optionally substituted 3-, 4-, 5-, or 6-membered ring together with $R^3$ and the atoms to which they are connected, or $R^{2'}$ is forming an optionally substituted 3-, 4-, 5-, or 6-membered heterocycle together with $R^{2N}$ and the atoms to which they are connected, $R^3$ is selected from the group consisting of hydrogen, carboxy, carbamoyl, —(CH$_2$)$_q$C(O)OR$^{3a}$, —(CH$_2$)$_q$C(O)N(R$^{3a}$)$_2$, —(CH$_2$)$_q$OC(O)R$^{3a}$, —(CH$_2$)$_q$NHC(O)R$^{3a}$, an optionally substituted group selected from the group consisting of ($C_1$-$C_{10}$)alkyl, ($C_1$-$C_{10}$)alkyloxy($C_1$-$C_{10}$)alkyl, cyclo($C_3$-$C_6$)alkyl, heterocyclyl, heterocyclyl($C_1$-$C_{10}$)alkyl, ($C_1$-$C_{10}$)alkyl heterocyclyl, aryl, aralkyl, heteroaryl, ($C_1$-$C_{10}$)alkylaryl, and ($C_1$-$C_{10}$)alkylheteroaryl, or $R^3$ is forming an optionally substituted 3-, 4-, 5-, or 6-membered ring together with $R^2$ and the atoms to which they are connected, $R^4$ and $R^5$ are each independently selected from the group consisting of halogen, hydrogen, —N(R$^{4a}$)$_2$, —OR$^{4a}$, —(CH$_2$)$_q$C(O)OR$^{4a}$, —(CH$_2$)$_q$C(O)N(R$^{4a}$)$_2$, —(CH$_2$)$_q$OC(O)R$^{4a}$, —(CH$_2$)$_q$NHC(O)R$^{4a}$, an optionally substituted group selected from the group consisting of ($C_1$-$C_{18}$)alkyl, ($C_1$-$C_{18}$)alkyloxy($C_1$-$C_{18}$)alkyl, cyclo($C_3$-$C_6$)alkyl, cyclo($C_3$-$C_6$)alkyl($C_1$-$C_{18}$)alkyl, fused bicyclyl, heterocyclyl, heterocyclyl($C_1$-$C_{18}$)alkyl, aryl, aralkyl, heteroaryl, ($C_1$-$C_{18}$)alkylaryl, aryl($C_1$-$C_{18}$)alkyl, heteroaryl($C_1$-$C_{18}$)alkyl, and ($C_1$-$C_{18}$)alkylheteroaryl, $R^{2a}$, $R^{3a}$, and $R^{4a}$ are each optionally substituted groups independently selected from the group consisting of hydrogen, ($C_1$-$C_{10}$)alkyl, ($C_2$-$C_{10}$)alkenyl, ($C_2$-$C_{10}$)alkynyl, ($C_1$-$C_{10}$)alkoxy, ($C_1$-$C_{10}$)alkyloxy($C_1$-$C_{10}$)alkyl, carboxy($C_1$-$C_{10}$)alkyl, carbonyl($C_1$-$C_{10}$)alkyl, cyclo($C_3$-$C_6$)alkyl, cyclo($C_3$-$C_6$)alkyl($C_1$-$C_{10}$)alkyl, fused bicyclyl, heterocyclyl, heterocyclyl($C_1$-$C_{10}$)alkyl, aryl, aralkyl, heteroaryl, ($C_1$-$C_{10}$)alkylaryl, aryl ($C_1$-$C_{10}$)alkyl, heteroaryl($C_1$-$C_{10}$)alkyl, and ($C_1$-$C_{10}$)alkylheteroaryl, or wherein two identical $R^{2a}$, $R^{3a}$, or $R^{4a}$ together form an optionally substituted 4-, 5- or 6-membered heterocycle comprising the heteroatom to which both groups are connected; q is an integer selected from the group consisting of 1, 2, 3, 4, 5, 6, 7, 8, 9 and 10.

Although, another embodiment of the present invention relates to the compound as described herein, wherein X is —NR$^{N1}$CHR$^1$C(O)—';

Y is —NR$^{N2}$CR$^2$R$^{2'}$CHR$^3$—*;

$R^{N1}$ is methyl;

$R^1$ is selected from the group consisting of halogen, hydrogen, formyl, azido, nitro, cyano, hydroxy, sulfanyl, amino, carboxy, carbamoyl, —N(R$^{1a}$)$_2$, —C(O)OR$^{1a}$, —(CH$_2$)$_q$C(O)OR$^{1a}$, —C(O)N(R$^{1a}$)$_2$, —(CH$_2$)$_q$C(O)N(R$^{1a}$)$_2$, an optionally substituted group selected from the group consisting of ($C_1$-$C_{10}$)alkyl, ($C_2$-$C_{10}$)alkenyl, ($C_2$-$C_{10}$)alkynyl, ($C_1$-$C_{10}$)alkoxy, ($C_1$-$C_{10}$)alkyloxy($C_1$-$C_{10}$)alkyl, methoxy($C_1$-$C_6$)alkyl, carboxy ($C_1$-$C_{10}$)alkyl, carbamoyl($C_1$-$C_{10}$)alkyl, ($C_1$-$C_{10}$)alkyloxycarbonyl($C_3$-$C_{10}$)alkyl, ($C_1$-$C_{10}$)alkylcarbonyl, cyclo($C_3$-$C_6$)alkyl, cyclo($C_3$-$C_6$)alkyl ($C_1$-$C_{10}$)alkyl, fused bicyclyl, heterocyclyl, heterocyclyl($C_1$-$C_{10}$)alkyl, aryl, aralkyl, heteroaryl, ($C_1$-$C_{10}$)alkylaryl, aryl($C_1$-$C_{10}$)alkyl, heteroaryl($C_1$-$C_{10}$)alkyl, ($C_1$-$C_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo ($C_1$-$C_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil;

$R^{N2}$ is an optionally substituted groups independently selected from the group consisting of hydrogen, ($C_1$-$C_{10}$)alkyl, ($C_2$-$C_{10}$)alkenyl, ($C_2$-$C_{10}$)alkynyl, ($C_1$-$C_{10}$)alkoxy, ($C_1$-$C_{10}$)alkyloxy($C_1$-$C_{10}$)alkyl, methoxy($C_1$-$C_6$)alkyl, carboxy($C_1$-$C_{10}$)alkyl, carbamoyl($C_1$-$C_{10}$)alkyl, ($C_1$-$C_{10}$)alkyloxycarbonyl($C_3$-$C_{10}$)alkyl, ($C_1$-$C_{10}$)alkylcarbonyl, cyclo($C_3$-$C_6$)alkyl, cyclo($C_3$-$C_6$)alkyl($C_1$-$C_{10}$)alkyl, fused bicyclyl, heterocyclyl, heterocyclyl($C_1$-$C_{10}$)alkyl, aryl, aralkyl, heteroaryl, ($C_1$-$C_{10}$)alkylaryl, aryl($C_1$-$C_{10}$)alkyl, heteroaryl($C_1$-$C_{10}$)alkyl, ($C_1$-$C_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo($C_1$-$C_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or $R^{N2}$ is forming an optionally substituted 3-, 4-, 5-, or 6-membered heterocycle together with $R^{2'}$ and the atoms to which they are connected;

$R^2$ and $R^{2'}$ are each independently selected from the group consisting of halogen, hydrogen, formyl, azido, nitro, cyano, hydroxy, sulfanyl, amino, carboxy, carbamoyl, —N($R^{2a}$)$_2$, —C(O)O$R^{2a}$, —(CH$_2$)$_q$C(O)O$R^{2a}$, —C(O)N($R^{2a}$)$_2$, —(CH$_2$)$_q$C(O)N($R^{2a}$)$_2$, —(CH$_2$)$_q$OC(O)$R^{2a}$, —(CH$_2$)$_q$NHC(O)$R^{2a}$, an optionally substituted group selected from the group consisting of ($C_1$-$C_{10}$)alkyl, ($C_2$-$C_{10}$)alkenyl, ($C_2$-$C_{10}$)alkynyl, ($C_1$-$C_{10}$)alkoxy, ($C_1$-$C_{10}$)alkyloxy($C_1$-$C_{10}$)alkyl, methoxy($C_1$-$C_6$)alkyl, carboxy($C_1$-$C_{10}$)alkyl, carbamoyl($C_1$-$C_{10}$)alkyl, ($C_1$-$C_{10}$)alkyloxycarbonyl($C_3$-$C_{10}$)alkyl, ($C_1$-$C_{10}$)alkylcarbonyl, cyclo($C_3$-$C_6$)alkyl, cyclo($C_3$-$C_6$)alkyl($C_1$-$C_{10}$)alkyl, fused bicyclyl, heterocyclyl, heterocyclyl($C_1$-$C_{10}$)alkyl, ($C_1$-$C_{10}$)alkyl heterocyclyl, aryl, aralkyl, heteroaryl, ($C_1$-$C_{10}$)alkylaryl, aryl($C_1$-$C_{10}$)alkyl, heteroaryl($C_1$-$C_{10}$)alkyl, ($C_1$-$C_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo($C_1$-$C_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or $R^2$ is forming an optionally substituted 3-, 4-, 5-, or 6-membered ring together with $R^3$ and the atoms to which they are connected, or $R^{2'}$ is forming an optionally substituted 3-, 4-, 5-, or 6-membered heterocycle together with $R^{2N}$ and the atoms to which they are connected;

$R^3$ is selected from the group consisting of halogen, hydrogen, formyl, azido, nitro, cyano, hydroxy, sulfanyl, amino, carboxy, carbamoyl, —N($R^{3a}$)$_2$, —C(O)O$R^{3a}$, —(CH$_2$)$_q$C(O)O$R^{3a}$, —C(O)N($R^{3a}$)$_2$, —(CH$_2$)$_q$C(O)N($R^{3a}$)$_2$, —(CH$_2$)$_q$OC(O)$R^{3a}$, —(CH$_2$)$_q$NHC(O)$R^{3a}$, an optionally substituted group selected from the group consisting of ($C_1$-$C_{10}$)alkyl, ($C_2$-$C_{10}$)alkenyl, ($C_2$-$C_{10}$)alkynyl, ($C_1$-$C_{10}$)alkoxy, ($C_1$-$C_{10}$)alkyloxy($C_1$-$C_{10}$)alkyl, methoxy($C_1$-$C_6$)alkyl, carboxy($C_1$-$C_{10}$)alkyl, carbamoyl($C_1$-$C_{10}$)alkyl, ($C_1$-$C_{10}$)alkyloxycarbonyl($C_3$-$C_{10}$)alkyl, ($C_1$-$C_{10}$)alkylcarbonyl, cyclo($C_3$-$C_6$)alkyl, cyclo($C_3$-$C_6$)alkyl($C_1$-$C_{10}$)alkyl, fused bicyclyl, heterocyclyl, heterocyclyl($C_1$-$C_{10}$)alkyl, ($C_1$-$C_{10}$)alkyl heterocyclyl, aryl, aralkyl, heteroaryl, ($C_1$-$C_{10}$)alkylaryl, aryl($C_1$-$C_{10}$)alkyl, heteroaryl($C_1$-$C_{10}$)alkyl, ($C_1$-$C_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo($C_1$-$C_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or $R^3$ is forming an optionally substituted 3-, 4-, 5-, or 6-membered ring together with $R^2$ and the atoms to which they are connected;

$R^{1a}$, $R^{2a}$, and $R^{3a}$ are each optionally substituted groups independently selected from the group consisting of hydrogen, ($C_1$-$C_{10}$)alkyl, ($C_2$-$C_{10}$)alkenyl, ($C_2$-$C_{10}$)alkynyl, ($C_1$-$C_{10}$)alkoxy, ($C_1$-$C_{10}$)alkyloxy($C_1$-$C_{10}$)alkyl, methoxy($C_1$-$C_6$)alkyl, carboxy($C_1$-$C_{10}$)alkyl, carbonyl($C_1$-$C_{10}$)alkyl, N—($C_1$-$C_{10}$)alkyl-N—($C_1$-$C_{10}$)alkylaminocarbonyl($C_1$-$C_{10}$)alkyl, ($C_1$-$C_{10}$)alkyloxycarbonyl($C_1$-$C_{10}$)alkyl, ($C_1$-$C_{10}$)alkylcarbonyl, cyclo($C_3$-$C_6$)alkyl, cyclo($C_3$-$C_6$)alkyl($C_1$-$C_{10}$)alkyl, fused bicyclyl, heterocyclyl, heterocyclyl($C_1$-$C_{10}$)alkyl, aryl, aralkyl, heteroaryl, ($C_1$-$C_{10}$)alkylaryl, aryl($C_1$-$C_{10}$)alkyl, heteroaryl($C_1$-$C_{10}$)alkyl, ($C_1$-$C_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo($C_1$-$C_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or wherein two identical $R^{1a}$, $R^{2a}$, or $R^{3a}$ together form an optionally substituted 4-, 5- or 6-membered heterocycle comprising the heteroatom to which both groups are connected; q is an integer selected from the group consisting of 1, 2, 3, 4, 5, 6, 7, 8, 9 and 10.

However, a preferred embodiment of the present invention relates to the compound as described herein, wherein the compound is represented by formula (2)

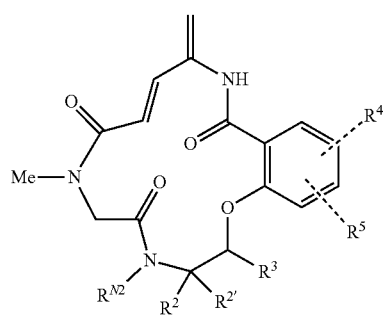

(2)

wherein $R^{N2}$ is selected from the group consisting of hydrogen, methyl, ethyl, isopropyl, benzyl, trifluoromethyl, and trifluoroethyl, or $R^{N2}$ is forming an optionally substituted 3-, 4-, 5-, or 6-membered heterocycle together with $R^{2'}$ and the atoms to which they are connected, $R^2$ and $R^{2'}$ are each independently selected from the group consisting of hydrogen, cyano, carboxy, carbamoyl, —(CH$_2$)$_q$C(O)O$R^{2a}$, —(CH$_2$)$_q$C(O)N($R^{2a}$)$_2$, —(CH$_2$)$_q$OC(O)$R^{2a}$, —(CH$_2$)$_q$NHC(O)$R^{2a}$, an optionally substituted group selected from the group consisting of ($C_1$-$C_{10}$)alkyl, ($C_2$-$C_{10}$)alkenyl, ($C_2$-$C_{10}$)alkynyl, ($C_1$-$C_{10}$)alkyloxy($C_1$-$C_{10}$)alkyl, cyclo($C_3$-$C_6$)alkyl, heterocyclyl, heterocyclyl($C_1$-$C_{10}$)alkyl, ($C_1$-$C_{10}$)alkyl heterocyclyl, aryl, aralkyl, heteroaryl, ($C_1$-$C_{10}$)alkylaryl, aryl($C_1$-$C_{10}$)alkyl, heteroaryl($C_1$-$C_{10}$)alkyl, ($C_1$-$C_{10}$)alkylheteroaryl, oxocyclo($C_1$-$C_6$)alkyl, radical of (α-, β-, γ-, or δ-)lactam, and a radical of (α-, β-, γ-, or δ-)lactone, or $R^2$ is forming an optionally substituted 3-, 4-, 5-, or 6-membered ring together with $R^3$ and the atoms to which they are connected, or $R^{2'}$ is forming an optionally substituted 3-, 4-, 5-, or 6-membered heterocycle together with $R^{2N}$ and the atoms to which they are connected, $R^3$ is selected from the group consisting of hydrogen, carboxy, carbamoyl, —(CH$_2$)$_q$C(O)O$R^{3a}$, —(CH$_2$)$_q$C(O)N($R^{3a}$)$_2$, —(CH$_2$)$_q$OC(O)$R^{3a}$, —(CH$_2$)$_q$NHC(O)$R^{3a}$, an optionally substituted group selected from the group consisting of $(C_1-C_{10})$alkyl, $(C_1-C_{10})$alkyloxy $(C_1-C_{10})$alkyl, cyclo$(C_3-C_6)$alkyl, heterocyclyl, heterocyclyl$(C_1-C_{10})$alkyl, $(C_1-C_{10})$alkyl heterocyclyl, aryl, aralkyl, heteroaryl, $(C_1-C_{10})$alkylaryl, and $(C_1-C_{10})$alkylheteroaryl, or $R^3$ is forming an optionally substituted 3-, 4-, 5-, or 6-membered ring together with $R^2$ and the atoms to which they are connected, $R^4$ and $R^5$ are each independently selected from the group consisting of halogen, hydrogen, $-N(R^{4a})_2$, $-OR^{4a}$, $-(CH_2)_qC(O)OR^{4a}$, $-(CH_2)_qC(O)N(R^{4a})_2$, $-(CH_2)_qOC(O)R^{4a}$, $-(CH_2)_qNHC(O)R^{4a}$, an optionally substituted group selected from the group consisting of $(C_1-C_{18})$alkyl, $(C_1-C_{18})$alkyloxy$(C_1-C_{18})$alkyl, cyclo$(C_3-C_6)$alkyl, cyclo$(C_3-C_6)$alkyl$(C_1-C_{18})$alkyl, fused bicyclyl, heterocyclyl, heterocyclyl$(C_1-C_{18})$alkyl, aryl, aralkyl, heteroaryl, $(C_1-C_{18})$alkylaryl, aryl$(C_1-C_{18})$alkyl, heteroaryl$(C_1-C_{18})$alkyl, and $(C_1-C_{18})$alkylheteroaryl, $R^{2a}$, $R^{3a}$, and $R^{4a}$ are each optionally substituted groups independently selected from the group consisting of hydrogen, $(C_1-C_{10})$alkyl, $(C_2-C_{10})$alkenyl, $(C_2-C_{10})$alkynyl, $(C_1-C_{10})$alkoxy, $(C_1-C_{10})$alkyloxy$(C_1-C_{10})$alkyl, carboxy$(C_1-C_{10})$alkyl, carbonyl$(C_1-C_{10})$alkyl, cyclo$(C_3-C_6)$alkyl, cyclo$(C_3-C_6)$alkyl$(C_1-C_{10})$alkyl, fused bicyclyl, heterocyclyl, heterocyclyl$(C_1-C_{10})$alkyl, aryl, aralkyl, heteroaryl, $(C_1-C_{10})$alkylaryl, aryl$(C_1-C_{10})$alkyl, heteroaryl$(C_1-C_{10})$alkyl, and $(C_1-C_{10})$alkylheteroaryl, or wherein two identical $R^{2a}$, $R^{3a}$, or $R^{4a}$ together form an optionally substituted 4-, 5- or 6-membered heterocycle comprising the heteroatom to which both groups are connected; q is an integer selected from the group consisting of 1, 2, 3, 4, 5, 6, 7, 8, 9 and 10.

In the present context, (α-, β-, γ-, or δ-)lactam refers to the four different compounds: α-lactam, β-lactam, γ-lactam, and δ-lactam, respectively. In addition, (α-, β-, γ-, or δ-)lactone refers to the four different compounds: α-lactone, β-lactone, γ-lactone, and δ-lactone, respectively. The integer represented by q sets the number of methylene units in the chemical formula.

An even more specific embodiment of the present invention relates to the compound as described herein, wherein $R^{N2}$ is selected from the group consisting of hydrogen, methyl, ethyl, isopropyl, benzyl, trifluoromethyl, and trifluoroethyl, or $R^{N2}$ is forming an optionally substituted 3-, 4-, 5-, or 6-membered heterocycle together with $R^{2'}$ and the atoms to which they are connected, $R^2$ is selected from the group consisting of hydrogen, cyano, carboxy, carbamoyl, $-(CH_2)_qC(O)OR^{2a}$, $-(CH_2)_qC(O)N(R^{2a})_2$, $-(CH_2)_qOC(O)R^{2a}$, $-(CH_2)_qNHC(O)R^{2a}$, an optionally substituted group selected from the group consisting of $(C_1-C_{10})$alkyl, $(C_2-C_{10})$alkenyl, $(C_2-C_{10})$alkynyl, $(C_1-C_{10})$alkyloxy$(C_1-C_{10})$alkyl, cyclo$(C_3-C_6)$alkyl, heterocyclyl$(C_1-C_{10})$alkyl, aryl, heteroaryl, aryl$(C_1-C_{10})$alkyl, heteroaryl$(C_1-C_{10})$alkyl, radical of (β-, or γ-)lactam, and a radical of (β-, or γ-)lactone, or $R^2$ is forming an optionally substituted 3-, 4-, 5-, or 6-membered ring together with $R^3$ and the atoms to which they are connected, $R^{2'}$ is selected from the group consisting of hydrogen, cyano, carboxy, carbamoyl, $-(CH_2)_qC(O)OR^{2a}$, $-(CH_2)_qC(O)N(R^{2a})_2$, $-(CH_2)_qOC(O)R^{2a}$, $-(CH_2)_qNHC(O)R^{2a}$, an optionally substituted group selected from the group consisting of $(C_1-C_{10})$alkyl, $(C_2-C_{10})$alkenyl, $(C_2-C_{10})$alkynyl, $(C_1-C_{10})$alkyloxy$(C_1-C_{10})$alkyl, cyclo$(C_3-C_6)$alkyl, heterocyclyl$(C_1-C_{10})$alkyl, aryl, heteroaryl, aryl$(C_1-C_{10})$alkyl, heteroaryl$(C_1-C_{10})$alkyl, radical of β-, or γ-)lactam, and a radical of β-, or γ-)lactone, or $R^{2'}$ is forming an optionally substituted 3-, 4-, 5-, or 6-membered ring together with $R^3$ and the atoms to which they are connected, or $R^{2'}$ is forming an optionally substituted 3-, 4-, 5-, or 6-membered heterocycle together with $R^{2N}$ and the atoms to which they are connected, $R^3$ is selected from the group consisting of hydrogen, carboxy, carbamoyl, $-(CH_2)_qC(O)OR^{3a}$, $-(CH_2)_qC(O)N(R^{3a})_2$, $-(CH_2)_qOC(O)R^{3a}$, $-(CH_2)_qNHC(O)R^{3a}$, an optionally substituted group selected from the group consisting of $(C_1-C_{10})$alkyl, $(C_1-C_{10})$alkyloxy$(C_1-C_{10})$alkyl, cyclo$(C_3-C_6)$alkyl, heterocyclyl$(C_1-C_{10})$alkyl, aryl, heteroaryl, aryl$(C_1-C_{10})$alkyl, heteroaryl$(C_1-C_{10})$alkyl, or $R^3$ is forming an optionally substituted 3-, 4-, 5-, or 6-membered ring together with $R^2$ and the atoms to which they are connected, $R^4$ is selected from the group consisting of halogen, hydrogen, $-N(R^{4a})_2$, $-OR^{4a}$, $-(CH_2)_qC(O)OR^{4a}$, $-(CH_2)_qC(O)N(R^{4a})_2$, $-(CH_2)_qOC(O)R^{4a}$, $-(CH_2)_qNHC(O)R^{4a}$, an optionally substituted group selected from the group consisting of $(C_1-C_{18})$alkyl, $(C_1-C_{18})$alkyloxy$(C_1-C_{18})$alkyl, cyclo$(C_3-C_6)$alkyl$(C_1-C_{18})$alkyl, heterocyclyl$(C_1-C_{18})$alkyl, aryl, heteroaryl, aryl$(C_1-C_{18})$alkyl, and heteroaryl$(C_1-C_{18})$alkyl, $R^5$ is selected from the group consisting of halogen, hydrogen, $-N(R^{4a})_2$, $-OR^{4a}$, $-(CH_2)_qC(O)OR^{4a}$, $-(CH_2)_qC(O)N(R^{4a})_2$, $-(CH_2)_qOC(O)R^{4a}$, $-(CH_2)_qNHC(O)R^{4a}$, an optionally substituted group selected from the group consisting of $(C_1-C_{18})$alkyl, $(C_1-C_{18})$alkyloxy$(C_1-C_{18})$alkyl, cyclo$(C_3-C_6)$alkyl$(C_1-C_{18})$alkyl, heterocyclyl$(C_1-C_{18})$alkyl, aryl, heteroaryl, aryl$(C_1-C_{18})$alkyl, and heteroaryl$(C_1-C_{18})$alkyl, Red is selected from the group consisting of hydrogen, $(C_1-C_{10})$alkyl, $(C_2-C_{10})$alkenyl, $(C_1-C_{10})$alkoxy, $(C_2-C_{10})$alkynyl, carboxy$(C_1-C_{10})$alkyl, cyclo$(C_3-C_6)$alkyl, cyclo$(C_3-C_6)$alkyl$(C_1-C_{10})$alkyl, fused bicyclyl, heterocyclyl$(C_1-C_{10})$alkyl, aralkyl, aryl$(C_1-C_{10})$alkyl, and heteroaryl$(C_1-C_{10})$alkyl, or Red is forming an optionally substituted 4-, 5- or 6-membered heterocycle together with another Red which heterocycle comprises the heteroatom to which both groups are connected; Ria is selected from the group consisting of $(C_1-C_{10})$alkyl, $(C_2-C_{10})$alkenyl, $(C_2-C_{10})$alkynyl, carboxy$(C_1-C_{10})$alkyl, cyclo$(C_3-C_6)$alkyl$(C_1-C_{10})$alkyl, fused bicyclyl, heterocyclyl$(C_1-C_{10})$alkyl, aralkyl, aryl$(C_1-C_{10})$alkyl, and heteroaryl$(C_1-C_{10})$alkyl, or $R^{3a}$ is forming an optionally substituted 4-, 5- or 6-membered heterocycle together with another $R^{3a}$ which heterocycle comprises the heteroatom to which both groups are connected; $R^{4a}$ is selected from the group consisting of $(C_1-C_{10})$alkyl, $(C_2-C_{10})$alkenyl, $(C_2-C_{10})$alkynyl, carboxy$(C_1-C_{10})$alkyl, cyclo$(C_3-C_6)$alkyl$(C_1-C_{10})$alkyl, fused bicyclyl, heterocyclyl$(C_1-C_{10})$alkyl, aralkyl, aryl$(C_1-C_{10})$alkyl, and heteroaryl$(C_1-C_{10})$alkyl, or $R^{4a}$ is forming an optionally substituted 4-, 5- or 6-membered heterocycle together with another $R^{4a}$ which heterocycle comprises the heteroatom to which both groups are connected; q is an integer selected from the group consisting of 1, 2, 3, 4, 5, 6, 7, 8, 9 and 10.

Stability and flexibility of the molecules can be influenced by optionally introducing one or more additional rings on the sides of the macrocycle. Especially preferred are the rings wherein the ring structure is composed of 5 to 6 atoms, because these are normally regarded as being particularly stable.

The rings on the sides of the macrocycle may be located in two different positions. In a first position the rings are formed between $R^{N2}$ and $R^{2'}$ whereby the nitrogen atom and carbon atom to which they are connected take part in forming the ring. Any ring formed in the first position must therefore be selected from the group of heterocycles comprising nitrogen.

Thus, an embodiment of the present invention relates to the compound as described herein, wherein the optionally substituted 3-, 4-, 5-, or 6-membered heterocycle formed by $R^{N2}$ and $R^{2'}$ and the atoms to which they are connected is an optionally substituted 5- or 6-membered heterocycle. A more specific embodiment of the present invention relates to the compound as described herein, wherein the optionally substituted 5-, or 6-membered heterocycle formed by $R^{N2}$ and $R^{2'}$ and the atoms to which they are connected is selected from the group consisting of (γ-, or δ-)lactam, pyrrolidine, pyrroline, pyrazolidine, imidazolidine, pyrazoline, imidazoline, oxazolidone, hydantoin, piperidine, piperazine, morpholine, thiomorpholine, and diazinane.

In a second position, the rings are formed between $R^2$ and $R^3$ whereby the two carbon atoms, to which they are connected, take part in forming the ring.

Thus, an embodiment of the present invention relates to the compound as described herein, wherein the optionally substituted 3-, 4-, 5-, or 6-membered ring formed by $R^2$ and $R^3$ and the atoms to which they are connected is an optionally substituted 5- or 6-membered ring. A particularly preferred embodiment of the present invention relates to the compound as described herein, wherein the optionally substituted 5-, or 6-membered ring formed by $R^2$ and $R^3$ and the atoms to which they are connected is selected from the group consisting of (γ-, or δ-)lactam, (γ-, or δ-)lactone, cyclopentane, pyrrolidine, pyrroline, pyrazolidine, imidazolidine, pyrazoline, imidazoline, tetrahydrofuran, dioxolane, tetrahydrothiophene, oxathiolane, sulfolane, succinimide, oxazolidone, cyclohexane, piperidine, piperazine, tetrahydropyran, dioxane, thiane, dithiane, morpholine, thiomorpholine, and diazinane.

In some embodiments, a side-group such as $R^2$ may be selected to comprise an amide, such as —$(CH_2)_qC(O)N(R^{2a})_2$. In this particular case, the nitrogen atoms is connected to a $R^{2a}$-group and another $R^{2a}$-group, which two R-groups are thus "identical".

Two such "identical" R-groups may optionally form a heterocycle comprising the nitrogen atom to which they are bound. Especially preferred are the heterocycles wherein the ring structure is composed of 5 to 6 atoms, because these are normally regarded as being particularly stable. Thus, a special embodiment of the present invention relates to the compound as described herein, wherein the optionally substituted 4-, 5- or 6-membered heterocycle formed by two identical $R^{1a}$, $R^{2a}$, $R^{3a}$, or $R^{4a}$ and the heteroatom to which both groups are connected is an optionally substituted 5- or 6-membered heterocycle. A further embodiment of the present invention relates to the compound as described herein, wherein the optionally substituted 5- or 6-membered heterocycle formed by two identical $R^{1a}$, $R^{2a}$, $R^{3a}$, or $R^{4a}$ and the heteroatom to which both groups are connected is selected from the group consisting of piperidine, pyrroline, pyrrole, pyrazolidine, imidazolidine, pyrazoline, imidazoline, pyrazole, imidazole, triazole, tetrazole, thiazolidinedione, succinimide, oxazolidone, hydantoin, piperidine, piperazine, morpholine, oxazine, thiomorpholine, thiazine, thymine, and uracil.

In some embodiments, a side-group (such as $R^{N1}$) may be selected from a group of substituents, which substituents may optionally be further substituted with small active chemical groups. Therefore, an embodiment of the present invention relates to the compound as described herein, wherein the optional substituents on $R^{N1}$, $R^{N2}$, $R^1$, $R^2$, $R^{2'}$, $R^3$, $R^4$, $R^5$, $R^{1a}$, $R^{2a}$, $R^{3a}$, and $R^{4a}$ are each independently selected from the group consisting of halogen, methyl, silyl, azido, amino, nitro, cyano, hydroxy, sulfanyl, carboxy, and carbamoyl. In the present context, a halogen is selected from the group consisting of bromo, chloro, fluoro, and iodo.

In some embodiments, the optional substituents on $R^{N1}$ are selected from the group consisting of halogen, amino, hydroxy, sulfanyl, carboxy, and carbamoyl; the optional substituents on $R^{N2}$ are selected from halogen, amino, hydroxy, sulfanyl, carboxy, and carbamoyl; the optional substituents on $R^1$ are selected from halogen, amino, hydroxy, sulfanyl, carboxy, and carbamoyl; the optional substituents on $R^2$ are selected from halogen, amino, hydroxy, sulfanyl, carboxy, and carbamoyl; the optional substituents on $R^{2'}$ are selected from halogen, amino, hydroxy, sulfanyl, carboxy, and carbamoyl; the optional substituents on $R^3$ are selected from halogen, amino, hydroxy, sulfanyl, carboxy, and carbamoyl; the optional substituents on $R^4$ are selected from halogen, amino, hydroxy, sulfanyl, carboxy, and carbamoyl; the optional substituents on $R^5$ are selected halogen, amino, hydroxy, sulfanyl, carboxy, and carbamoyl; the optional substituents on $R^{1a}$ are selected from halogen, amino, hydroxy, sulfanyl, carboxy, and carbamoyl; the optional substituents on $R^{2a}$ are selected from halogen, amino, hydroxy, sulfanyl, carboxy, and carbamoyl; the optional substituents on $R^{3a}$ are selected from halogen, amino, hydroxy, sulfanyl, carboxy, and carbamoyl; the optional substituents on $R^{4a}$ are selected from halogen, methyl, amino, hydroxy, sulfanyl, carboxy, and carbamoyl.

In some particular embodiments, any of the formed rings or heterocycles may be further substituted with small active chemical groups. Thus, an embodiment of the present invention relates to the compound as described herein, wherein the optional substituents on the rings and the heterocycles are a number of 1 to 3 substituents that are each independently selected from the group consisting of halogen, methyl, silyl, azido, amino, nitro, cyano, hydroxy, sulfanyl, carboxy, carbamoyl, and carbonyl.

An even more preferred embodiment of the present invention relates to the compound as described herein, wherein the compound is represented by formula (2a):

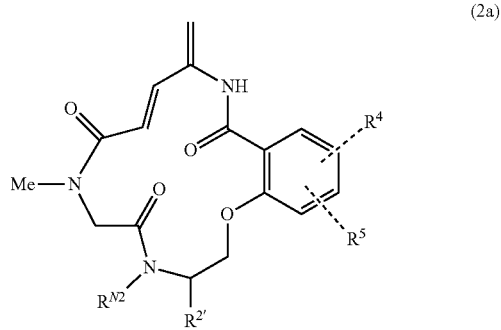

(2a)

Wherein, $R^{N2}$ is hydrogen and $R^{2'}$ is selected from the group consisting of hydrogen, —$(CH_2)_qC(O)OR^{2a}$, —$(CH_2)_qC(O)N(R^{2a})_2$, and —$(CH_2)_qNHC(O)R^{2a}$, or $R^{2'}$ is forming an optionally substituted 5- or 6-membered heterocycle together with $R^{2N}$ which heterocycle is selected from the group consisting of (γ-, or δ-)lactam, pyrrolidine, pyrroline, pyrazolidine, imidazolidine, pyrazoline, imidazoline, oxazolidone, hydantoin, piperidine, piperazine, morpholine, thiomorpholine, and diazinane; q is an integer selected from the group consisting of 1, 2, 3, 4, 5, 6, 7, 8, 9 and 10; $R^{2a}$ is independently selected from the group consisting of hydrogen, $(C_1$-$C_{10})$alkyl, $(C_2$-$C_{10})$alkenyl, $(C_1$-$C_{10})$alkoxy, $(C_2$-$C_{10})$alkynyl, carboxy$(C_1$-$C_{10})$alkyl, cyclo ($C_3$-$C_6$)alkyl, cyclo($C_3$-$C_6$)alkyl($C_1$-$C_{10}$)alkyl, fused bicyclyl, heterocyclyl($C_1$-$C_{10}$)alkyl, aralkyl, aryl($C_1$-$C_{10}$)alkyl, and heteroaryl($C_1$-$C_{10}$)alkyl, or Red is forming an optionally substituted 4-, 5- or 6-membered heterocycle together with another Red which heterocycle comprises the heteroatom to which both groups are connected and is selected from the group consisting of piperidine, pyrroline, pyrrole, pyrazolidine, imidazolidine, pyrazoline, imidazoline, pyrazole, imidazole, triazole, tetrazole, thiazolidinedione, succinimide, oxazolidone, hydantoin, piperidine, piperazine, morpholine, oxazine, thiomorpholine, thiazine, thymine, and uracil;

$R^4$ and $R^5$ are independently selected from the group consisting of hydrogen, an optionally substituted group selected from the group consisting of ($C_1$-$C_{18}$)alkyl, ($C_1$-$C_{18}$)alkyloxy($C_1$-$C_{18}$)alkyl, cyclo($C_3$-$C_6$)alkyl($C_1$-$C_{18}$)alkyl, heterocyclyl($C_1$-$C_{18}$)alkyl, aryl, heteroaryl, aryl($C_1$-$C_{18}$)alkyl, and heteroaryl($C_1$-$C_{18}$)alkyl; the optional substituents are as defined by the embodiments as described herein.

A particularly preferred embodiment of the present invention relates to the compound as described herein, wherein $R^{N2}$ is hydrogen and $R^{2'}$ is selected from the group consisting of hydrogen, $-(CH_2)_qC(O)OR^{2a}$, $-(CH_2)_qC(O)N(R^{2a})_2$, and $-(CH_2)_qNHC(O)R^{2a}$, or $R^{2'}$ together with $R^{2N}$ form an optionally substituted pyrrolidine heterocycle; q is an integer selected from the group consisting of 1, 2, 3, 4, 5 and 6; Red is independently selected from the group consisting of hydrogen, ($C_1$-$C_{10}$)alkyl, ($C_2$-$C_{10}$)alkenyl, ($C_1$-$C_{10}$)alkoxy, ($C_2$-$C_{10}$)alkynyl and cyclo($C_3$-$C_6$)alkyl, or Red together with another Red form an optionally substituted morpholine heterocycle; $R^4$ and $R^5$ are independently selected from the group consisting of hydrogen, and ($C_1$-$C_{18}$)alkyl; the optional substituents for the heterocycles are a number of 1 to 3 substituents that are each independently selected from the group consisting of chloro, fluoro, bromo, and iodo, preferably fluoro.

In a very specific embodiment of the present invention relating to the compound as described herein, the ($C_1$-$C_{10}$)alkyl is a radical selected from the group consisting of methyl, ethyl, propyl, isopropyl, butyl, tert-butyl, pentyl, hexyl, heptyl, octyl, nonyl, and decyl, preferably methyl.

In another very specific embodiment of the present invention relating to the compound as described herein, the cyclo($C_3$-$C_6$)alkyl is a radical selected from the group consisting of cyclopropyl, cyclobutyl, cyclopentyl, and cyclohexyl.

Another particular embodiment of the present invention relates to the compound as described herein, wherein the ($C_1$-$C_{10}$)alkoxy is a radical selected from the group consisting of methoxy, ethoxy, propoxy, isopropoxy, butyloxy, tert-butyloxy, pentyloxy, hexyloxy, heptyloxy, octyloxy, nonyloxy, and decyloxy, preferably tert-butyloxy.

Another particular embodiment of the present invention relates to the compound as described herein, wherein the ($C_2$-$C_{10}$)alkynyl is a radical selected from the group consisting of ethynyl, propargyl, butynyl, pentynyl, and hexynyl, preferably propargyl.

A most preferred and specific embodiment of the present invention relates to the compound as described herein, wherein the compound is selected from the group consisting of:

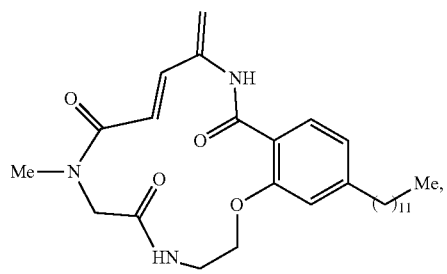

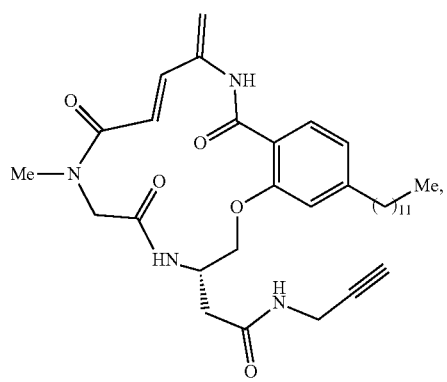

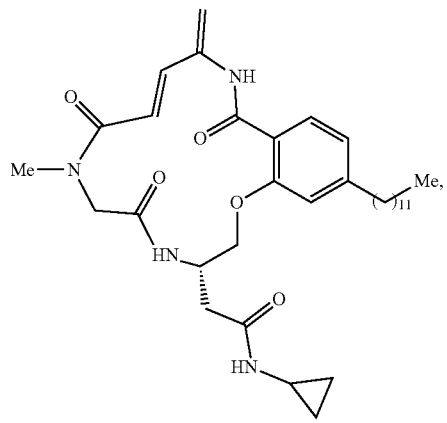

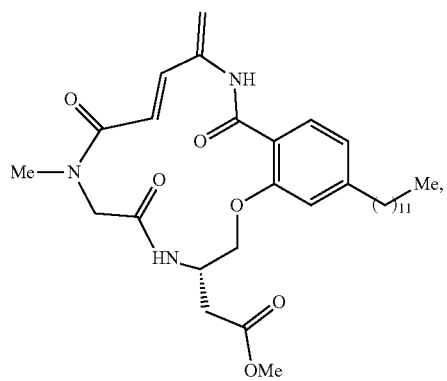

-continued

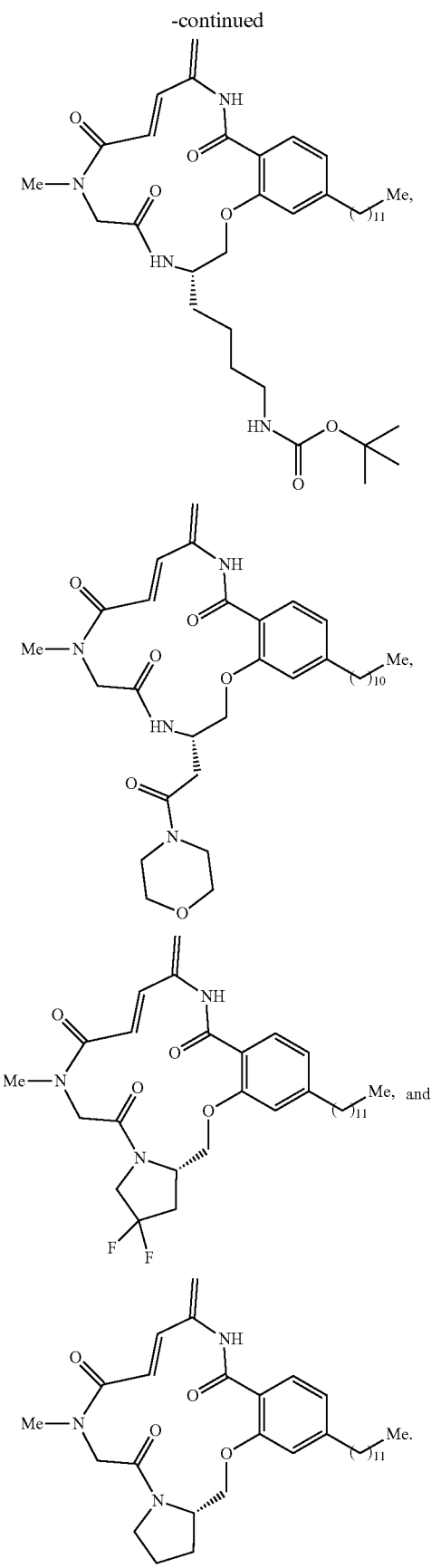

An embodiment of the present invention relates to the compound as described herein, wherein the compound is represented by formula (3)

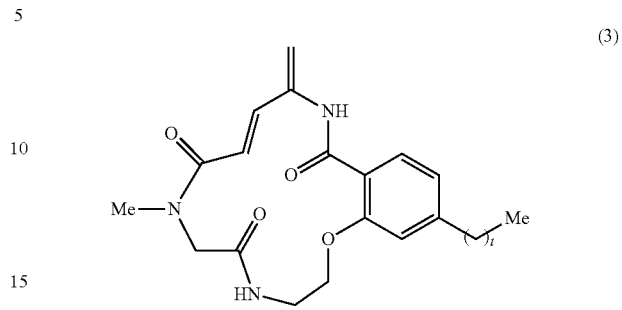

wherein,
t is an integer between 1 and 15.
Some embodiments the present invention relates to a compounds, wherein t is an integer of 1 to 15, 3 to 15, 5 to 15, 10 to 15, most preferably 10 to 14.

The name, PH466, relates to a compound of the present invention as described herein, wherein the compound is represented by formula (4)

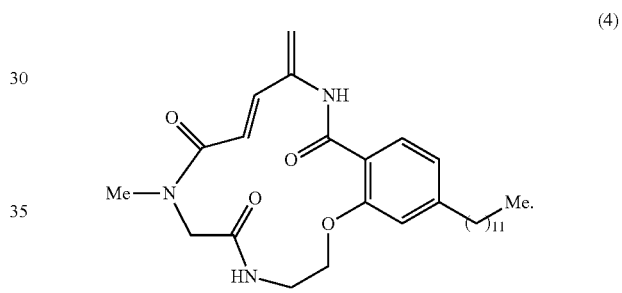

The compounds of the present invention possess hypoxia selective toxicity and are therefore suitable for treatment of cancer cells in hypoxic cancerous tissues.

Another aspect of the present invention therefore relates to a pharmaceutical composition comprising the compound described herein, or a pharmaceutically acceptable salt thereof. Furthermore, an embodiment of the present invention relates to the pharmaceutical composition as described herein, wherein the pharmaceutical composition further comprises a pharmaceutically acceptable carrier, diluent, excipient and/or adjuvant.

An embodiment of the present invention relates to the pharmaceutical composition as described herein, wherein the pharmaceutical composition further comprises one or more additional therapeutic agents.

Yet another aspect of the present invention is the compound described herein or a pharmaceutical composition described herein, for use as a medicament.

In a further aspect, the present invention provides a compound or pharmaceutical composition as described herein, for use in the treatment of cancer.

In one embodiment of the present invention, the cancer is a cancer with hypoxic or hypoxia-like cancer cells.

In another embodiment, the present invention provides the compound or pharmaceutical composition described herein for use in the treatment of cancer that selectively kills hypoxic cancer cells, such that the hypoxic cells in the subject are depleted.

In yet another embodiment, the present invention provides the compound or pharmaceutical composition described herein for use in the treatment of a cancer within of a subject by administering to the subject the compound of the present invention that selectively kills hypoxic or hypoxia-like cancer cells, such that the hypoxic cells in the subject are depleted.

In a particular embodiment, the present invention provides the compound or pharmaceutical composition described herein for use in the treatment of cancer that selectively target and deplete hypoxic cells of tumors which is active only under hypoxic conditions, thereby reducing or eliminating the undesirable side effects associated with existing therapies.

Still another aspect of the present invention is the compound described herein or a pharmaceutical composition described herein, for use in the treatment of cancer. Thus, a special embodiment of the present invention relates to the compound for use as described herein, wherein the cancer is selected from the group consisting of leukemia, bladder cancer, bone and soft tissue cancer, bone cancer, ocular cancer, fallopian tube cancer, gastric cancer, head and neck cancer, kidney cancer, liver cancer, central nervous system cancer, thyroid cancer, uterus cancer, vulvar cancer, vaginal cancer, prostate cancer, colon cancer, breast cancer, lung cancer, oral cancer, pancreatic cancer, and ovarian cancer.

A more specific embodiment of the present invention relates to the compound for use as described herein, wherein the cancer is selected from the group consisting of osteosarcoma, chondrosarcoma, Erwing sarcoma, hemangioendothelioma, angiosarcoma, fibrosarcoma, chordoma, adamantinoma, liposarcoma, leiomyosarcoma, malignant peripheral nerve sheath tumor, rhabdomyosarcoma, synovial sarcoma, solitary fibrous tumor, dermatofibrosarcoma protuberans, myofibroblastic tumor, myxofibrosarcoma, fibromyxoid sarcoma, giant cell tumor of soft tissue, glomus tumor, gastrointestinal stromal tumor, triton tumor, granular cell tumor, myoepithelial carcinoma, epithelioid sarcoma, alveolar soft part sarcoma, clear cell sarcoma of soft tissue, small round cell tumor, rhabdoid tumor, perivascular epithelioid cell tumor, intimal sarcoma, spindle cell sarcoma, pleomorphic sarcoma, round cell sarcoma, adenocarcinoma, squamous cell carcinoma, anaplastic carcinoma, large cell carcinoma, small cell carcinoma, spindle cell carcinoma, giant cell carcinoma, sarcomatoid carcinoma, pleomorphic carcinoma, hepatocellular carcinoma, Hodgkin lymphoma, Non-Hodgkin lymphomas, and EBV-positive Hodgkin lymphomas.

In a further aspect, the present invention provides a method for treating cancer within a subject by administering to the subject a compound of the present invention.

In one embodiment, the present invention provides a method for treating a cancer within of a subject by administering to the subject the compound of the present invention that selectively kills hypoxic or hypoxia-like cancer cells, such that the hypoxic cells in the subject are depleted.

In a particular embodiment, the method of the present invention selectively target and deplete hypoxic cells of tumors using the compound of the present invention which is active only under hypoxic conditions, thereby reducing or eliminating the undesirable side effects associated with existing therapies.

In one embodiment of the present invention relates to a method of treatment cancer, wherein the cancer is selected from the group consisting of leukemia, bladder cancer, bone and soft tissue cancer, bone cancer, ocular cancer, fallopian tube cancer, gastric cancer, head and neck cancer, kidney cancer, liver cancer, central nervous system cancer, thyroid cancer, uterus cancer, vulvar cancer, vaginal cancer, prostate cancer, colon cancer, breast cancer, lung cancer, oral cancer, pancreatic cancer, and ovarian cancer.

The present invention is particularly useful method for the treatment of a variety of solid malignancies and cancers which have metastasized to the bone marrow such as osteosarcoma, chondrosarcoma, Erwing sarcoma, hemangioendothelioma, angiosarcoma, fibrosarcoma, chordoma, adamantinoma, liposarcoma, leiomyosarcoma, malignant peripheral nerve sheath tumor, rhabdomyosarcoma, synovial sarcoma, solitary fibrous tumor, dermatofibrosarcoma protuberans, myofibroblastic tumor, myxofibrosarcoma, fibromyxoid sarcoma, giant cell tumor of soft tissue, glomus tumor, gastrointestinal stromal tumor, triton tumor, granular cell tumor, myoepithelial carcinoma, epithelioid sarcoma, alveolar soft part sarcoma, clear cell sarcoma of soft tissue, small round cell tumor, rhabdoid tumor, perivascular epithelioid cell tumor, intimal sarcoma, spindle cell sarcoma, pleomorphic sarcoma, round cell sarcoma, adenocarcinoma, squamous cell carcinoma, anaplastic carcinoma, large cell carcinoma, small cell carcinoma, spindle cell carcinoma, giant cell carcinoma, sarcomatoid carcinoma, pleomorphic carcinoma, hepatocellular carcinoma, Hodgkin lymphoma, Non-Hodgkin lymphomas, and EBV-positive Hodgkin lymphomas.

The hypoxia-selective toxins or APD-containing macrocycles of the present invention may be administered via any suitable route of administration. As will be appreciated by the skilled person, the best route for in vivo administration may vary depending upon the patient or desired result. Suitable routes of administration for agents of the present invention include, but are not limited to, intravenous, intramuscular, intradermal, intraperitoneal, subcutaneous, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion.

The hypoxia-selective toxins or APD-containing macrocycles of the present invention are preferably administered to a subject in a suitable pharmacological form (e.g., as a pharmaceutical composition). For example, the compound can be formulated with carriers and other pharmaceutically acceptable compounds, that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid.

For parenteral administration, it is especially advantageous to formulate the compound of the present invention in dosage unit form for ease of administration and uniformity of dosage. Dosage unit form as used herein refers to physically discrete units suited as unitary dosages for the particular individual to be treated; each unit containing a predetermined quantity of active compound calculated to so produce the desired therapeutic effect in association with the required pharmaceutical carrier.

When administered parenterally, a compound of the present invention will normally be formulated in a unit dosage injectable form (solution, suspension, emulsion) with a pharmaceutically acceptable vehicle. Such vehicles are typically nontoxic and non-therapeutic. Examples of such vehicles are water, aqueous vehicles such as saline, Ringer's solution, dextrose solution, and Hank's solution and non-aqueous vehicles such as fixed oils (e.g., corn, cottonseed, peanut and sesame), ethyl oleate, and isopropyl myristate. The vehicle may contain minor amounts of additives such as substances that enhance solubility, isotonicity, and chemical stability, e.g., antioxidants, buffers, and preservatives.

The hypoxia-selective toxins or APD-containing macrocycles of the present invention are administered to a subject in an amount and for a sufficient time period to achieve selective depletion of hypoxic cells. The appropriate dosage of the agent will depend on factors such as the disease state, severity of the condition to be alleviated, age, sex, and weight of the individual. Adjustment of dosage regimens for known chemotherapeutics is well within the routine skill of the art. It is to be further understood that for any particular subject, specific dosage regimens should be adjusted over time according to the individual need and the professional judgment of the person administering or supervising the administration of the compositions. The agent may be administered once, or may be divided into a number of smaller doses to be administered at varying intervals of time.

The hypoxia-selective toxins or APD-containing macrocycles of the present invention can be administered alone or in combination with one or more other therapeutic or pharmaceutical agents (e.g., prior to or following the administration of donor bone marrow, donor cytokine mobilized peripheral blood, or donor umbilical cord blood). For example, in one embodiment of the invention, the agent may be combined with a short-term immune modulating agent, such as a T cell-depleting antibody, which functions to deplete or inactivate immune cells in the host.

The hypoxia-selective toxins or APD-containing macrocycles of the present invention can also be administered in combination with one or more myeloablative therapies, such as radiation therapy or chemotherapy. The agents may also be administered in combination with one or more chemotherapeutic agents. Such adjunctive therapies may be administered prior to, subsequent to, or in conjunction with administration of the hypoxia-activated agent. Particular chemotherapeutic agents include, but are not limited to, All-trans retinoic acid, Aminoglutethimide, Azacitidine, Azathioprine, Bleomycin (Blenoxane), Busulfan (Myeleran), Carboplatin, Carboplatinuin (Paraplatin), Carmustine (BCNU), Capecitabine, CCNU (Lomustine), Chlorambucil (Leukeran), 2-Cholrodeoxyadenosine (2-CDA; Cladribine, Leustatin), Cis-platinum (Platinol), Cisplatin (cis-DDP), Cisplatin bleomycin sulfate, Chlorambucil, Cyclophosphamide (Cytoxanl CTX), Cyclophosphamide hydroxyurea, Cytarabine (Ara-C; cytosine arabinoside), Daunorubicin (Cerubidine), Dacarbazine (DTIC; dimethyltriazenoimidazolecarboxamide), Dactinomycin (actinomycin D), Daunorubicin (daunomycin; rubidomycin), Diethylstilbestrol, Docetaxel (Taxotere), Doxifluridine, Doxolubicin (Adriamycin), Epirubicin, Ethinyl estradoil, Etopaside (VP-16, VePesid), Fluorouracil (5-Fu; Floxuridine, fluorodeoxyuridine; FUdR), Fludarabine (Fludara), Flutamide, Fluoxymesterone, Gemcitabine (Gemzar), Herceptin (Trastuzumab; anti-HER 2 monoclonal antibody), Hydroxyurea (Hydrea), Hydroxyprogesterone caproate, Idarubicin, Ifosfamide (Ifex), Interferon alpha, Irinotecan (CPT-11), L-Asparaginase, Leuoprolide, Mechlorethamine, Medroxyprogesterone acetate, Megestrol acetate, Melphelan (Allceran), Mercaptopurine (6-mercaptopurine; 6-MP), Methotrexate (MTX; arnethopterin), Mitomycin (mitomycin C), Mitotane (o,p'-DDD), Mitoxantrone (Novantrone), Oxaliplatin, Paclitaxel (Taxol), Pemetrexed, Pentostatin (2-deoxycoformycin), Plicamycin (mithramycin), Prednisone, Procarbazine (Matulane; N-methylhydrazine, MIH), Rituxin (Rituximap), Semustine (Methyl-CCNU), Streptozocin, Tamoxifen, Teniposide, Tertiposide, Testosterone propionate, Thioguanine (6-thioguanine; TG), Thiotepa, Tomudex (Raltitrexed), Topotecan (Hycamtin; (S)-10-[(dimethylamino) methyl]-4-ethyl-4,9-dihydroxy-1H-pyrano[3', 4'), Treosulfan (Ovastat), Valrubicin, Vinblastine (VLB; Velban), Vincristine (Oncovin), Vindesine, and Vinorelbine Navelbine).

An alternative embodiment of the present invention relates to the compound as described herein, wherein the compound is represented by formula (5)

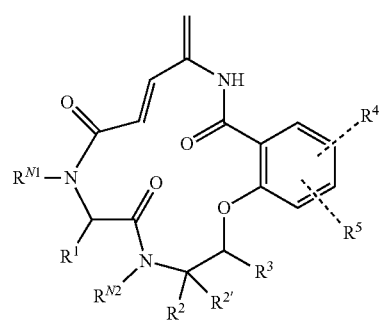

(5)

each of $R^{N1}$, $R^{N2}$, $R^1$, $R^2$, $R^{2'}$, $R^3$, $R^4$, and $R^5$ is defined anywhere else herein.

Another embodiment of the present invention relates to the compound as described herein, wherein the compound is represented by formula (6)

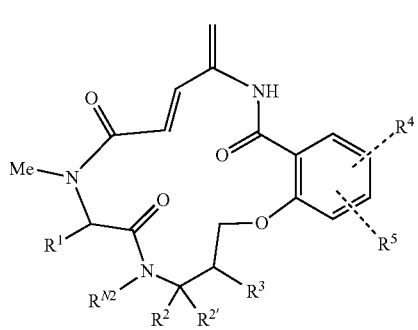

(6)

each of $R^{N1}$, $R^{N2}$, $R^1$, $R^2$, $R^{2'}$, $R^3$, $R^4$, and $R^5$ is defined anywhere else herein.

A further embodiment of the present invention relates to the compound as described herein, wherein the compound is represented by formula (7)

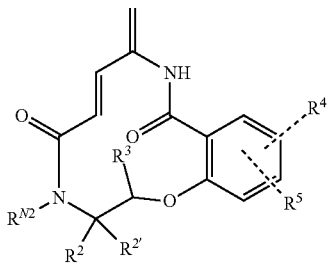

(7)

each of $R^{N2}$, $R^2$, $R^{2'}$, $R^3$, $R^4$, and $R^5$ is defined anywhere else herein.

It should be noted that embodiments and features described in the context of one of the aspects of the present invention also apply to the other aspects of the invention.

All patent and non-patent references cited in the present application, are hereby incorporated by reference in their entirety.

The invention will now be described in further details in the following non-limiting examples.

EXAMPLES

Example 1—Materials and Methods for Synthesis

Materials List (Non-Exhaustive)

Di-tert-butyl pyrocarbonate (Boc₂O)
tert-butoxycarbonyl-N-methylglycine (Boc-Sar-OH)
1-Hydroxybenzotriazole hydrate (HOBt-hydrate)
N-(3-Dimethylaminopropyl)-N'-ethylcarbodiimide hydrochloride (EDCI)
N,N-Diisopropylethylamine (DIPEA)
N—Z-L-Serine methyl ester
Sarcosine tert-butyl ester hydrochloride
3-(Diethoxyphosphoryloxy)-1,2,3-benzotriazin-4(3H)-one (DEPBT)
N,N,N',N'-Tetramethylethylenediamine (TMEDA)
2-(1H-Benzotriazole-1-yl)-1,1,3,3-tetramethylaminium tetrafluoroborate (TBTU)
Zinc trifluoromethanesulfonate (Zn(OTf)₂)
Tetrabutylammonium fluoride (TBAF)
Ethyl acetate (EtOAc)
N,N'-Disuccinimidyl carbonate (DSC)
Dess-Martin periodinane (DMP)
tetrakis(triphenylphosphine)palladium
2-hydroxy-bromobenzoic acid
N-Boc-ethanolamine
HCl solution, 4 M in 1,4-dioxane
N-Boc-L-prolinol
Methyliminodiacetic acid
(S)-Benzyl tert-butyl (6-hydroxyhexane-1,5-diyl)dicarbamate
Diethylazodicarboxylate, 40% solution in toluene
N,N,N',N'-Tetramethyl-O-(benzotriazol-1-yl)uronium tetrafluoroborate
Diethylphosphonoacetic acid
Cuprous iodide
Bis(triphenylphosphine)palladium(II) dichloride
(1-[Bis(dimethylamino)methylene]-1H-1,2,3-triazolo[4,5-b]pyridinium 3-oxide hexafluorophosphate, HATU
Propargylamine
10% Palladium on carbon support
2-Propanol (I-PrOH)
1-Hydroxybenzotriazole hydrate (HOBt-hydrate)

General Procedures

Dichloromethane, acetonitrile, tetrahydrofuran and toluene were dried over aluminum oxide using an MBraun SPS-800 solvent purification system and stored over 4 Å molecular sieves under an argon atmosphere. Dimethylformamide, dimethylsulfoxide and methanol were purchased as anhydrous from commercial vendors. Water content of appropriate organic solvents was monitored using a Karl-Fischer titration apparatus. Chemical reagents were used as supplied from commercial vendors unless stated otherwise. TLC analysis was performed on Merck Kieselgel 60 F254 silica coated aluminum foil. TLC plates were visualized using UV-illumination at 254 nm or staining with ceric ammonium molybdate, ninhydrin or potassium permanganate stain. Ceric ammonium molybdate stain: $(NH_4)_6Mo_7O_{24} \cdot 4H_2O$ (10 g): Ceric ammonium sulfate (4 g), 10% $H_2SO_4$ (aq., 400 mL). Ninhydrin stain: Ninhydrin (12 g), AcOH (12 mL), n-butanol (400 mL). $KMnO_4$ stain: $KMnO_4$ (5.0 g), 5% NaOH (aq., 8.3 mL) and $K_2CO_3$ (33.3 g) in water (500 mL). Standard purification procedures of tertiary amine bases were performed as described elsewhere. Flash column chromatography on silica gel was performed using an Interchim Puriflash XS 420 system, adapted to accept disposable 15 mL fraction tubes, using pre-packed 30 μm pore size Interchim silica gel columns (PF-30SIHP series). Manual flash column chromatography was performed using silica gel 60 (230-400 mesh particle size). Infrared spectroscopy (IR) was performed on a PerkinElmer Spectrum Two™ U-ATR instrument by depositing compounds from solution or neat, as indicated. High resolution mass spectrometry (HRMS) was conducted on a Bruker Daltonics MicrOTOF time-of-flight spectrometer under electrospray ionization either in positive or negative mode with internal calibration using sodium formate clusters. Nuclear magnetic resonance (NMR) spectroscopy was performed using a Varian Mercury 400 MHz spectrometer or a Bruker BioSpin GmbH 400 MHz spectrometer, with respective resonance for $^{13}C$ and $^1H$ at 400 MHz and 101 MHz. Spectra were calibrated to the residual solvent peak. Standard abbreviations for signal multiplicities are used in the experimental reports.

Example 2—Synthesis of PH466

Figure 2:
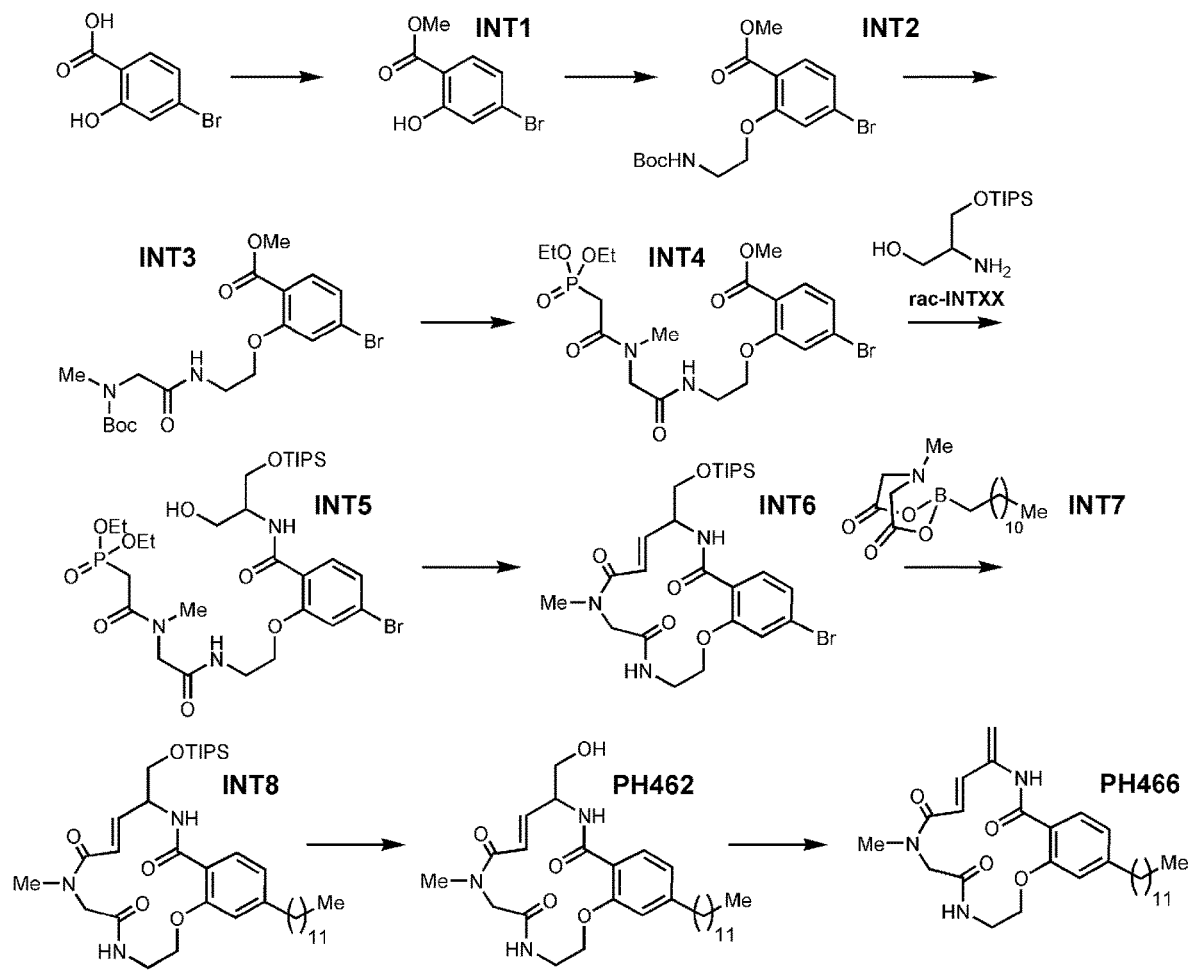
FIG. 2 shows the synthetic route to PH466.

The synthesis pathway for obtaining PH466 is depicted in FIG. 2. Detailed descriptions for the synthesis of PH466 and each of the nine intermediates (INT) are given in the following subsections:

Methyl 4-bromo-2-hydroxybenzoate (INT1)

A solution of 2-hydroxy-4-bromobenzoic acid (4.57 g, 1.0 equiv., 20.0 mmol) in anhydrous MeOH (60 mL) was transferred to a flame-dried one-necked flask (100 mL) equipped with a stirrer bar. Subsequently, addition of concentrated sulfuric acid (98.5%, 2.2 mL) was performed. The mixture was stirred at reflux for 19 hours before being concentrated. After evaporation of the solvent, addition of EtOAc (60 mL) and careful addition of saturated aqueous $NaHCO_3$ (80 mL) was made, and the phases were separated. The aqueous phase was extracted with EtOAc (3×50 mL) and the organic phase was washed with brine (100 mL), before being dried over sodium sulphate, filtered and concentrated to yield a dark brown crude isolate. The crude material was purified by flash column chromatography on silica gel using an eluent system of Heptane/EtOAc 90:10 to afford the desired product as colorless needles (4.31 g, 18.7 mmol, 93%). TLC (Heptane:EtOAc, 90:10 v/v, UV, KMnO$_4$): R$_f$=0.38; $^1$H NMR (400 MHz, CDCl$_3$): δ 10.83 (s, 1H), 7.68 (d, J=8.5 Hz, 1H), 7.18 (d, J=1.9 Hz, 1H), 7.02 (dd, J=5.5 Hz, 1.9 Hz, 1H), 3.95 (s, 3H); $^{13}$C NMR (101 MHz, CDCl$_3$): δ 170.3, 162.1, 131.0, 130.1, 122.9, 121.0, 111.5, 52.7; IR (ATR, CH$_2$Cl$_2$): 3155, 2954, 1677, 1606, 1570, 1480, 1439, 1330, 1282, 1204, 1095, 885, 772, 1765 cm$^{-1}$; HRMS (m/z): [M]$^-$ calcd. for C$_8$H$_6$BrO$_3$, 228.9506; found, 228.9516.

Methyl 4-bromo-2-(2-((tert-butoxycarbonyl)amino) ethoxy)benzoate (INT2)

To a stirred solution of methyl 4-bromo-2-hydroxybenzoate (INT1, 231 mg, 1.0 equiv., 1.00 mmol), N-Boc-ethanolamine (170 μL, 1.1 equiv., 1.10 mmol) and Ph$_3$P (344 mg, 1.3 equiv., 1.30 mmol) in tetrahydrofuran (4.0 mL) in a one-necked flask (25 mL) was added diethyl azodicarboxylate (210 μL, 1.30 equiv., 1.3 mmol) and the reaction mixture was stirred at room temperature. After 1 hour, the mixture was concentrated. The resulting residue was purified by flash column chromatography on silica gel using an eluent system of Heptane/EtOAc 80:20 to afford the desired product as a clear oil (373 mg, 1.00 mmol, 100%). TLC (Heptane:EtOAc, 60:40 v/v, UV, KMnO$_4$): R$_f$=0.52; $^1$H NMR (400 MHz, CDCl$_3$): δ 7.71 (d, J=8.4 Hz, 1H), 7.16 (dd, J=8.3 Hz, 1.8 Hz, 1H), 7.11 (d, J=1.8 Hz, 1H), 5.48 (s, 1H), 4.10 (t, J=5.0 Hz, 2H), 3.90 (s, 3H), 3.57 (q, J=5.3 Hz, 2H) 1.45 (s, 9H); $^{13}$C NMR (101 MHz, CDCl$_3$): δ 165.9, 159.1, 156.1, 133.2, 127.9, 124.4, 119.4, 117.8, 79.6, 69.3, 52.3, 40.0, 28.6; IR (ATR, CH$_2$Cl$_2$): 3384, 2976, 1711, 1589, 1512, 1486, 1436, 1392, 1365, 1276, 1246, 1170, 1094, 773 cm$^{-1}$; HRMS (m/z): [M]$^+$ calcd. for C$_{15}$H$_{20}$BrNO$_5$Na, 376.0417; found, 396.0438.

Methyl 4-bromo-2-(2-(2-((tert-butoxycarbonyl) (methyl)amino)-acetamido)ethoxy)benzoate (INT3)

The bromoarene starting material, methyl 4-bromo-2-(2-((tert-butoxycarbonyl)amino)ethoxy)benzoate (INT2, 748 mg, 1.0 equiv., 2.00 mmol) was dissolved in a 1,4-dioxane solution of hydrochloric acid (4 M in 1,4-dioxane, 6.0 mL, 24 mmol) at 0° C. and the mixture was stirred for 0.5 hours at room temperature and substrate conversion was evaluated by TLC analysis. Upon reaching full conversion of starting material after 0.5 hours, the mixture was treated with Et$_2$O (20 mL) to cause immediate precipitation of a heavy white solid. Decantation of the solvent and repeated trituration with Et$_2$O (2×20 mL) afforded the desired amine as the hydrochloride salt, which was used directly in the following coupling step (603 mg, 1.94 mmol, 97%). A flame-dried flask (50 mL) equipped with a stirrer bar under an argon atmosphere was charged with Boc-Sar-OH (440 mg, 1.2 equiv., 2.33 mmol) followed by HOBt-hydrate (386 mg, 1.3 equiv., 2.52 mmol). Addition of anhydrous dimethylformamide (5.0 mL) was made and the mixture was cooled to 0° C. using an ice bath. Subsequent addition of EDCI (483 mg, 1.3 equiv., 2.52 mmol) was made, followed by addition of the amine-derived hydrochloride (603 mg, 1.0 equiv., 1.94 mmol) from dimethylformamide solution (5.0 mL), followed by the addition of DIPEA (1.01 mL, 3.0 equiv., 5.82 mmol). The ice bath was removed, and the mixture was stirred at room temperature for 3 hours. At this time, the reaction was quenched using water (60 mL) and 1-M aqueous hydrochloric acid solution (20 mL). The mixture was diluted with Et$_2$O (50 mL). The phases were separated, and the aqueous phase was extracted with Et$_2$O (3×50 mL). The combined organic extracts were washed with water (40 mL), saturated aqueous NaHCO$_3$ (40 mL), water (40 mL) and brine (40 mL), before being dried over sodium sulphate and concentrated to afford a crude isolate. The crude isolate was purified by flash column chromatography on silica gel using an eluent system of Heptane/EtOAc 25:75 to afford the desired product as a clear oil (837 mg, 1.88 mmol, 94% over 2 steps). TLC (Heptane:EtOAc, 30:70 v/v, UV, KMnO$_4$): R$_f$=0.33; Two rotameric structures of the N-methylcarbamate were observed. $^1$H NMR (400 MHz, d$_4$-MeOH): δ 7.68 (d, J=8.3 Hz, 1H), 7.33 (s, 1H), 7.20 (d, J=8.3 Hz, 1H), 4.15 (t, J=5.3 Hz, 2H), 3.94-3.82 (m, 5H), 3.65 (t, J=5.2 Hz, 2H), 2.93 (s, 3H), 1.49-1.29 (m, 9H); $^{13}$C NMR (101 MHz, d$_6$-MeOH): δ 172.1, 167.3, 160.4, 157.4, 133.8, 128.8, 125.3, 120.6, 118.8, 81.5, 69.6, 53.5, 52.7, 39.7, 36.3, 28.6; IR (ATR, CH$_2$Cl$_2$): 332, 2975, 1698, 1588, 1485, 1391, 1243, 1149, 1094, 773 cm$^{-1}$; HRMS (m/z): [M]$^+$ calcd. for C$_{18}$H$_{25}$BrN$_2$O$_6$Na, 467.0788; found, 467.0803.

Methyl 4-bromo-2-(2-(2-(2-(diethoxyphosphoryl)-N-methylacetamido)-acetamido)ethoxy)benzoate (INT4)

The bromoarene starting material, methyl 4-bromo-2-(2-(2-((tert-butoxycarbonyl)(methyl)amino)acetamido)ethoxy) benzoate (INT3, 837 mg, 1.0 equiv., 1.88 mmol) was dissolved in a 1,4-dioxane solution of hydrochloric acid (4 M in 1,4-dioxane, 11.2 mL, 22.6 mmol) at 0° C. and the mixture was stirred for 0.5 hours at room temperature. The conditions afforded formation of a solid white precipitate. After 0.5 hours, the mixture was treated with Et$_2$O (50 mL) and agitated by sonication. Partial decantation of the solvent was performed, and the mixture was concentrated. Repeated trituration with Et$_2$O (2×50 mL) afforded the desired amine as a white hydrochloride salt, which was used directly in the following coupling step (683 mg, 1.79 mmol, 95%). A flame-dried flask (50 mL) equipped with a stirrer bar under an argon atmosphere was charged with HOBt-hydrate (199 mg, 1.3 equiv., 1.30 mmol). Addition of anhydrous dimethylformamide (6.0 mL) and diethyl phosphonoacetic acid (193 μL, 1.20 equiv., 1.20 mmol) was made and the mixture was cooled to 0° C. using an ice bath, followed by subsequent addition of EDCI (249 mg, 1.3 equiv., 1.30 mmol). Addition of the amine-derived hydrochloride (382 mg, 1.0 equiv., 1.00 mmol) was made to the reaction mixture, followed by the addition of DIPEA (0.52 mL, 3.0 equiv., 3.0 mmol). The mixture was stirred at room temperature and monitored by TLC analysis to determine product formation. After 23 hours, the reaction was quenched using water (60 mL) and 1 M aqueous hydrochloric acid solution (20 mL) and the mixture was diluted with EtOAc/Et$_2$O (2:1, 60 mL). The phases were separated, and the aqueous phase was extracted with EtOAc/Et$_2$O (2:1, 3×45 mL). The combined organic extracts were washed with water (40 mL), saturated aqueous NaHCO$_3$ (40 mL), water (40 mL) and brine (40 mL), before being dried over sodium sulphate and concentrated to afford a crude isolate. The crude isolate was purified by flash column chromatography on silica gel using an eluent system of EtOAc/MeOH 90:10 to afford the desired phosphonate as a clear oil (454 mg, 0.868 mmol, 87%). TLC (EtOAc:MeOH, 95:5 v/v, UV, KMnO$_4$): R$_f$=0.22; The product was isolated as a mixture of rotamers, data is reported for the major rotamer. $^1$H NMR (400 MHz, CDCl$_3$): δ 7.65 (d, J=8.1 Hz, 1H), 7.55 (t, J=5.7 Hz, 1H), 7.14 (s, 1H), 7.12 (dd, J=8.1 Hz, 1.7 Hz, 1H), 4.18-4.08 (m, 8H), 3.87 (s, 3H), 3.70 (q, J=5.6 Hz, 2H), 3.17 (s, 3H), 3.13 (d, J=21.7 Hz, 2H), 1.31 (t, J=7.1 Hz, 6H); $^{13}$C NMR (101 MHz, CDCl3): δ 168.5, 166.0, 166.0 (d, J=5.6 Hz), 159.0, 132.9, 127.8, 124.2, 119.5, 117.8, 68.1, 63.1 (d, J=6.5 Hz), 52.3, 51.9, 38.6, 38.0, 33.6 (d, J=130.4 Hz), 16.4 (d, J=6.4 Hz); IR (ATR, CH$_2$Cl$_2$): 3299, 2983, 2949, 1717, 1651, 1588, 1395, 12421095, 1049, 1024, 968 cm$^{-1}$; HRMS (m/z): [M]$^+$ calcd. for C$_{19}$H$_{29}$BrN$_2$O$_8$P, 523.0839; found, 523.0864.

Racemic 2-amino-3-((triisopropylsilyl)oxy)propan-1-ol (INT59)

Racemic or R-INTXX may be used interchangeably in the syntheses as the stereocenter is removed at a later stage. This procedure describes the one-step preparation of rac-INT59. Serinol (2.79 g, 3.0 equiv., 30.0 mmol) was dissolved to a near-homogenous mixture in anhydrous dichloromethane (30 mL) and anhydrous dimethylformamide (30 mL) under an argon atmosphere followed by addition of 2,6-lutidine (4.73 mL, 4.0 equiv., 40.0 mmol) and the mixture was stirred vigorously for 30 minutes. Then, TIPSOTf (2.77 mL, 1.0 equiv., 10.0 mmol) was added dropwise over 10 minutes. The reaction was quenched with water (100 mL) and extracted with dichloromethane (4×30 mL) before being washed with brine (2×80 mL). The combined organic phases were dried over sodium sulphate, filtered, and concentrated to afford a clear yellow oil. The crude product was purified by flash column chromatography on silica gel using a eluent system of dichloromethane/MeOH/Et$_3$N: 90:10:1, to afford the desired product as a clear oil.

Methyl N-((benzyloxy)carbonyl)-O-(triisopropylsilyl)-L-serinate (INT60)

Racemic or (R)-INT59 may be used interchangeably in the syntheses as the stereocenter is removed at a later stage in the synthesis. The procedures described in the syntheses of INT60, INT61, (R)-INT59 allows preparation of (R)-INT59 in 3 synthetic steps. Cbz-L-Ser-OMe (5.17 g, 1.0 equiv., 20.0 mmol) was dissolved in anhydrous dichloromethane (40 mL) in a flame-dried, one-necked flask equipped with a stirrer bar, under an argon atmosphere and the solution was cooled to 0° C. Then, 2,6-Lutidine (4.73 mL, 2.0 equiv., 40.0 mmol) and triisopropylsilyl trifluoromethanesulfonate (6.10 mL, 1.1 equiv., 22.0 mmol) were added at 0° C. The reaction was quenched with saturated aqueous ammonium chloride (50 mL) and was extracted with EtOAc (3×60 mL). The combined organic phases washed with water (50 mL) and brine (50 mL) before being dried over sodium sulphate, filtered, and concentrated to afford a crude isolate. The crude product was advanced in the synthesis without further purification.

Benzyl (R)-(1-hydroxy-3-((triisopropylsilyl)oxy)propan-2-yl)carbamate (INT61)

The crude isolate from the silyl-protection step, (INT60, an estimated 8.19 g, 1.0 equiv., 20.0 mmol) was dissolved in MeOH (40 mL) in a one-necked flask (100 mL), equipped with a stirrer bar under an argon atmosphere and the solution was cooled 0° C. in an ice-bath. NaBH$_4$ (1.89 g, 2.5 equiv., 50.0 mmol) was added in one portion, and the reaction was allowed to reach room temperature as the ice-bath thawed overnight. Finally, the reaction was quenched with saturated aqueous ammonium chloride solution (60 mL) and the mixture was diluted using EtOAc (60 mL). The aqueous phase was extracted using EtOAc (2×60 mL). The combined organic phases were washed with water (60 mL) and brine (60 mL) before being dried over sodium sulphate, filtered and concentrated to afford a crude isolate. The crude isolate was purified by flash column chromatography on silica gel using an elution system of Heptane/EtOAc as follows: 90:10→80:20→70:30→60:40→60:40 (500 mL solvent mixtures, column packing in Heptane, Heptane load., 100 mL fractions.) to afford the desired product as a clear oil.

(R)-2-amino-3-((triisopropylsilyl)oxy)propan-1-ol ((R)-INT59)

Racemic or R-INT59 may be used interchangeably in the syntheses as the stereocenter is removed at a later stage. The staring material carbamate (7.61 g, 1.0 equiv. 19.9 mmol) was placed under an argon atmosphere in a one-necked flask (100 mL) equipped with a stirrer bar and was dissolved in MeOH (50 mL). To the reaction mixture was added Pd/C (10% Palladium supported on carbon, 424 mg, 0.02 equiv., 0.399 mmol) and the atmosphere within the reaction vessel was exchanged with hydrogen. Conversion of the starting material was verified by TLC analysis. After reaching full conversion of starting material, the hydrogen gas was removed and the reaction mixture was filtered through Celite, and the filter cake was washed successively with MeOH (3×30 mL). The mixture was concentrated to afford a crude product as a clear oil. The crude product was used without further purification.

Diethyl (2-((2-((2-(5-bromo-2-((1-hydroxy-3-((triisopropylsilyl)oxy)-propan-2-yl)carbamoyl)phenoxy)ethyl)amino)-2-oxoethyl)(methyl)-amino)-2-oxoethyl)phosphonate (INT5)

To the starting material ester, methyl 4-bromo-2-(2-(2-(2-(diethoxyphosphoryl)-N-methylacetamido)acetamido)ethoxy)benzoate (INT4, 695 mg, 1.0 equiv., 1.33 mmol) in MeOH (10.0 mL) was added a solution of sodium hydroxide (271 mg, 5.0 equiv., 6.65 mmol) in water (1.0 mL, 6.3 M). The mixture was stirred at room temperature and conversion was followed by TLC analysis. After reaching full conversion of starting material, the mixture was poured into a mixture of water (48 mL) and 1 M aqueous HCl solution (12 mL) in a separation funnel and checked to verify that the pH of the solution was <2. The mixture was shaken vigorously and extracted with dichloromethane (3×40 mL). The combined organic extracts were washed with brine (20 mL), dried over sodium sulphate and concentrated to afford a colorless solid as the crude product, which was used directly in the following coupling reaction (601 mg, 1.18 mmol, 89%). To a stirring mixture of the free acid (601 mg, 1.0 equiv., 1.18 mmol) in anhydrous dichloromethane (4 mL) under an argon atmosphere, was added DEPBT (701 mg, 2.0 equiv., 2.36 mmol), and triethylamine (0.49 mL, 3.0 equiv., 3.5 mmol), followed by addition of racemic TIPS-serinolamine (rac-INT59, 350 mg, 1.2 equiv., 1.42 mmol) in anhydrous dichloromethane (4 mL). After being stirred for 3 hours at room temperature, the reaction was quenched by addition of water (20 mL), and the mixture was diluted with EtOAc (25 mL) and the layers were separated. The aqueous phase was extracted with EtOAc (3×20 mL). The combined organic phases were washed with 0.5 M aqueous HCl solution (20 mL) and brine (20 mL), dried over sodium sulphate, filtered and concentrated to afford a crude isolate. The crude material was purified by flash column chromatography on silica gel using an elution system of EtOAc/

MeOH 92:8 to afford the desired product as a clear sticky oil (645 mg, 0.873 mmol, 74%). TLC (EtOAc:MeOH, 95:5 v/v, UV, KMnO$_4$): R$_f$=0.21; The compound was isolated as a mixture of at least 3 conformational isomers. Data is reported for the major isomer. $^1$H NMR (400 MHz, CDCl$_3$): δ=8.32 (d, J=7.7 Hz, 1H), 8.05 (d, J=8.3 Hz, 1H), 7.87 (t, J=5.8 Hz, 1H), 7.21 (dd, J=8.5 Hz, 1.7 Hz, 1H), 7.09 (d, J=1.7 Hz, 1H), 4.47 (s, 1H), 4.30-3.44 (m, 14H), 3.11 (s, 3H), 3.07 (d, J=21.4 Hz, 1H), 1.31 (d, J=7.1 Hz, 9H), 1.14-1.00 (m, 21H). $^{13}$C NMR (101 MHz, CDCl$_3$): δ 169.1, 166.0 (d, J=5.6 Hz), 164.3, 157.3, 133.6, 127.7, 124.8, 120.9, 116.0, 68.7, 63.3 (d, J=6.4 Hz), 63.2 (d, J=6.3 Hz), 63.1, 62.3, 52.4, 52.1, 39.5, 38.0, 33.3 (d, J=132.2 Hz), 18.1, 18.1, 16.4 (d, J=6.4 Hz), 16.4 (d, J=6.3 Hz), 12.0; IR (ATR, CH$_2$Cl$_2$): 3400, 2941, 2865, 1650, 1587, 1527, 1479, 1394, 1228, 1048, 1024, 882, 682 cm$^{-1}$; HRMS (m/z): [M]$^+$ calcd. for C$_{30}$H$_{54}$BrN$_3$O$_9$PSi, 738.2545; found, 738.2572.

(E)-16-bromo-7-methyl-11-(((triisopropylsilyoxy)methyl)-3,4,6,7,11,12-hexahydrobenzo[n][1]oxa[4,7,12]triazacyclopentadecine-5,8,13(2H)-trione (INT6)

To a stirring solution of the phosphonate alcohol, diethyl (2-((2-((2-(5-bromo-2-((1-hydroxy-3-((triisopropylsilyl)oxy)propan-2-yl)carbamoyl) phenoxy)ethyl)amino)-2-oxoethyl)(methyl)amino)-2-oxoethyl)phosphonate (INT5, 331 mg, 1.0 equiv., 448 μmol) in dichloromethane (12 mL) in a one-necked flask (50 mL) equipped with a stirrer bar was added Dess-Martin periodinane (378 mg, 2.0 equiv., 896 μmol). After stirring the mixture for 1 hour at ambient temperature, saturated aqueous NaHCO$_3$ (6 mL) and saturated aqueous Na$_2$S$_2$O$_3$ (6 mL) were added, the mixture was transferred to a separatory funnel, and the mixture was shaken vigorously until the organic phase became clear. The organic phase was diluted with dichloromethane (10 mL), and the layers were separated. The aqueous phase was extracted with dichloromethane (3×10 mL). The combined organic extracts were washed with brine (20 mL), dried over sodium sulphate, filtered, and concentrated. The crude product was directly advanced in the synthesis after verifying formation of the desired aldehyde. The aldehyde (an estimated 330 mg, 1.0 equiv., 448 μmol) was dissolved in anhydrous tetrahydrofuran (250 mL) in a one-necked flask (500 mL) equipped with a stirrer bar under an argon atmosphere, and anhydrous triethylamine (311 μL, 5.0 equiv., 2.24 mmol) was added, followed immediately by TMEDA (134 μL, 2.0 equiv., 896 μmol) and Zn(OTf)$_2$ (651 mg, 4.0 equiv., 1.79 mmol). The mixture was left stirring at room temperature for 3 hours. The reaction was quenched with water (40 mL) and saturated aqueous NH$_4$Cl (40 mL). The mixture was poured into a separatory funnel and the layers were separated. The aqueous phase was extracted with EtOAc (3×40 mL). The combined organic phases were washed with brine (80 mL) before being dried over sodium sulphate, filtered and concentrated to afford a pale-yellow to white sticky residue. The crude material was purified by flash column chromatography using an elution system of Heptane/Acetone 2:3 to afford the desired product as a white solid (217 mg, 372 μmol, 83% over 2 steps). TLC (EtOAc:MeOH, 90:10 v/v, UV, KMnO$_4$): R$_f$=0.48; $^1$H NMR (400 MHz, d$_6$-acetone): δ 7.96 (d, J=8.4 Hz, 1H), 7.89 (d, J=9.0 Hz, 1H), 7.75 (d, J=4.4 Hz, 1H), 7.43 (d, J=1.8 Hz, 1H), 7.28 (dd, J=8.4 Hz, 1.8 Hz, 1H), 7.04 (dd, J=15.2 Hz, 3.0 Hz, 1H), 6.54 (dd, J=15.2 Hz, 2.4 Hz, 1H), 5.08-4.96 (m, 2H), 4.69-4.50 (m, 2H), 4.32 (d, J=17.3 Hz, 1H), 3.96 (dd, J=9.6 Hz, 4.3 Hz, 1H), 3.89-3.73 (m, 3H), 3.61-3.46 (m, 1H), 3.08 (s, 3H), 1.15-0.97 (m, 21H); $^{13}$C NMR (101 MHz, d$_6$-acetone): δ 170.3, 166.4, 164.2, 157.5, 144.1, 134.3, 126.9, 125.0, 122.8, 121.7, 116.6, 66.6, 66.1, 53.7, 52.8, 38.9, 36.9, 18.4, 18.3, 12.7; IR (ATR, CH$_2$Cl$_2$): 3398, 3289, 3074, 2941, 2865, 1646, 1587, 1525, 1463, 1394, 1227, 1214, 1113, 881, 682 cm$^{-1}$; HRMS (m/z): [M]$^+$ calcd. for C$_{26}$H$_{41}$BrN$_3$O$_5$Si, 582.1993; found, 582.2040.

2-dodecyl-6-methyl-1,3,6,2-dioxazaborocane-4,8-dione (INT7)

Dry and degassed Et$_2$O (20 mL) was added into flame-dried, grinded magnesium turnings (233 mg, 1.20 equiv., 9.60 mmol) under an argon atmosphere in a one-necked flask (100 mL) equipped with a stirrer bar and a reflux condenser. Then, a catalytic amount of iodine was added before 1-bromododecane (1.92 mL, 1.00 equiv., 8.00 mmol) was added dropwise, resulting in a gently refluxing mixture, that was stirred for 1 hour at reflux. The freshly prepared Grignard reagent solution was added dropwise to a solution containing trimethyl borate (12.0 mmol, 920 μL, 1.5 equiv.) at −78° C. cooled in anhydrous, degassed tetrahydrofuran (20 mL) in a flame-dried, one-necked flask (100 mL) under an argon atmosphere. The resulting mixture was stirred for 1 hour at −78° C. and at room temperature for a subsequent 1 hour. The reaction was quenched by the addition of 1 M aqueous HCl solution (30 mL), and stirring was continued for 15 minutes, at which time the layers were separated and the aqueous layer was extracted with Et$_2$O (3×15 mL). The combined organic extracts were washed with water (30 mL) and brine (30 mL) before being dried over sodium sulphate and concentrated to afford a white residue, that was recrystallised from Et$_2$O/hexane to afford the desired product as a white solid in low purity.

To a stirred solution of the dodecylboronic acid (1.29 g) in dimethyl sulfoxide (20 mL) was added N-methylaminodiacetic acid (594 mg, 1.00 equiv., 4.00 mmol). The reaction was then heated to 100° C. in a one-necked flask (100 mL) under a flow of nitrogen. Once the reaction was deemed complete, the mixture was poured into Et$_2$O (40 mL) in a separatory funnel and water (20 mL) was added. The organic phase was a cloudy solution that contained a white precipitate. The dimethylsulfoxide containing aqueous phase was extracted with Et$_2$O (3×20 mL) and the combined organic extracts, still containing a white cloudy precipitate were washed with water (2×30 mL) and brine before being concentrated onto Celite. The crude isolate was purified by flash column chromatography on silica gel using an eluent system of Heptane/Acetone 50:50 to afford the desired dodecyl-MIDA-boronate as a white solid (751 mg, 2.31 mmol, 58%). TLC (Heptane:Acetone, 50:50 v/v, KMnO$_4$): R$_f$=0.37; $^1$H NMR (400 MHz, d$_3$-acetonitrile): δ 3.91 (d, J=16.9 Hz, 2H), 3.75 (d, J=16.9 Hz, 2H), 2.83 (s, 3H), 1.34-1.23 (m, 20H), 0.88 (t, J=6.8 Hz, 3H), 0.57 (t, J=6.9 Hz, 2H). $^{13}$C NMR (101 MHz, d$_3$-acetonitrile): δ 169.2, 62.7, 46.5, 33.7, 32.6, 30.4, 30.4, 30.4, 30.4, 30.2, 30.1, 25.0, 23.4, 14.4, the carbon attached to boron was not observed; IR (ATR, neat): 2957, 2917, 2848, 1743, 1462, 1340, 1300, 1288, 1030, 992, 972, 905, 864 cm$^{-1}$; HRMS (m/z): [M]$^+$ calcd. for C$_{17}$H$_{33}$BNO$_4$, 326.2497; found, 326.2502.

(E)-16-dodecyl-7-methyl-11-(((triisopropylsilyl)oxy)methyl)-3,4,6,7,11,12-hexahydrobenzo[n][1]oxa[4,7,12]triazacyclopentade-cine-5,8,13(2H)-trione (INT8)

A suspension of the macrocyclic bromoarene, (E)-16-bromo-7-methyl-11-((((triisopropylsilyl)oxy)methyl)-3,4,6, 7,11,12-hexahydrobenzo[n][1]oxa[4,7,12]triazacyclopentadecine-5,8,13(2H)-trione (INT6, 58 mg, 1.0 equiv., 100 µmol), dodecyl-MIDA-boronate (INT1, 65 mg, 2.0 equiv., 200 µmol), $K_2CO_3$ (69 mg, 5.0 equiv., 0.50 mmol) and tetrakis(triphenylphosphine)palladium (6 mg, 0.05 equiv., 5 µmol) in a degassed mixture of toluene/water (10:1, 3 mL) was prepared. The solution was heated to 80° C. and stirred at this temperature for 23 hours before being analyzed by TLC, and then heated to 100° C. and stirred for an additional 7 hours. At this time, the reaction mixture was cooled to room temperature. The reaction mixture was separated between EtOAc (15 mL) and water (15 mL). The mixture was poured into a separatory funnel and the phases were separated. The aqueous phase was extracted with EtOAc (3×10 mL) and washed with brine (25 mL) before being dried over sodium sulphate, filtered and concentrated to afford a crude isolate. The crude isolate was purified by flash column chromatography on silica gel using an elution system of Heptane/Acetone 7:3, to afford the desired product as a clear thin film (32 mg, 48 µmol, 48%). TLC (Heptane: Acetone, 50:50 v/v, UV, $KMnO_4$): $R_f$=0.38; $^1$H NMR (400 MHz, $CDCl_3$): δ 7.78 (d, J=7.9 Hz, 1H), 7.51 (d, J=8.6 Hz, 1H), 7.08 (dd, J=15.2 Hz, 3.5 Hz, 1H), 6.84 (d, J=7.9 Hz, 1H), 6.74 (s, 1H), 6.55 (s, 1H), 6.48 (dd, J=15.2 Hz, 1.3 Hz, 1H), 4.98 (s, 1H), 4.52-4.34 (m, 2H), 4.19 (d, J=17.3 Hz, 1H), 3.92 (dd, J=9.8 Hz, 3.8 Hz, 1H), 3.84 (dd, J=9.7 Hz, 4.9 Hz, 1H), 3.81-3.65 (m, 2H), 3.64-3.51 (m, 1H), 3.14 (s, 3H), 2.61 (t, J=7.8 Hz, 2H), 1.37-1.20 (m, 20H), 1.15-0.97 (m, 21H), 0.88 (t, J=6.7 Hz, 3H); $^{13}$C NMR (101 MHz, $CDCl_3$): δ 169.2, 166.5, 165.6, 155.4, 148.6, 145.0, 131.5, 122.0, 121.2, 120.0, 112.7, 65.2, 65.1, 54.1, 52.3, 38.8, 36.7. 36.3, 32.1, 31.3, 29.8, 29.8, 29.8, 29.8, 29.6, 29.5, 29.5, 22.8, 18.1, 14.3, 12.1; IR (ATR, $CH_2Cl_2$): 3392, 3286, 3072, 2924, 2855, 1651, 1610, 1527, 1249, 1116, 832, 683 cm$^{-1}$; HRMS (m/z): [M]$^+$ calcd. for $C_{38}H_{66}N_3O_5Si$, 672.4766; found, 672.4805.

(E)-16-dodecyl-11-(hydroxymethyl)-7-methyl-3,4,6,
7,11,12-hexahydro-benzo[n][1]oxa[4,7,12]triazacyclopentadecine-5,8,13(2H)-trione (PH462)

The macrocyclic silyl-protected compound, (E)-16-dodecyl-7-methyl-11-(((triisopropylsilypoxyl)methyl)-3,4,6,7,11,12-hexahydrobenzo [n][1]oxa[4,7,12]triazacyclopentadecine-5,8,13(2H)-trione (INT8, 100 mg, 1.0 equiv., 141 µmol) was dissolved in anhydrous tetrahydrofuran (3.0 mL) under an argon atmosphere and the mixture was cooled to 0° C. Addition of tetrabutylammonium fluoride (1M in tetrahydrofuran, 183 µL, 1.3 equiv., 183 µmol) was made dropwise at 0° C. and the reaction mixture was stirred at room temperature for an additional 0.5 hr. The reaction was quenched by the addition of water (15 mL), and the reaction mixture was diluted with EtOAc (50 mL). The phases were separated, and the organic phase was washed thoroughly with water (30 mL), brine (30 mL), saturated aqueous $NH_4Cl$ (30 mL) and water (30) before being collected and concentrated to afford the crude alcohol (72 mg, 140 µmol, 99%). TLC (EtOAc:MeOH, 90:10 v/v, UV, $KMnO_4$): $R_f$=0.22; $^1$H NMR (400 MHz, $d_6$-DMSO): δ 8.30 (t, J=4.2 Hz, 1H), 7.93 (d, J=8.9 Hz, 1H), 7.76 (d, J=7.9 Hz, 1H), 7.01 (s, 1H), 6.88 (d, J=7.8 Hz, 1H), 6.85 (dd, J=15.2 Hz, 2.9 Hz, 1H), 6.32 (dd, J=15.3 Hz, 2.3 Hz, 1H), 4.99 (t, J=5.6 Hz, 1H), 4.81 (d, J=8.1 Hz, 1H), 4.48-4.25 (m, 2H), 4.12 (d, J=17.1 Hz, 1H), 3.84 (d, J=17.1 Hz, 1H), 3.61-3.48 (m, 2H), 3.43-3.34 (m, 1H), 3.00 (s, 3H), 2.61 (t, J=7.6 Hz, 2H), 1.58 (p, J=7.0 Hz, 2H), 1.32-1.18 (m, 20H), 0.85 (t, J=6.7 Hz, 3H); $^{13}$C NMR (101 MHz, $d_6$-DMSO): δ 169.2, 165.7, 164.4, 155.6, 147.6, 143.5, 131.0, 120.5, 120.2, 120.0, 112.3, 64.9, 63.1, 52.4, 51.7, 38.1, 36.5, 35.2, 31.2, 30.7, 29.0, 29.0, 29.0, 29.0, 28.8, 28.7, 28.6, 22.0, 13.9; IR (ATR, neat): 3351, 2924, 2851, 1644, 1619, 1531, 1467, 1249, 1034 cm$^{-1}$; HRMS (m/z): [M]$^+$ calcd. for $C_{29}H_{46}N_3O_5$, 516.3432; found, 516.3436.

(E)-16-dodecyl-7-methyl-11-methylene-3,4,6,7,11,
12-hexahydro-benzo[n][1]oxa[4,7,12]triazacyclopentadecine-5,8,13(2H)-trione (PH466)

The starting material alcohol, (E)-16-dodecyl-11-(hydroxymethyl)-7-methyl-3,4,6,7,11,12-hexahydrobenzo[n][1]oxa[4,7,12]triazacyclopentadecine-5,8,13(2H)-trione (INT9, 20 mg, 1.0 equiv., 39 µmol) was dissolved in anhydrous acetonitrile/tetrahydrofuran (1:1, 1.0 mL) under an argon atmosphere, to become a colorless, clear solution. Addition of DSC (16 mg, 1.5 equiv., 58 µmol) and DIPEA (14 µL, 2.0 equiv., 78 µmol) was made to the reaction mixture at room temperature. The reaction was stirred for 24 hours at 40° C. The reaction mixture was cooled to room temperature before being concentrated using a flow of nitrogen. A crude $^1$H-NMR was recorded in $d_3$-acetonitrile clearly indicating the formation of the desired APD-containing compound as the major product of the reaction. The $d_3$-acetonitrile was returned into the reaction vessel and the NMR tube was washed with acetonitrile (1 mL). The acetonitrile in the reaction vessel was removed using a nitrogen flow. The material was diluted with dimethylsulfoxide (3.0 mL) and purified by preparative HPLC followed by lyophilization to afford 8.2 mg of a 3:1 mixture of the product (5.9 mg, 12 µmol, 31%) and a tentatively assigned dihydrooxazole by-product. Preparative TLC was performed using an eluent system of EtOAc/MeOH 8:2 followed by collection of product from the isolated silica using a mixture of acetonitrile/MeOH 18:2 (15 mL). Water (50 mL) was added to the solution to cause precipitation of the isolated product. The resulting suspension was lyophilized to afford pure PH466 as a white flocculent solid. $^1$H NMR (950 MHz, $d_6$-DMSO): δ 9.26 (s, 1H), 8.52 (d, J=4.7 Hz, 1H), 7.84 (d, J=7.9 Hz, 1H), 7.08 (s, 1H), 7.00 (d, J=15.3 Hz, 1H), 6.94 (d, J=7.9 Hz, 1H), 6.44 (d, J=15.3 Hz, 1H), 6.24 (s, 1H), 5.30 (s, 1H), 4.41 (t, J=4.9 Hz, 2H), 4.03 (s, 2H), 3.46 (q, J=5.0 Hz, 2H), 3.05 (s, 3H), 2.63 (t, J=7.8 Hz, 2H), 1.59 (p, J=7.0 Hz, 2H), 1.31-1.21 (m, 18H), 0.85 (q, J=7.1 Hz, 3H); $^{13}$C NMR (239 MHz, $d_6$-DMSO): δ 169.5, 165.2, 163.7, 155.4, 148.8, 140.0, 137.3, 131.6, 121.0, 119.6, 116.5, 112.3, 111.3, 65.5, 52.5, 38.1, 36.9, 35.2, 31.3, 30.7, 29.0, 29.0, 29.0, 29.0, 28.9, 28.7, 28.7, 22.1, 14.0; IR (ATR, acetonitrile): 3300, 3075, 2923, 2853, 1654, 1610, 1528, 1495, 1467, 1426, 1396, 1252, 1173, 1118, 1042, 972 cm-1; HRMS (m/z): [M]$^+$ calcd. for $C_{29}H_{44}N_3O_4$, 498.3326; found, 498.3351.

Example 3—Synthesis of PH911

Figure 3:
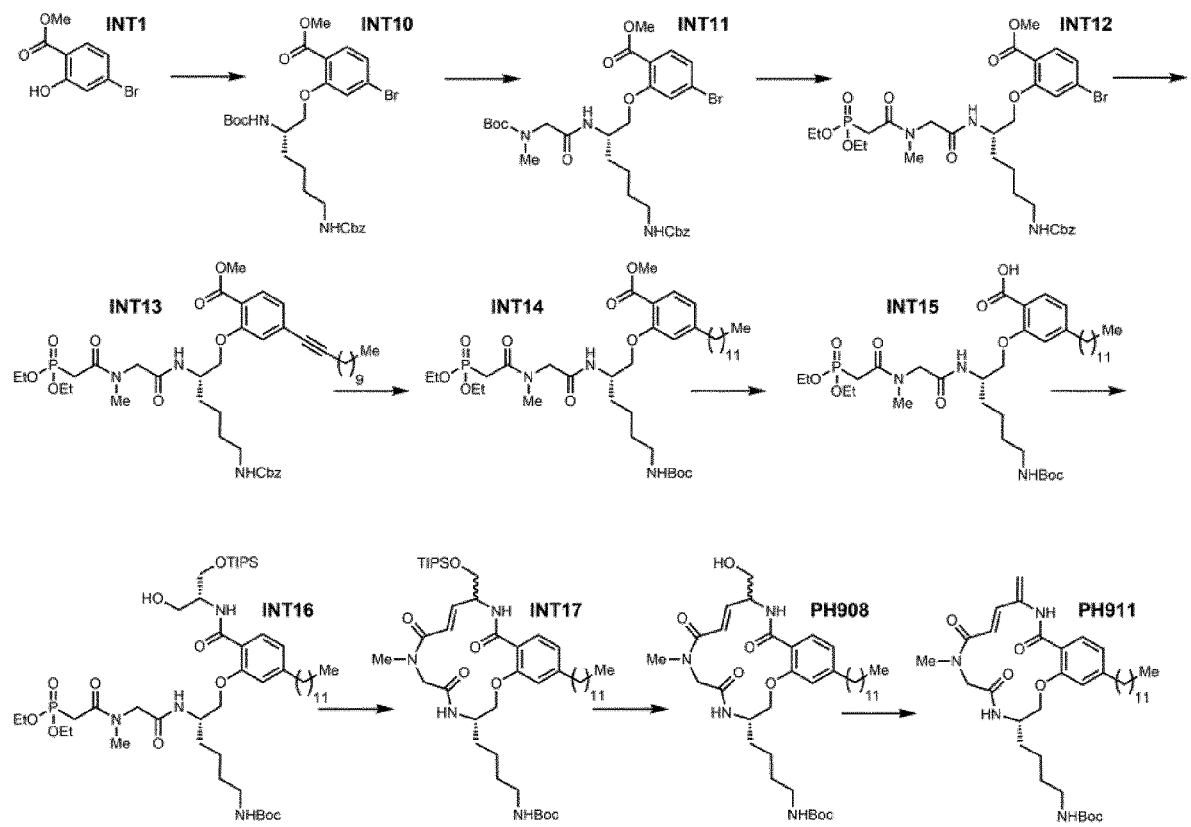
FIG. 3 shows the synthetic route to PH911 and the negative control compound PH908.

In the following is described the synthesis of PH911 and its specific intermediates (INT) (see FIG. 3).

Methyl (S)-2-((6-(((benzyloxy)carbonyl)amino)-2-
((tert-butoxycarbonyl)amino)hexyl)oxy)-4-bromobenzoate (INT10)

To a stirred solution of methyl 4-bromo-2-hydroxybenzoate (INT1, 2.75 g, 1.0 equiv., 11.9 mmol), the Boc-protected amino alcohol N—Z-L-lysinol (4.80 g, 1.1 equiv., 13.1 mmol) and $Ph_3P$ (3.43 g, 1.1 equiv., 13.1 mmol) in anhydrous toluene (48 mL) and the solution was cooled to 0° C. in an ice-bath, diethyl azodi-carboxylate (40 wt % in toluene, 5.96 mL, 1.10 equiv., 13.1 mmol) was added dropwise at 0° C. and the reaction mixture was stirred at room temperature overnight. The mixture was concentrated, before being directly purified by flash column chromatography on silica gel to afford the desired product as a clear sticky oil, that slowly solidified to a white solid.

Methyl (S)-2-((6-(((benzyloxy)carbonyl)amino)-2-(2-((tert-butoxycarbonyl)(methyl)amino)acetamido)hexyl)oxy)-4-bromobenzoate (INT11)

The starting material carbamate derivative, (INT10, 6.78 g, 1.0 equiv., 11.7) was placed in a one-necked flask equipped with a stirrer bar and the flask was placed in an ice-bath. Addition of 4 M hydrochloric acid in 1,4-dioxane (29.3 mL, 10 equiv., 117 mmol) was made at 0° C. and the mixture was stirred for 0.5 hours at room temperature, at which time, TLC analysis indicated full conversion of starting material. Repeated addition of Et$_2$O and concentration afforded the amine hydrochloride as a white solid, that was used directly in the subsequent coupling step. Subsequently, a one-necked flask equipped with a stirrer bar under an argon atmosphere was charged with the amine-derived hydrochloride (an estimated 6.04 g, 1.0 equiv., 11.7 mmol), Boc-Sar-OH (2.77 g, 1.25 equiv., 14.6 mmol) followed by the addition of anhydrous dimethylformamide (59 mL). The mixture was cooled to 0° C. using an ice bath followed by addition of TBTU (5.55 g, 1.25 equiv., 14.6 mmol), followed by the addition of DIPEA (6.11 mL, 3.0 equiv., 35.1 mmol). The mixture was stirred at room temperature overnight. Upon completion, the reaction was quenched using water and 1 M aqueous hydrochloric acid solution (2:1) and the mixture was diluted with EtOAc/Et$_2$O (3:1). The phases were separated, and the aqueous phase was extracted with EtOAc/Et$_2$O (3:1, ×3).

The combined organic extracts were washed with water, saturated aqueous sodium bicarbonate and brine, before being dried over sodium sulphate and concentrated to afford a crude isolate. The crude material was purified by flash column chromatography on silica gel to afford the desired product as an amorphous solid.

Methyl (S)-2-((6-(((benzyloxy)carbonyl)amino)-2-(2-(diethoxyphosphoryl)-N-methylacetamido)acetamido)hexyl)oxy)-4-bromobenzoate (INT12)

The starting material carbamate derivative, (INT11, 7.35 g, 1.0 equiv., 11.3 mmol) was placed in a one-necked flask equipped with a stirrer bar and the flask was placed in an ice-bath. Addition of 4 M hydrochloric acid in 1,4-dioxane (28.3 mL, 10 equiv., 113 mmol) was made at 0° C. and the mixture was stirred for 0.5 hours at room temperature, at which time, TLC analysis indicated full conversion of starting material. Repeated addition of Et$_2$O and concentration afforded the amine hydrochloride as a white solid, that was used directly in the subsequent coupling step. Subsequently, a one-necked flask equipped with a stirrer bar under an argon atmosphere was charged with the amine-derived hydrochloride (an estimated 6.63 g, 1.0 equiv., 11.3 mmol), diethylphosphonoacetic acid (2.27 mL, 1.25 equiv., 14.1 mmol) followed by the addition of anhydrous dimethylformamide (57 mL). The mixture was cooled to 0° C. using an ice bath followed by addition of TBTU (5.36 g, 1.25 equiv., 14.1 mmol), followed by the addition of DIPEA (5.90 mL, 3.0 equiv., 33.9 mmol). The mixture was stirred at room temperature overnight. Upon completion, the reaction was quenched using water and 1M aqueous KHSO$_4$ solution (2:1) and the mixture was diluted with EtOAc/Et$_2$O (3:1). The phases were separated and the aqueous phase was extracted with EtOAc/Et$_2$O (3:1, ×3). The combined organic extracts were washed with water, saturated aqueous sodium bicarbonate and brine, before being dried over sodium sulphate and concentrated to afford a crude isolate. The crude material was purified by flash column chromatography on silica gel to afford the desired product as an amorphous sticky solid.

Methyl (S)-2-((6-(((benzyloxy)carbonyl)amino)-2-(2-(2-(diethoxyphosphoryl)-N-methylacetamido)acetamido)hexyl)oxy)-4-(dodec-1-yn-1-yl)benzoate (INT13)

A flame-dried, one-necked flask was charged with the bromoarene derivative (INT12, 7.36 g, 1.0 equiv., 10.1 mmol), CuI (385 mg, 0.20 equiv., 2.02 mmol), PdCl$_2$(PPh$_3$)$_2$ (709 mg, 0.10 equiv., 1.01 mmol), and the atmosphere of the reaction vessel was evacuated and replaced with argon twice. Anhydrous tetrahydrofuran (51 mL), 1-dodecyne (4.32 mL, 2.0 equiv., 20.2 mmol) and Et$_3$N (4.22 mL, 3.0 equiv., 30.3 mmol) was added. The mixture was heated to 50° C., and after 12 hours of reaction time, the mixture was concentrated on the rotary evaporator, before being directly purified by flash column chromatography on silica gel to afford the desired product as a brownish sticky oil, not in analytical purity.

Methyl (S)-2-((6-(((tert-butoxycarbonyl)amino)-2-(2-(2-(diethoxyphosphoryl)-N-methylacetamido)acetamido)hexyl)oxy)-4-dodecylbenzoate (INT14)

A one-necked flask equipped with a stirrer bar was charged with the starting material, Cbz-protected alkyne derivative (INT13, 8.60 g, 1.00 equiv., 10.5 mmol), and the atmosphere in the reaction vessel was exchanged to argon. Addition of Boc$_2$O (2.87 g, 1.25 equiv., 13.1 mmol) was made, followed by addition of Pd/C (0.05 equivalents in Pd). Subsequently, addition of EtOAc (53 mL) was made and the reaction vessel was flushed with hydrogen and the hydrogen atmosphere was maintained for 3 days at 10 bar. The mixture was filtered through celite and evaporated. The residue was dissolved in EtOAc (53 mL). Fresh Pd/C and Boc$_2$O (same quantity as above) were added and the reaction vessel was flushed with hydrogen and the hydrogen atmosphere was maintained overnight at 10 bar After reaching full conversion of starting material as indicated by LCMS analysis, the reaction mixture was filtered through celite and the filter cake was washed with EtOAc, to afford a crude product. The crude product was purified by flash column chromatography on silica gel to afford the desired product as a clear sticky oil.

(S)-2-((6-((tert-butoxycarbonyl)amino)-2-(2-(2-(diethoxyphosphoryl)-N-methylacetamido)acetamido)hexyl)oxy)-4-dodecylbenzoic acid (INT15)

The starting material methyl ester (INT14, 5.80 g, 1.0 equiv., 7.40 mmol), was dissolved in a mixture of tetrahydrofuran/MeOH/H$_2$O 6:1:1 (74 mL), followed by the addition of LiOH·H$_2$O (621 mg, 2.0 equiv., 14.8 mmol) and the mixture was stirred at room temperature while being followed by LCMS analysis. Upon reaching full conversion after 12 hours, the mixture was poured into a separatory funnel, containing water/brine 2:1 and EtOAc, before the mixture was adjusted to pH<4, using 1.0 M aqueous KHSO$_4$ solution. The phases were separated and the aqueous phase was extracted with EtOAc (×3). The combined organic extracts were washed with brine, before being dried over sodium sulphate, filtered and concentrated. The crude isolate was directly utilized in the following coupling step without further purification.

tert-butyl ((S)-5-(2-(2-(diethoxyphosphoryl)-N-methylacetamido)-acetamido)-6-(5-dodecyl-2-(((R)-1-hydroxy-3-((triisopropylsilypoxy)-propan-2-yl)carbamoyl)phenoxy)hexyl)carbamate (INT16)

To a stirring mixture of the free acid (INT15, an estimated 5.70 g, 1.0 equiv., 7.40 mmol) in anhydrous dichloromethane (18.5 mL) in a one-necked flask equipped with a stirrer bar, under an argon atmosphere, was added DEPBT (2.0 equiv.), and Et$_3$N (3.09 mL, 3.0 equiv., 22.2 mmol), followed by addition of the serinolamine ((R)-INT59, 2.06 g, 1.20 equiv., 8.88 mmol) in anhydrous dichloromethane (18.5 mL). After being stirred overnight at room temperature, the reaction was quenched by addition of water and 1 M aqueous KHSO$_4$ solution (2:1), the mixture was diluted with EtOAc in a separatory funnel and the layers were separated. The aqueous phase was extracted with EtOAc (×3). The combined organic phases were washed with water, 1 M aqueous potassium carbonate (×2), and brine, before being dried over sodium sulphate, filtered and concentrated to afford a crude isolate. The crude material was purified by flash column chromatography on silica gel to afford the desired product as a clear sticky oil with a yellow discoloration.

tert-butyl (4-((3S,11R,E)-16-dodecyl-7-methyl-5,8,13-trioxo-11-(((triisopropylsilypoxy)methyl)-2,3,4,5,6,7,8,11,12,13-decahydrobenzo-[n][1]oxa[4,7,12]triazacyclopentadecin-3-yl)butyl)carbamate (INT17)

To a stirring solution of the phosphonate alcohol (INT16, 400 mg, 1.0 equiv. 400 µmol) in dichloromethane (8.0 mL) in a one-necked flask (50 mL) equipped with a stirrer bar was added Dess-Martin periodinane (339 mg, 2.0 equiv., 800 µmol). After stirring the mixture for 1.0 hour at ambient temperature, the reaction was poured into a separatory funnel containing saturated aqueous NaHCO$_3$ (10 mL) and saturated aqueous Na$_2$S$_2$O$_3$ (10 mL), using dichloromethane (20 mL) to wash the reaction vessel and dilute the organic phase in the separatory funnel. The mixture was shaken vigorously until the organic phase became clear. The aqueous phase was extracted with dichloromethane (3×15 mL). The combined organic extracts were washed with brine (20 mL), dried over sodium sulphate, filtered, and concentrated. The crude product was directly advanced in the synthetic sequence. A one-necked flask (100 mL) equipped with a stirrer bar under an argon atmosphere, was charged with anhydrous Et$_3$N (167 µL, 3.0 equiv., 1.20 mmol), TMEDA (76 µL, 1.25 equiv., 0.50 mmol) and Zn(OTf)$_2$ (371 mg, 2.5 equiv., 1.00 mmol) in anhydrous tetrahydrofuran (16 mL). The aldehyde precursor directly applied from the oxidation step (approximately 400 mg, 1.0 equiv., 400 µmol) was dissolved in anhydrous tetrahydrofuran (16 mL), and was added to the aforementioned solution using a syringe pump over 1 hour. Subsequently, the mixture was left stirring at room temperature for 1 hour. The reaction was quenched with water (40 mL) followed by the addition of brine (40 mL) and 1.0 M aqueous HCl solution (20 mL), before EtOAc (40 mL) was added to the mixture. The mixture was poured into a separatory funnel and the layers were separated, and the aqueous phase was extracted with EtOAc (3×40 mL). The combined organic phases were washed with water/brine 4:1 (50 mL), 1 M aqueous potassium carbonate/brine 4:1 (50 mL) and brine (50 mL) before being dried over sodium sulphate, filtered and concentrated to afford a crude isolate. The crude material was purified by flash column chromatography using an elution system of Heptane/acetone as follows: 90:10 (0 min.)→90:10 (1 min.)→50:50 (20 min.) (25 g column, dichloromethane load (2×4.0 mL), 60 mL/min.). The desired product was afforded as an amorphous colorless solid.

tert-butyl (4-((3S,11R,E)-16-dodecyl-11-(hydroxymethyl)-7-methyl-5,8,13-trioxo-2,3,4,5,6,7,8,11,12,13-decahydrobenzo[n][1]oxa-[4,7,12]triazacyclopentadecin-3-yl)butyl)carbamate (PH908)

The starting material silylether (INT17, 90 mg, 1.0 equiv., 107 µmol), was charged into a one-necked flask (50 mL) equipped with a stirrer bar under an argon atmosphere. The starting material was dissolved in anhydrous tetrahydrofuran (2.1 mL) and the solution was cooled to 0° C. in an ice-bath. Subsequent addition of tetrabutylammonium fluoride (1 M solution in tetrahydrofuran, 134 µL, 1.25 equiv., 134 µmol) was made at 0° C. and subsequently, the ice-bath was removed and the mixture was stirred at room temperature. After 1 hour of reaction time, addition of Et$_2$O (5.0 mL) was made and the solution was concentrated using a stream of nitrogen to afford a crude product. The crude product was purified by flash column chromatography on silica gel using an elution system of EtOAc/MeOH as follows: 100:0 (0 min.) –>100:0 (1 min.) –>90:10 (14 min.), 12 g column, 45 mL/min., EtOAc load (2×2.0 mL), to afford the desired product as a colorless amorphous solid.

tert-butyl (S,E)-(4-(16-dodecyl-7-methyl-11-methylene-5,8,13-trioxo-2,3,4,5,6,7,8,11,12,13-decahydrobenzo[n][1]oxa[4,7,12]-triazacyclopentadecin-3-yl)butyl)carbamate (PH911)

The starting material alcohol (INT18, 22 mg, 1.0 equiv., 33 µmol) was dissolved in anhydrous acetonitrile/tetrahydrofuran (1.0:1.0 mL) under an argon atmosphere, to become a colorless, clear solution. Addition of DSC (18 mg, 2.0 equiv., 65 µmol) and DIPEA (17 µL, 3.0 equiv., 98 µmol) was made to the reaction mixture at room temperature. The reaction was stirred for 19 hours at 45° C. The reaction mixture was cooled to room temperature before being concentrated using a flow of nitrogen. The crude product was analysed by $^1$H-NMR spectroscopy to evaluate product formation. The crude product was purified by preparative HPLC using an elution system of acetonitrile/water, followed by concentration to afford the desired product as a colorless solid. $^1$H NMR (400 MHz, DMSO-d$_6$) δ=9.03 (s, 1H), 8.27 (d, J=6.4 Hz, 1H), 7.81 (d, J=7.9 Hz, 1H), 7.09 (s, 1H), 6.97 (d, J=15.4 Hz, 1H), 6.94 (d, J=7.9 Hz, 1H), 6.78 (d, J=5.0 Hz, 1H), 6.36 (d, J=15.3 Hz, 1H), 6.16 (s, 1H), 5.35 (s, 1H), 4.25-4.18 (m, 3H), 3.99-3.93 (m, 2H), 3.85-3.75 (m, 1H), 3.70-3.61 (m, 1H), 3.02 (d, J=2.5 Hz, 3H), 2.91 (q, J=6.6 Hz, 2H), 2.64 (t, J=7.6 Hz, 2H), 1.66-1.50 (m, 4H), 1.38 (s, 9H), 1.24 (s, 20H), 0.86 (t, J=6.6 Hz, 3H).

Example 4—Synthesis of PH741

Figure 4:
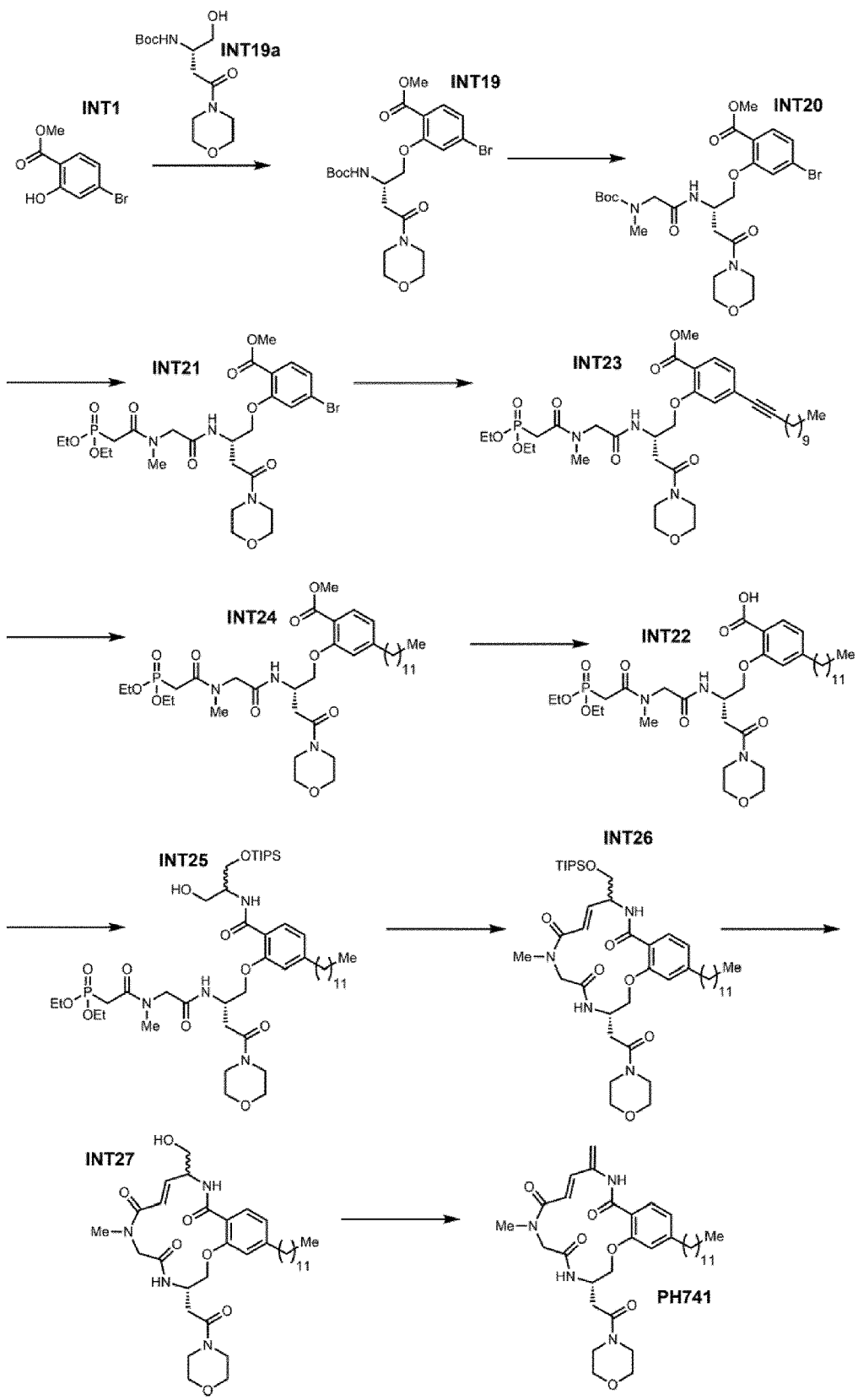
FIG. 4 shows the synthetic route to PH741.

In the following is described the synthesis of PH741 and its specific intermediates (INT) (see FIG. 4).

tert-Butyl (S)-(1-hydroxy-4-morpholino-4-oxobutan-2-yl)carbamate (INT19a)

A mixture of (S)-tert-butyl (5-oxotetrahydrofuran-3-yl) carbamate (101 mg, 1.0 equiv., 0.50 mmol) and morpholine (55 μL, 1.25 equiv., 0.625 mmol) was made in anhydrous toluene (1.0 mL) and the mixture was heated to 100° C. in an oil bath for 7 hours, without reaching full conversion of the lactone-derivative. The mixture was cooled to room temperature, before being concentrated and purified by flash column chromatography on silica gel using an elution system of dichloromethane/MeOH as follows: 100:0→2 min→100:0→16 min→85:15 (12 g column, 30 mL/min, direct load (1×3.0 mL dichloromethane to wash)) to afford the desired product as a white solid.

Methyl (S)-4-bromo-2-(2-((tert-butoxycarbonyl)amino)-4-morpholino-4-oxobutoxy)benzoate (INT19)

A suspension of methyl 4-bromo-2-hydroxybenzoate (INT1, 231 mg, 1.0 equiv., 1.00 mmol), the morpholine derivative (INT19a, 317 mg, 1.1 equiv., 1.10 mmol) and $Ph_3P$ (291 mg, 1.1 equiv., 1.10 mmol) in anhydrous toluene (5.0 mL) was made and the mixture was agitated vigorously. The mixture was placed in an ice-bath followed by dropwise addition of diethyl azodicarboxylate (40 wt % in toluene, 501 μL, 1.1 equiv., 1.10 mmol). Then, the mixture was stirred overnight while the ice-bath slowly reached room temperature. After 15 hours of reaction time, the reaction mixture was directly purified by flash column chromatography on silica gel using an elution system of Heptane/EtOAc as follows: 75:25→20 min.→25:75 (40 g column, 45 mL/min. $CH_2Cl_2$ wash (1×6 mL)).

Methyl (S)-4-bromo-2-(2-(2-((tert-butoxycarbonyl)(methyl)amino)-acetamido)-4-morpholino-4-oxobutoxy)benzoate (INT20)

The starting material carbamate derivative, an estimated (INT19, 501 mg, 1.0 equiv., 1.00 mmol) was transferred to a flame-dried one-necked flask (50 mL) equipped with a stirrer bar and the flask was placed in an ice-bath. Addition of 4 M hydrochloric acid in 1,4-dioxane (5.0 mL) was made and the mixture was stirred for 0.5 hours, at which time, TLC analysis indicated full conversion of starting material. The liberated amine derivative precipitated in the 1,4-dioxane solution upon its formation. Repeated trituration with ether (3×30 mL) allowed the isolation of the desired hydrochloride salt as a white solid.

A flame-dried, one-necked flask (50 mL) equipped with a stirrer bar under an argon atmosphere, was charged with the amine-derived hydrochloride (an estimated 372 mg, 1.0 equiv., 850 μmol), N-Boc-Sar-OH (201 mg, 1.25 equiv., 1.06 mmol) and the mixture was dissolved in dimethylformamide (6.0 mL). The reaction mixture was placed in an ice-bath, followed by the addition of TBTU (403 mg, 1.25 equiv., 1.06 mmol) and DIPEA (444 μL, 3.0 equiv., 2.55 mmol). With the addition of DIPEA, the ice-bath was removed, and the mixture was allowed to reach room temperature and was stirred under an argon atmosphere, while being followed by TLC analysis. After 4 hours, the reaction was quenched by the addition of water (75 mL) and 1 M hydrochloric acid solution (15 mL) and diluted with EtOAc (40 mL). The phases were separated, and the aqueous phase was extracted with EtOAc (3×40 mL). $Et_2O$ (20 mL) was added to help remove dimethylformamide from the organic extracts in the following washing steps. The combined organic extracts were washed with water (60 mL), saturated aqueous sodium bicarbonate (60 mL) and brine (60 mL), before being collected, dried over sodium sulphate, filtered and concentrated to afford a crude product. The crude product was purified by flash column chromatography on silica gel using an elution system of EtOAc/MeOH as follows: 100:0→2 min.→100:0→18 min.→94:6 (40 g column, 45 mL/min., $CH_2Cl_2$ load (2×4 mL)) to afford the desired product as a colorless solid.

Methyl (S)-4-bromo-2-(2-(2-(2-(diethoxyphosphoryl)-N-methylacetamido)acetamido)-4-morpholino-4-oxobutoxy)benzoate (INT21)

A one-necked flask (50 mL) equipped with a stirrer bar was charged with the starting material Boc-protected sarcosine derivative (INT20, 413 mg, 1.0 equiv., 721 μmol), and the flask was placed in an ice-bath. Addition of 4 M hydrochloric acid in 1,4-dioxane (4.0 mL) was made and the mixture was stirred for 0.5 hours, at which time, TLC analysis indicated full conversion of starting material. Repeated trituration with ether (3×35 mL) allowed the isolation of a desired hydrochloride salt as a white solid.

A flame-dried flask (50 mL) equipped with a stirrer bar under an argon atmosphere was charged with the sarcosine-derived hydrochloride (an estimated 331 mg, 1.0 equiv., 0.65 mmol) and diethylphosphonoacetic acid (131 μL, 1.25 equiv., 0.813 mmol). Addition of anhydrous dimethylformamide (4.0 mL) was made and the mixture was cooled to 0° C. using an ice bath followed by subsequent addition of TBTU (308 mg, 1.25 equiv., 0.813 mmol). Finally, addition of DIPEA (340 μL, 3.0 equiv., mmol) was made at 0° C. and the cooling was removed. The mixture was stirred overnight at room temperature and monitored by TLC analysis to deter-mine product formation. After 22 hours, the reaction was quenched using water (60 mL) and 1M aqueous hydrochloric acid solution (20 mL) and the mixture was diluted with EtOAc/ether (5:1, 60 mL). The phases were separated, and the aqueous phase was extracted with EtOAc/ether (5:1, 3×45 mL). The combined organic extracts were washed with water (50 mL), saturated aqueous sodium bicarbonate (50 mL) and brine (50 mL), before being dried over sodium sulphate and concentrated to afford a crude isolate. The crude isolate was purified by flash column chromatography on silica gel using an elution system of $CH_2Cl_2$/MeOH as follows: 100:0→2.0 min.→100:0→18 min.→85:15. (40 g column, $CH_2Cl_2$ load, 2×5 mL) to afford the desired product as an amorphous white solid.

Methyl (S)-2-(2-(2-(2-(diethoxyphosphoryl)-N-methylacetamido)-acetamido)-4-morpholino-4-oxobutoxy)-4-(dodec-1-yn-1-yl)benzoate (INT23)

A flame-dried, one-necked flask (50 mL) was charged with the bromoarene derivative (INT22, 310 mg, 1.0 equiv., 477 μmol), CuI (18 mg, 0.2 equiv., 95 μmol), $PdCl_2(PPh_3)_2$ (34 mg, 0.1 equiv., 48 μmol), and the atmosphere of the reaction vessel was evacuated and replaced with argon. Anhydrous tetrahydrofuran (4.8 mL), 1-dodecyne (204 μL, 2.0 equiv., 954 μmol) and $Et_3N$ (199 μL, 3.0 equiv., 1.43 mmol) were added and the mixture was degassed using an argon flow for 15 minutes. The mixture was heated to 50° C., and after 5 hours of reaction time, the mixture was concentrated on the rotary evaporator, before being directly purified by flash column chromatography on silica gel using an elution system of EtOAc/MeOH: 100:0→2 min.→100:

0→18 min.→80:20 (25 g column, 45 mL/min., CH$_2$Cl$_2$ load (2×3 mL)) to afford the desired product as a an amorphous white solid.

Methyl (S)-2-(2-(2-(2-(diethoxyphosphoryl)-N-methylacetamido)-acetamido)-4-morpholino-4-oxobutoxy)-4-dodecylbenzoate (INT24)

A one-necked flask (50 mL) equipped with a stirrer bar under an argon atmosphere, containing the starting material alkyne derivative (INT23, 333 mg, 1.0 equiv., 453 µmol) was charged with Pd/C (10% Pd, 24 mg, 0.05 equiv., 2 µmol). Subsequently, MeOH (4.5 mL) was added. The atmosphere in the reaction vessel was exchanged to hydrogen, and the reaction mixture was stirred overnight under a hydrogen atmosphere maintained by a balloon. After 17 hours of reaction time, the reaction mixture was filtered through a syringe filter, and the filter was washed successively with MeOH (2×15 mL) to afford the desired product as a pale-yellow sticky oil.

(S)-2-(2-(2-(2-(diethoxyphosphoryl)-N-methylacetamido)acetamido)-4-morpholino-4-oxobutoxy)-4-dodecylbenzoic acid (INT24a)

The starting material methyl ester derivative (INT24, 331 mg, 1.0 equiv., 447 µmol), was dissolved in MeOH (4.5 mL), followed by the addition of a 5 M solution of NaOH in water (450 µL, 5.0 equiv., 2.24 mmol) and the mixture was stirred at room temperature while being followed by TLC analysis. Upon reaching full conversion of starting material as indicated by TLC analysis, the mixture was poured into a separatory funnel, containing water (20 mL) and EtOAc (20 mL) before the mixture was adjusted to pH<4, using 1.0 M aqueous hydrochloric acid solution. The phases were separated and the aqueous phase was extracted with EtOAc (3×20 mL). The combined organic extracts were washed with water (20 mL) and brine (20 mL), before being dried over sodium sulphate, filtered and concentrated. The crude isolate was directly advanced in the synthesis without further purification.

Diethyl (2-((2-(((2S)-1-(5-dodecyl-2-((1-hydroxy-3-((triisopropylsilyl)oxy)propan-2-yl)carbamoyl)phenoxy)-4-morpholino-4-oxobutan-2-yl)amino)-2-oxoethyl)(methyl)amino)-2-oxoethyl)phosphonate (INT25)

To a stirring mixture of the free acid (INT24a, 320 mg, 1.0 equiv., 0.44 mmol) in anhydrous dichloromethane (3.0 mL) in a one-necked flask (50 mL) equipped with a stirrer bar, under an argon atmosphere, was added DEPBT (269 mg, 2.0 equiv., 0.88 mmol), and triethylamine (183 µL, 3.0 equiv., 1.32 mmol), followed by addition of the serinolamine (rac-INT59, 131 mg, 1.2 equiv., 0.528 mmol) in anhydrous dichloromethane (1.4 mL). After being stirred for 3 hours at room temperature, the reaction was quenched by addition of water (60 mL) and 1.0 M aqueous HCl solution (10 mL), then the mixture was diluted with EtOAc (40 mL) and the layers were separated. The aqueous phase was extracted with EtOAc (3×40 mL). The combined organic phases were washed with 1 M aqueous HCl (20 mL) and water (60 mL×2), 10% aqueous potassium carbonate (2×40 mL), and brine (40 mL), before being dried over sodium sulphate, filtered and concentrated to afford a crude isolate. The crude material was purified by flash column chromatography on silica gel using an elution system of dichloromethane/MeOH as follows: CH$_2$Cl$_2$/MeOH 100:0→2 min.→CH$_2$Cl$_2$/MeOH 100:0→28 min.→EtOAc/MeOH 92:8, (25 g column, 30 mL/min., CH$_2$Cl$_2$ load (2×3.5 mL)) to afford the desired product as a clear sticky oil.

(3S,E)-16-dodecyl-7-methyl-3-(2-morpholino-2-oxoethyl)-11-(((triisopropylsilyl)oxy)methyl)-3,4,6,7,11,12-hexahydrobenzo[n][1]oxa[4,7,12]triazacyclopentadecine-5,8,13(2H)-trione (INT26)

To a stirring solution of the phosphonate alcohol (INT25, 126 mg, 1.0 equiv. 133 µmol) in dichloromethane (3.0 mL) in a one-necked flask (10 mL) equipped with a stirrer bar was added Dess-Martin periodinane (112 mg, 2.0 equiv., 266 µmol). After stirring the mixture for 1.0 hour at ambient temperature, the reaction was poured into a separatory funnel containing saturated aqueous NaHCO$_3$ (10 mL) and saturated aqueous Na$_2$S$_2$O$_3$ (10 mL), using dichloromethane (17 mL) to wash the reaction vessel and dilute the organic phase in the separatory funnel. The mixture was shaken vigorously until the organic phase became clear. The organic phase was diluted with dichloromethane (15 mL), and water (15 mL) and the layers were separated. The aqueous phase was extracted with dichloromethane (3×20 mL). The combined organic extracts were washed with brine (20 mL), dried over sodium sulphate, filtered, and concentrated. The crude product was directly advanced in the synthetic sequence. The aldehyde precursor directly applied from the oxidation step (an estimated 127 mg, 1.0 equiv., 133 µmol) was dissolved in anhydrous tetrahydrofuran (60 mL) in a one-necked flask (250 mL) equipped with a stirrer bar under an argon atmosphere, and anhydrous Et$_3$N (92 µL, 5.0 equiv., 0.665 mmol) was added followed immediately by TMEDA (40 µL, 2.0 equiv., 266 µmol) and Zn(OTf)$_2$ (197 mg, 4.0 equiv., 532 µmol). The mixture was left stirring at room temperature for 3 hours. The reaction was quenched with water (40 mL) followed by the addition of brine (40 mL) and 1.0 M aqueous HCl solution (20 mL), before EtOAc (100 mL) was added to the mixture. The mixture was poured into a separatory funnel and the layers were separated. The aqueous phase was extracted with EtOAc (3×60 mL). The combined organic phases were washed with brine (60 mL), 1 M aqueous potassium carbonate (60 mL) and brine (60 mL) before being dried over sodium sulphate, filtered and concentrated to afford a crude isolate. The crude material was purified by flash column chromatography using an elution system of CH$_2$Cl$_2$/MeOH as follows: 100:0→2 min.→100:0→23 min.→92:8 (12 g column, CH$_2$Cl$_2$ load (2×2.0 mL), 30 mL/min.). The desired product was afforded as a mixture of diastereoisomers as a sticky colorless solid.

(3S,E)-16-dodecyl-11-(hydroxymethyl)-7-methyl-3-(2-morpholino-2-oxoethyl)-3,4,6,7,11,12-hexahydrobenzo[n][1]oxa[4,7,12]-triazacyclopentadecine-5,8,13(2H)-trione (INT27)

The macrocyclic silyl-protected compound, as a mixture of diastereoisomers (INT26, 63 mg, 1.0 equiv., 78 µmol) was dissolved in anhydrous tetrahydrofuran (2.0 mL) under an argon atmosphere and the mixture was cooled to 0° C. Addition of tetrabutylammonium fluoride (1M in tetrahydrofuran, 98 µL, 1.25 equiv., 98 µmol) was made dropwise at 0° C. and the reaction mixture was stirred at room temperature for an additional 1 hour. The reaction was quenched by the addition of water (20 mL), and the reaction mixture was diluted with dichloromethane (20 mL). The phases were separated, and the aqueous phase was extracted with dichloromethane (3×20 mL). The combined organic phases were washed with brine (2×20 mL) before being dried over sodium sulphate, filtered, and concentrated to afford a crude isolate. The crude isolate was purified by flash column chromatography on silica gel using an elution system of dichloromethane/MeOH as follows: 100:0→2.5 min.→100:0→20 min.→75:25 (4 g column, 30 mL/min., dichloromethane load (2×3.5 mL)) to afford the desired product as a white amorphous solid.

(S,E)-16-dodecyl-7-methyl-11-methylene-3-(2-morpholino-2-oxoethyl)-3,4,6,7,11,12-hexahydrobenzo[n][1]oxa[4,7,12]triazacyclopentadecine-5,8,13(2H)-trione (PH741)

The starting material alcohol as a mixture of diastereoisomers (INT27, 6 mg, 1.0 equiv., 9 μmol) was dissolved in anhydrous acetonitrile/tetrahydrofuran (0.5:0.5 mL) under an argon atmosphere, to become a colorless, clear solution. Addition of DSC (5 mg, 2.0 equiv., 19 μmol) and DIPEA (5 μL, 3.0 equiv., 28 μmol) was made to the reaction mixture at room temperature. The reaction was stirred for 18 hours at 45° C. The reaction mixture was cooled to room temperature before being concentrated using a flow of nitrogen. The crude product was purified by flash column chromatography on silica gel using an elution system of dichloromethane/MeOH 100:0→2 min.→100:0→21:20 min.→90:10 (4 g column, $CH_2Cl_2$ load (2×1 mL, 15 mL/min.)). Following concentration and lyophilization, the desired product was afforded as a flocculent white solid. $^1$H NMR (500 MHz, DMSO-$d_6$) δ=9.04 (s, 1H), 8.43 (d, J=5.9 Hz, 1H), 7.79 (d, J=7.9, 1H), 7.16 (s, 1H), 6.95 (d, J=15.3 Hz, 1H), 6.91 (d, J=8.0 Hz, 1H), 6.35 (d, J=15.3 Hz, 1H), 6.18 (s, 1H), 5.29 (s, 1H), 4.33 (d, J=10.2 Hz, 1H), 4.25 (d, J=10.3 Hz, 1H), 4.09 (d, J=17.3, 1H), 3.90 (d, J=17.3, 1H), 3.59-3.34 (m, 9H), 2.99 (s, 3H), 2.72-2.65 (m, 2H), 2.60 (t, J=7.4, 2H), 1.61-1.53 (m, 2H), 1.27-1.18 (m, 18H), 0.82 (t, J=6.8, 3H).

Example 5—Synthesis of PH832

Figure 5:
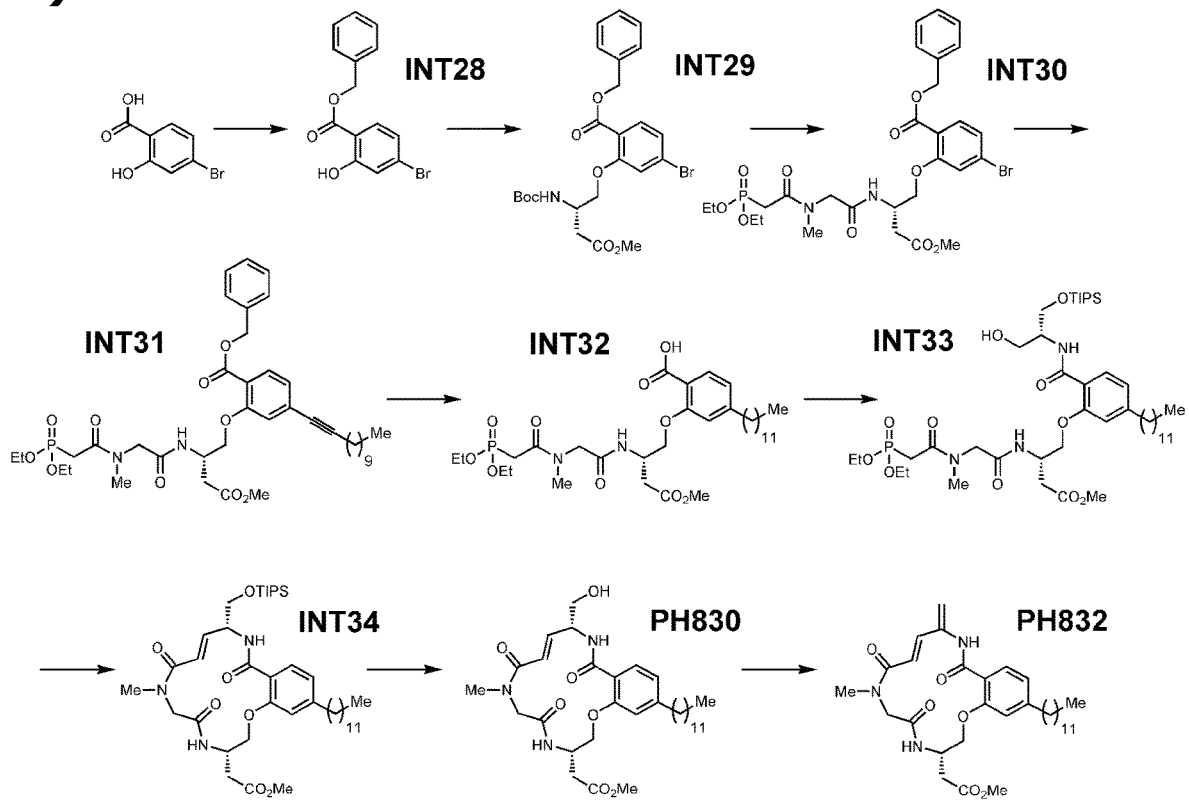
FIG. 5 shows in A) the synthetic route to PH832 and the negative control compound PH830; B) the synthetic route from PH830 to PH845.
Figure 5:
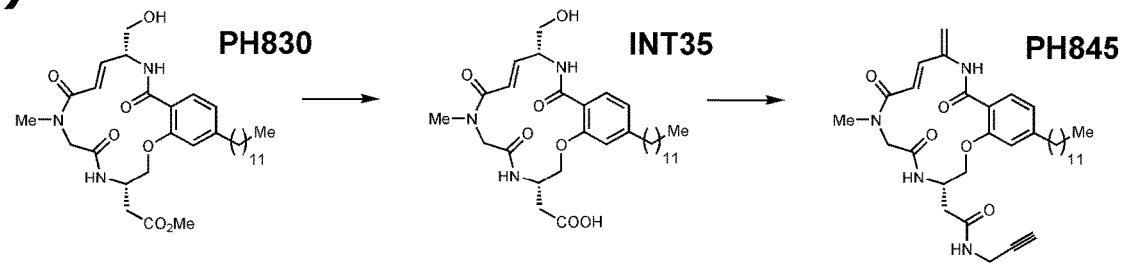

In the following is described the synthesis of PH832 and its specific intermediates (INT) (see FIG. 5A).

Benzyl 4-bromo-2-hydroxybenzoate (INT28)

A solution of $NaHCO_3$ (2.02 g, 1.20 equiv., 24.0 mmol) and 4-bromosalicylic acid (4.34 g, 1.0 equiv., 20.0 mmol) in anhydrous dimethylformamide (26.0 mL) in a flame-dried one-necked flask (100 mL) equipped with a stirrer bar under an argon atmosphere and the resulting mixture was stirred at 70° C. for 10 minutes before the temperature was reduced to 50° C. Subsequent addition of benzyl bromide (1.0 mL, 1.05 equiv., 8.4 mmol) was made dropwise. The reaction mixture was stirred for 2 hours at 50° C. and then allowed to cool to room temperature. $H_2O$ (200 mL) was added and the crude product was extracted with $EtOAc:Et_2O$ 1:1 (3×100 mL). The combined EtOAc extracts were washed with water (100 mL) and brine (100 mL), dried over anhydrous $Na_2SO_4$ and concentrated to afford a crude isolate. The crude isolate was purified by flash column chromatography on silica gel using an elution system of Heptane/EtOAc as follows: 100:0→95:5→90:10 to afford the desired product as a clear oil.

Benzyl (S)-4-bromo-2-(2-((tert-butoxycarbonyl)amino)-4-methoxy-4-oxobutoxy)benzoate (INT29)

To a stirred solution of benzyl 4-bromo-2-hydroxybenzoate (INT28, 1.23 g, 1.0 equiv., 4.00 mmol), the Boc-protected amino alcohol, (3S)-3-[(tert-butoxycarbonyl)amino]-4-hydroxybutanoic acid methyl ester (1.03 g, 1.1 equiv., 4.40 mmol) and $Ph_3P$ (1.13 g, 1.1 equiv., 4.40 mmol) in anhydrous toluene (16 mL) and the mixture was cooled to 0° C., diethyl azodicarboxylate (40 wt % in toluene, 2.00 mL, 1.10 equiv., 4.40 mmol) was added dropwise at 0° C. and the reaction mixture was stirred at room temperature. After 2.5 hours, the mixture was directly purified by flash column chromatography on silica gel using an elution system of Heptane/EtOAc as follows: 100:0→2 min.→100:0→28 min→65:35 (80 g column, 45 mL/min., direct load (5.0 mL $CH_2Cl_2$ to wash the reaction vessel)) to afford the desired product as a clear sticky oil.

Benzyl (S)-4-bromo-2-(2-(2-(2-(diethoxyphosphoryl)-N-methylacetamido)acetamido)-4-methoxy-4-oxobutoxy)benzoate (INT30)

The starting material carbamate derivative, (INT29, 1.99 g, 1.0 equiv., 3.81 mmol) was placed a flame-dried one-necked flask (100 mL) equipped with a stirrer bar and the flask was placed in an ice-bath. Addition of 4 M hydrochloric acid in 1,4-dioxane (9.5 mL) was made at 0° C. and the mixture was stirred for 0.5 hours at room temperature, at which time, TLC analysis indicated full conversion of starting material. Repeated addition of $Et_2O$ (2×50 mL) and concentration afforded the amine hydrochloride as a white solid, that was used directly in the subsequent coupling step. A flame-dried flask (100 mL) equipped with a stirrer bar under an argon atmosphere was charged with the amine hydrochloride (approximately 1.7 g, 1.0 equiv., 3.81 mmol) and diethylphosphonoacetic acid (1.27 g, 1.25 equiv., 4.76 mmol). Addition of anhydrous dimethylformamide (19.1 mL) was made and the mixture was cooled to 0° C. using an ice bath followed by subsequent addition of TBTU (1.81 g, 1.25 equiv., 4.76 mmol). Finally, addition of DIPEA (1.99 mL, 3.0 equiv., 11.4 μmol) was made at 0° C. and the reaction mixture was slowly allowed to reach room temperature overnight. The mixture was monitored by TLC analysis to determine product formation. Upon completion, the reaction was quenched with water (50 mL) and 1 M aqueous hydrochloric acid solution (25 mL) and the mixture was diluted with EtOAc/ether (3:1, 60 mL). The phases were separated, and the aqueous phase was extracted with EtOAc/ether (3:1, 3×40 mL). The combined organic extracts were washed with water (40 mL), saturated aqueous sodium bicarbonate (40 mL) and brine (40 mL), before being dried over sodium sulphate and concentrated to afford a crude isolate. The crude isolate was purified by flash column chromatography on silica gel using an elution system of $CH_2Cl_2$/iPrOH as follows: 100:0 (0 min.)→100:0 (1 min.)→85:15 (30 min.) (80 g column, 45 mL/min., $CH_2Cl_2$ load, 2×4.0 mL), to afford the desired product as an amorphous sticky solid.

Benzyl (S)-2-(2-(2-(2-(diethoxyphosphoryl)-N-methylacetamido)-acetamido)-4-methoxy-4-oxobutoxy)-4-(dodec-1-yn-1-yl)benzoate (INT31)

A flame-dried, one-necked flask (100 mL) was charged with the bromoarene derivative (INT30, 2.44 g, 1.0 equiv., 3.64 mmol), CuI (139 mg, 0.2 equiv., 728 μmol), $PdCl_2(PPh_3)_2$ (255 mg, 0.1 equiv., 364 μmol), and the atmosphere of the reaction vessel was evacuated and replaced with argon. Anhydrous tetrahydrofuran (18.2 mL), 1-dodecyne (1.56 mL, 2.0 equiv., 7.28 mmol) and $Et_3N$ (1.52 mL, 3.0 equiv., 10.9 mmol) was added. The mixture was heated to 50° C., and after 6 hours of reaction time, the mixture was concentrated on the rotary evaporator, before being directly purified by flash column chromatography on silica gel using an elution system of CH$_2$Cl$_2$/iPrOH: 100:0 (0 min.)→100:0 (1 min.)→88:12 (25 min.) (80 g column, 60 mL/min., CH$_2$Cl$_2$ load (2×5 mL)) to afford the desired product as a brownish sticky oil.

(S)-2-(2-(2-(2-(diethoxyphosphoryl)-N-methylacetamido)acetamido)-4-methoxy-4-oxobutoxy)-4-dodecylbenzoic acid (INT32)

A one-necked flask (50 mL) equipped with a stirrer bar under an argon atmosphere, containing the starting material alkyne derivative (INT31 2.49 g, 1.0 equiv., 3.29 mmol) was charged with Pd/C (10% Pd, 175 mg, 0.05 equiv., 165 µmol). Subsequently, MeOH (16.5 mL) was added. The atmosphere in the reaction vessel was exchanged to hydrogen, and the reaction mixture was stirred overnight under a hydrogen atmosphere maintained by a balloon. After 17 hours of reaction time, the reaction mixture was filtered through a PTFE syringe filter, and the filter was washed successively with MeOH (2×15 mL). This procedure was conducted twice, to afford the desired product as a pale-yellow sticky oil.

Methyl (S)-3-(2-(2-(diethoxyphosphoryl)-N-methylacetamido)-acetamido)-4-(5-dodecyl-2-(((R)-1-hydroxy-3-((triisopropylsilyl)-oxy)propan-2-yl)carbamoyl)phenoxy)butanoate (INT33)

To a stirring mixture of the free acid (INT32, 1.81 g, 1.00 equiv., 2.70 mmol) in anhydrous dichloromethane (7.5 mL) in a one-necked flask (50 mL) equipped with a stirrer bar, under an argon atmosphere, was added DEPBT (1.65 g, 2.0 equiv., 5.40 mmol), and triethylamine (1.13 mL, 3.0 equiv., 8.10 mmol), followed by addition of the serinolamine ((R)-INT59, 802 mg, 1.2 equiv., 3.24 mmol) in anhydrous dichloromethane (6.0 mL). After being stirred for 6 hours at room temperature, the reaction was quenched by addition of water (50 mL) and 1 M aqueous hydrochloric acid solution (25 mL), the mixture was diluted with EtOAc (60 mL) and the layers were separated. The aqueous phase was extracted with EtOAc (3×40 mL). The combined organic phases were washed with water (50 mL), 1 M aqueous potassium carbonate (2×50 mL), and brine (50 mL), dried over sodium sulphate, filtered, and concentrated to afford a crude isolate. The crude material was purified by flash column chromatography on silica gel using an elution system of Heptane/EtOAc/iPrOH as follows: 50:50:0 (0 min.)→50:50:0 (1 min.)→0:100:0 (25 min.)→0:100:0 (35 min.)→0:88:12 (45 min.)→0:88:12 (50 min.), 80 g column, 45 mL/min., dichloromethane load (2×4.0 mL), to afford the desired product as a clear sticky oil with a yellow discoloration.

Methyl 2-((3S,11R,E)-16-dodecyl-7-methyl-5,8,13-trioxo-11-(((triisopropylsilyl)oxy)methyl)-2,3,4,5,6,7,8,11,12,13-decahydrobenzo-[n][1]oxa[4,7,12]triazacyclopentadecin-3-yl)acetate (INT34)

To a stirring solution of the phosphonate alcohol (INT33, 1.04 g, 1.0 equiv. 1.16 µmol) in dichloromethane (23.2 mL) in a one-necked flask (50 mL) equipped with a stirrer bar was added Dess-Martin periodinane (984 mg, 2.0 equiv., 2.32 mmol). After stirring the mixture for 1.0 hour at ambient temperature, the reaction was poured into a separatory funnel containing saturated aqueous NaHCO$_3$ (15 mL) and saturated aqueous Na$_2$S$_2$O$_3$ (15 mL), using dichloromethane (20 mL) to wash the reaction vessel and dilute the organic phase in the separatory funnel. The mixture was shaken vigorously until the organic phase became clear. The aqueous phase was extracted with dichloromethane (3×15 mL). The combined organic extracts were washed with brine (20 mL), dried over sodium sulphate, filtered, and concentrated. The crude product was directly advanced in the synthetic sequence. A one-necked flask (250 mL) equipped with a stirrer bar under an argon atmosphere, was charged with anhydrous Et$_3$N (484 µL, 3.0 equiv., 3.48 mmol), TMEDA (220 µL, 1.25 equiv., 1.45 mmol) and Zn(OTf)$_2$ (1.076 mg, 2.5 equiv., 2.90 mmol) in anhydrous tetrahydrofuran (46 mL). The aldehyde precursor directly applied from the oxidation reaction (approximately 1.1 g, 1.0 equiv., 1.16 mmol) was dissolved in anhydrous tetrahydrofuran (46 mL) and was added to the aforementioned solution using a syringe pump over 1 hour. Subsequently, the mixture was left stirring at room temperature for 1 hour. The reaction was quenched with water (40 mL) followed by the addition of brine (40 mL) and 1.0 M aqueous HCl solution (20 mL), before EtOAc (40 mL) was added to the mixture. The mixture was poured into a separatory funnel and the layers were separated, the aqueous phase was extracted with EtOAc (3×40 mL). The combined organic phases were washed with water/brine 4:1 (50 mL), 1 M aqueous potassium carbonate/brine 4:1 (50 mL) and brine (50 mL) before being dried over sodium sulphate, filtered and concentrated to afford a crude isolate. The crude material was purified by flash column chromatography using an elution system of Heptane/acetone as follows: 90:10 (0 min.)→90:10 (1 min.)→50:50 (22 min.) (40 g column, dichloromethane load (2×5.0 mL), 60 mL/min.). The desired product was afforded as an amorphous colorless solid.

Methyl 2-((3S,11R,E)-16-dodecyl-11-(hydroxymethyl)-7-methyl-5,8,13-trioxo-2,3,4,5,6,7,8,11,12,13-decahydrobenzo[n][1]oxa[4,7,12]-triazacyclopentadecin-3-yl)acetate (PH830)

The macrocyclic silyl-protected compound (INT34, 153 mg, 1.0 equiv., 205 µmol) was dissolved in anhydrous tetrahydrofuran (4.1 mL) under an argon atmosphere and the mixture was cooled to 0° C. Addition of tetrabutylammonium fluoride (1 M in tetrahydrofuran, 308 µL, 1.5 equiv., 308 µmol) was made dropwise at 0° C. and the reaction mixture was stirred at room temperature for an additional 1.5 hours. The reaction was quenched by the addition of water (20 mL), and the mixture was diluted with dichloromethane (20 mL) and brine (10 mL). The phases were separated, and the aqueous phase was extracted with dichloromethane (3×20 mL). The combined organic phases were washed with brine (20 mL) before being dried over sodium sulphate, filtered and concentrated to afford a crude isolate. The crude isolate was purified by flash column chromatography on silica gel using an elution system of dichloromethane/iPrOH as follows: 100:0 (0 min.)→100:0 (1 min.)→70:30 (20 min.) (12 g column, 45 mL/min., dichloromethane load (2×4 mL)) to afford the desired product as a colorless amorphous solid.

Methyl (S,E)-2-(16-dodecyl-7-methyl-11-methylene-5,8,13-trioxo-2,3,4,5,6,7,8,11,12,13-decahydrobenzo[n][1]oxa[4,7,12]-triazacyclopentadecin-3-yl)acetate (PH832)

The starting material alcohol (PH830, 24 mg, 1.0 equiv., 40 µmol) was dissolved in anhydrous acetonitrile/tetrahydrofuran (1:1, 3 mL) under an argon atmosphere. Addition of DSC (22 mg, 2.0 equiv., 80 µmol) and DIPEA (21 µL, 3.0 equiv., 120 µmol) was made to the reaction mixture at room temperature. The reaction was stirred for 17 hours at 45° C. as a colorless, clear solution. After 17 hours, conversion was estimated at approximately 50%, subsequent addition of DSC (22 mg, 2.0 equiv., 80 µmol) and DIPEA (21 µL, 3.0 equiv., 120 µmol) was made to the reaction mixture. After a subsequent 4 hours of reaction time, the reaction appeared to be at approximately 90% conversion with the desired elimination product being the major reaction product based on TLC analysis. The reaction mixture was cooled to room temperature before being concentrated using a flow of nitrogen. The crude product was purified by preparative TLC followed by collection and lyophilization, to afford the desired product as a white flocculent solid. $^1$H NMR (400 MHz, DMSO-$d_6$) δ=9.03 (s, 1H), 8.47 (d, J=5.9 Hz, 1H), 7.81 (d, J=8.0 Hz, 1H), 7.08 (s, 1H), 7.00 (d, J=15.4 Hz, 1H), 6.95 (d, J=8.6 Hz, 1H), 6.38 (d, J=15.4 Hz, 1H), 6.19 (s, 1H), 5.34 (s, 1H), 4.38 (t, J=10.3 Hz, 1H), 4.27 (d, J=10.2 Hz, 1H), 4.15 (d, J=17.1 Hz, 1H), 3.93 (d, J=17.1 Hz, 1H), 3.63 (s, 3H), 3.02 (s, 3H), 2.63 (t, J=7.8 Hz, 2H), 2.00 (dd, J=6.8 Hz, 6.1 Hz, 2H), 1.65-1.55 (m, 2H), 1.33-1.18 (m, 18H), 0.85 (t, J=6.6 Hz, 3H).

Example 6—Synthesis of PH845

In the following is described the synthesis of PH845 and its specific intermediates (INT) that are not described in the synthesis of PH832 (see FIG. 5B).

2-((3S,11R,E)-16-dodecyl-11-(hydroxymethyl)-7-methyl-5,8,13-trioxo-2,3,4,5,6,7,8,11,12,13-decahydrobenzo[n][1]oxa[4,7,12]-triazacyclopentadecin-3-yl)acetic acid (INT35)

The starting material methyl ester (PH830, 45 mg, 1.0 equiv., 0.077 µmol), was dissolved in a mixture of tetrahydrofuran (3.5 mL), H$_2$O (0.7 mL) and MeOH (0.7 mL), followed by the addition of LiOH·H$_2$O (16 mg, 5.0 equiv., 0.385 mmol) and the mixture was stirred at room temperature while being followed by TLC analysis. Upon reaching full conversion of starting material as indicated by TLC analysis, the mixture was poured into a separatory funnel, containing water (20 mL), brine (10 mL) and EtOAc (20 mL) before the mixture was adjusted to pH<4, using 1.0 M aqueous hydrochloric acid solution. The phases were separated, and the aqueous phase was extracted with EtOAc (3×20 mL). The combined organic extracts were washed with water (20 mL) and brine (20 mL), before being dried over sodium sulphate, filtered and concentrated. The crude isolate was directly utilizing in the following coupling step without further purification.

(S,E)-2-(16-dodecyl-7-methyl-11-methylene-5,8,13-trioxo-2,3,4,5,6,7,8,11,12,13-decahydrobenzo[n][1]oxa[4,7,12]-triazacyclopentadecin-3-yl)-N-(prop-2-yn-1-yl)acetamide (PH845)

To the starting material, (INT35, an estimated 44 mg, 1.00 equiv., 77 µmol) in a one-necked flask (25 mL) equipped with a stirrer bar under an argon atmosphere, was added propargylamine (10 µL, 2.0 equiv., 154 µmol), followed by anhydrous dichloromethane (1.5 mL). Subsequent addition of HATU (59 mg, 2.0 equiv., 154 µmol) was made at room temperature, followed by addition of DIPEA (40 µL, 3.0 equiv., 231 µmol). The mixture was stirred at room temperature. Upon completion, the mixture was poured into a separatory funnel containing EtOAc (20 mL), water (10 mL) and 1 M hydrochloric acid solution (5 mL) and brine (25 mL). The phases were separated and the aqueous phase was extracted using EtOAc (3×20 mL). The combined organic extracts were washed with brine (20 mL), before being dried over sodium sulphate, filtered, and concentrated to afford a crude isolate. The crude isolate was purified by flash column chromatography on silica gel using an elution system of dichloromethane/i-PrOH as follows: 100:0 (0 min.)→100:0 (1 min.)→75:25 (20 min.), 12 g column, 30 ml/min., CH$_2$Cl$_2$/iPrOH (3.0 mL:0.25) mL, then CH$_2$Cl$_2$ (3.0 mL) to load the crude product as a clear solution, upon concentration, a mixture containing the desired product was afforded. Subsequent preparative TLC was performed after loading the mixture onto the preparative TLC plate using tetrahydrofuran (2.0 mL). The relevant band was collected, and the compound eluted using a mixture of CH$_2$Cl$_2$/MeOH 75:25 (40 mL). The material was transferred to a pre-weighed falcon tube (15 mL) using tetrahydrofuran/iPrOH 3:1 (2 mL) and was concentrated using a nitrogen flow. Resuspension in acetonitrile/H$_2$O (4:1, 5.0 mL) and lyophilization afforded the desired product as a flocculent white solid. $^1$H NMR (400 MHz, DMSO-$d_6$) δ=9.10 (s, 1H), 8.47 (t, J=5.5, 1H), 8.44 (d, J=6.6, 1H), 7.83 (d, J=7.9, 1H), 7.11 (s, 1H), 6.99 (d, J=15.4, 1H), 6.95 (d, J=8.1, 1H), 6.37 (d, J=15.3, 1H), 6.21 (s, 1H), 5.34 (s, 1H), 4.44 (d, J=10.3, 1H), 4.28 (d, J=10.3, 1H), 4.25-4.19 (m, 1H), 4.12 (d, J=17.3, 1H), 3.95 (d, J=17.3, 1H), 3.92-3.85 (m, 2H), 3.12 (t, J=2.5, 1H), 3.03 (s, 3H), 2.64 (t, J=7.7, 2H), 2.06-1.93 (m, 2H), 1.67-1.54 (m, 2H), 1.24 (s, 18H), 0.86 (t, J=6.6, 3H).

Example 7—Synthesis of PH906

Figure 6:
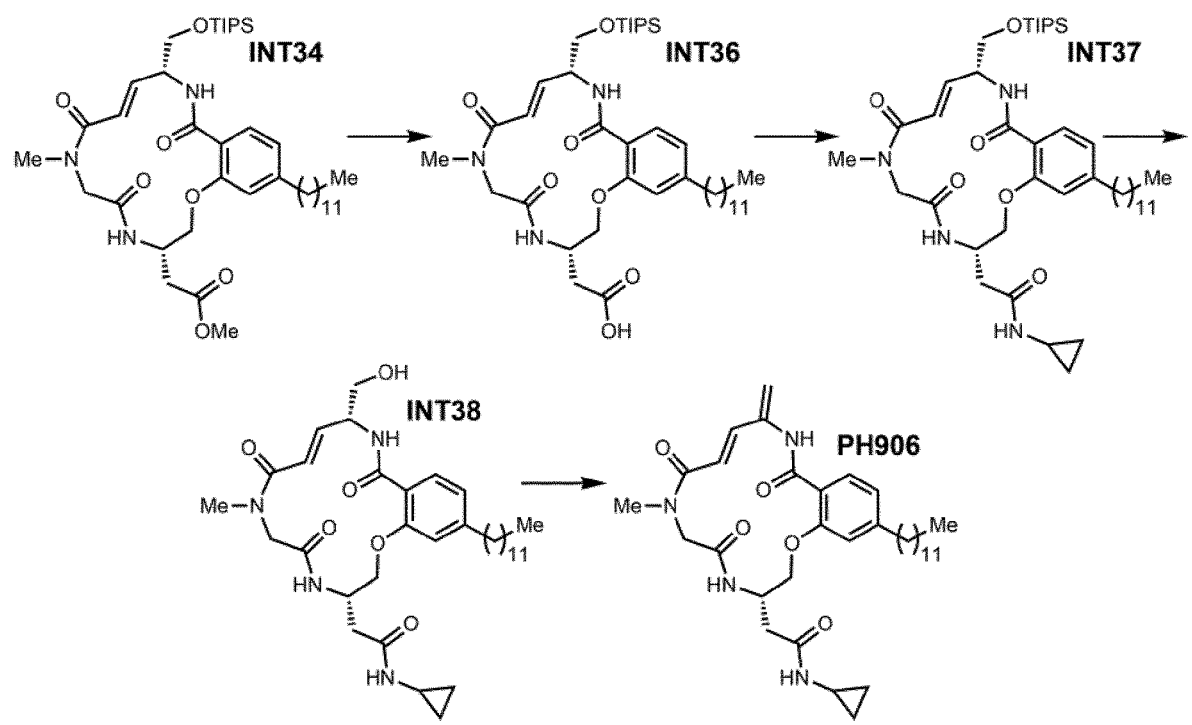
FIG. 6 shows the synthetic route to PH906.

In the following is described the synthesis of PH906 and its specific intermediates (INT) that are not described in the synthesis of PH832 (see FIG. 5A and FIG. 6).

2-((3S,11R,E)-16-Dodecyl-7-methyl-5,8,13-trioxo-11-(((triisopropylsilyl)oxy)methyl)-2,3,4,5,6,7,8,11,12,13-decahydrobenzo-[n][1]oxa[4,7,12]triazacyclopentadecin-3-yl)acetic acid (INT36)

The starting material methyl ester (INT34, 201 mg, 1.0 equiv., 270 µmol), was dissolved in a mixture of tetrahydrofuran (3.0 mL), H$_2$O (0.50 mL) and MeOH (0.50 mL), followed by the addition of LiOH—H$_2$O (17 mg, 1.5 equiv., 405 µmol) and the mixture was stirred at room temperature while being followed by TLC analysis. Upon reaching full conversion of starting material as indicated by TLC analysis, the reaction was quenched into a separatory funnel containing saturated aqueous ammonium chloride solution (20 mL), followed by the addition of water (10 mL). The resulting mixture diluted with EtOAc (80 mL) and the phases were separated. The organic extract was washed with brine (20 mL) before being dried over sodium sulphate, filtered, and concentrated to afford a crude product. The crude product was purified by flash column chromatography on silica gel using an isocratic elution system of EtOAc+0.2% AcOH, 12 g column, 30 mL/min, 22 min, to afford the desired product as an amorphous solid.

N-cyclopropyl-2-((3S,11R,E)-16-dodecyl-7-methyl-5,8,13-trioxo-11-(((triisopropylsilyl)oxy)methyl)-2,3,4,5,6,7,8,11,12,13-decahydrobenzo-[n][1]oxa[4,7,12]triazacyclopentadecin-3-yl)acetamide (INT37)

The starting material acid derivative (INT36, 117 mg, 1.0 equiv., 160 µmol) was dissolved in anhydrous dichloromethane (3.2 mL), in a one-necked flask equipped with a stirrer bar under an argon atmosphere. Addition of cyclopropylamine (22 µL, 2.0 equiv., 320 µmol) was made followed by sequential addition of HATU (122 mg, 2.0 equiv., 320 µmol) and DIPEA (111 µL, 4.0 equiv., 640 µmol). The resulting mixture was stirred at room temperature while being followed by TLC analysis. Upon completion, the mixture was transferred to a separatory funnel containing water (20 mL) and 1 M aqueous hydrochloric acid solution (10 mL) and EtOAc (10 mL). EtOAc (10 mL) was used to allow quantitative transfer of the material from the reaction vessel into the separatory funnel. The phases were separated, and the aqueous phase was extracted using EtOAc (3×20 mL). The combined organic extracts were washed with water/brine 1:1 (40 mL), before being dried over sodium sulphate, filtered, and concentrated to afford a crude isolate. The crude isolate was purified by flash column chromatography on silica gel using an elution system of EtOAc/MeOH as follows: 100:0 (0 min)→100:0 (1 min)→94:6 (16 min), 12 g column, 30 mL/min, EtOAc load (2×3.0 mL, not loaded as a clear solution) to afford the desired product as a colorless solid.

N-cyclopropyl-2-((3S,11R,E)-16-dodecyl-11-(hydroxymethyl)-7-methyl-5,8,13-trioxo-2,3,4,5,6,7,8,11,12,13-decahydrobenzo[n][1]oxa[4,7,12]-triazacyclopentadecin-3-yl)acetamide (INT38)

The starting material silyl-ether (INT37, 110 mg, 1.0 equiv., 143 µmol), was charged into a one-necked flask (25 mL) equipped with a stirrer bar under an argon atmosphere. The starting material was dissolved in anhydrous tetrahydrofuran (2.9 mL) and the solution was cooled to 0° C. in an ice-bath. Subsequent addition of TBAF (1 M solution in tetrahydrofuran, 214 µL, 1.5 equiv., 214 µmol) was made at 0° C. and subsequently, the ice-bath was removed, and the mixture was stirred at room temperature. After 1 hour of reaction time, addition of Et$_2$O (5.0 mL) was made and the solution was concentrated using a stream of nitrogen to afford a crude product. The crude product was purified by flash column chromatography on silica gel using an elution system of dichloromethane/MeOH as follows: 100:0 (0 min)→100:0 (1 min)→85:15 (16 min), 12 g column, 30 mL/min, dichloromethane load (2×2.0 mL), to afford the desired product as an amorphous colorless solid.

(S,E)-N-cyclopropyl-2-(16-dodecyl-7-methyl-11-methylene-5,8,13-trioxo-2,3,4,5,6,7,8,11,12,13-decahydrobenzo[n][1]oxa[4,7,12]-triazacyclopentadecin-3-yl)acetamide (PH906)

The starting material alcohol (INT38, 20 mg, 1.0 equiv., 33 µmol) was dissolved in anhydrous MeCN/tetrahydrofuran (1.0:1.0 mL) under an argon atmosphere, to become a colorless, clear solution. Addition of DSC (18 mg, 2.0 equiv., 65 µmol) and DIPEA (17 µL, 3.0 equiv., 98 µmol) was made to the reaction mixture at room temperature. The reaction was stirred for 20 hours at 45° C. The reaction mixture was cooled to room temperature before being concentrated using a flow of nitrogen. The crude product was analysed by 1H-NMR spectroscopy to evaluate product formation. The crude product was purified by preparative HPLC using an elution system of acetonitrile/water, followed by concentration, to afford the desired product as a colorless solid. $^1$H NMR (400 MHz, DMSO-d$_6$) δ=9.11 (s, 1H), 8.43 (d, J=6.2 Hz, 1H), 8.05 (d, J=4.2 Hz, 1H), 7.84 (d, J=7.9 Hz, 1H), 7.11 (s, 1H), 6.99 (d, J=15.4 Hz, 1H), 6.96 (d, J=8.0 Hz, 1H), 6.37 (d, J=15.4 Hz, 1H), 6.21 (s, 1H), 5.34 (s, 1H), 4.43 (t, J=10.3 Hz, 1H), 4.27 (dd, J=10.6 Hz, 2.3 Hz, 1H), 4.21 (s, 1H), 4.12 (d, J=17.3 Hz, 1H), 3.95 (d, J=17.2 Hz, 1H), 3.03 (s, 3H), 2.69-2.58 (m, 3H), 1.68-1.55 (m, 2H), 1.34-1.19 (m, 18H), 0.86 (t, J=7.0 Hz, 3H), 0.66-0.56 (m, 2H), 0.45-0.36 (m, 2H). The signals from two protons were convoluted with the residual solvent peak Example 8—Synthesis of PH905

Figure 7:
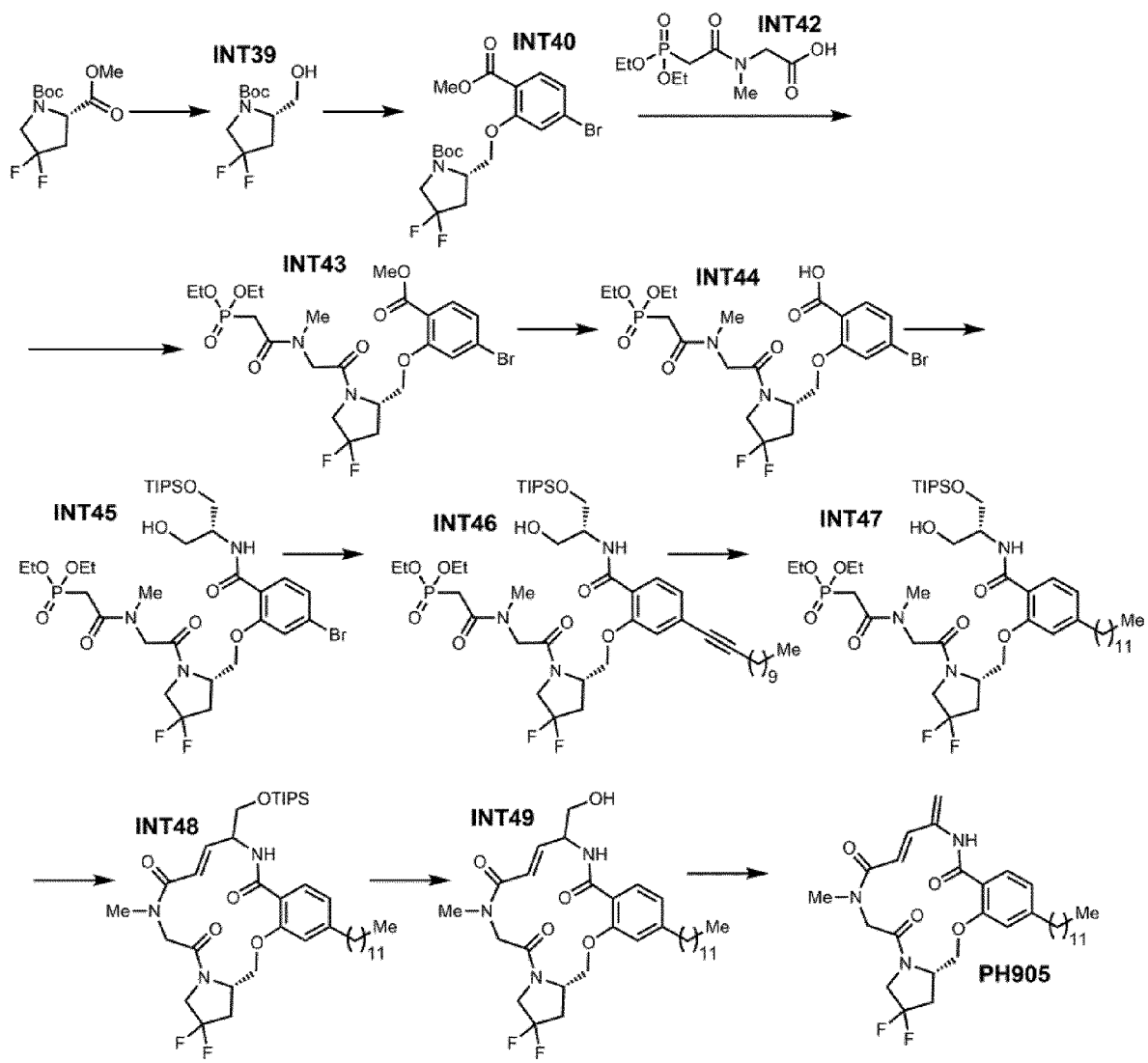
FIG. 7 shows the synthetic route to PH905.

In the following is described the synthesis of PH905 and its specific intermediates (INT) (see FIG. 7).

tert-butyl (S)-4,4-difluoro-2-(hydroxymethyl)pyrrolidine-1-carboxylate (INT39)

The starting material ester, 1-(tert-butyl) 2-methyl (S)-pyrrolidine-1,2-dicarboxylate, was charged into a flame-dried, one-necked flask (100 mL) equipped with a stirrer bar under an argon atmosphere. The starting material (1.59 g, 1.0 equiv., 6.00 mmol) was dissolved in tetrahydrofuran (12 mL) and the solution was cooled to 0° C. in an ice-bath. Subsequent addition of lithium borohydride (327 mg, 2.5 equiv., 15.0 mmol) was made, and the reaction was stirred at room temperature overnight. The reaction was quenched using 1 M hydrochloric acid solution, with vigorous release of gas. The mixture was transferred to a separatory funnel containing water (40 mL) and EtOAc (40 mL), and the phases were separated. The aqueous phase was extracted EtOAc (3×40 mL). The combined organic extracts were washed with water (40 mL) and brine (40 mL), before being dried over sodium sulphate, filtered, and concentrated to afford a crude isolate. The crude isolate was purified by flash column chromatography on silica gel using an elution system of Heptane/EtOAc as follows: 95:5 (0 min)→50:50 (20 min), 45 mL/min, 40 g column, CH$_2$Cl$_2$ load (2×3.0 mL), to afford the desired product as a clear oil.

tert-butyl (S)-2-((5-bromo-2-(methoxycarbonyl)phenoxy)methyl)-4,4-difluoropyrrolidine-1-carboxylate (INT40)

To a stirred solution of methyl 4-bromo-2-hydroxybenzoate (INT1, 924 mg, 1.0 equiv., 4.00 mmol), the Boc-protected amino alcohol (INT39, 1.04 g, 1.1 equiv., 4.40 mmol) and Ph$_3$P (1.03 g, 1.1 equiv., 4.40 mmol) in anhydrous toluene (16 mL) and the solution was cooled to 0° C. in an ice-bath, diethyl azodicarboxylate (40 wt % in toluene, 2.00 mL, 1.10 equiv., 4.40 mmol) was added dropwise at 0° C. and the reaction mixture was stirred at room temperature. After 2 hours, the mixture was concentrated, before being directly purified by flash column chromatography on silica gel using an elution system of Heptane/EtOAc as follows: 100:0 (0 min)→65:35 (30 min) (80 g column, 45 mL/min, CH$_2$Cl$_2$ load (2×4.0 mL) to afford the desired product as a clear sticky oil.

tert-butyl N-(2-(diethoxyphosphoryl)acetyl)-N-methylglycinate (INT41)

The starting material, sarcosine tert-butyl ester hydrochloride (7.27 g, 1.0 equiv., 40.0 mmol) and the starting material acid, diethylphosphonoacetic acid (8.63 g, 1.1 equiv., 44.0 mmol) were charged into a flame-dried, one-necked flask (250 mL) and placed under an argon atmosphere. Addition of anhydrous dimethylformamide (80 mL) was made at room temperature and the mixture was cooled to 0° C. in an ice bath. Subsequent addition of TBTU (15.5 g, 1.1 equiv., 44.0 mmol) was made, before adding DIPEA (20.9 mL, 3.0 equiv., 120 mmol). The mixture was stirred at room temperature. Upon completion, the reaction was quenched using water (100 mL) and 1 M aqueous hydrochloric acid solution (100 mL) and the mixture was diluted with EtOAc/Et$_2$O (3:1, 80 mL). The phases were separated, and the aqueous phase was extracted with EtOAc/Et$_2$O (3:1, 3×80 mL). The combined organic extracts were washed with water (80 mL), saturated aqueous sodium bicarbonate (80 mL) and brine (80 mL), before being dried over sodium sulphate and concentrated to afford a crude isolate. The crude isolate was purified by flash column chromatography on silica gel using an elution system of heptane/acetone as follows: 70:30→60:40→50:50→40:60→30:70 (500 mL portions, load using heptane/acetone 70:30, 100 mL fractions to afford the desired product as a clear colorless oil contaminated with a purple discoloration.

N-(2-(diethoxyphosphoryl)acetyl)-N-methylglycine (INT42)

The tert-butyl ester starting material (INT41, 8.6 g, 1.0 equiv., 26.5 mmol) was charged into a one-necked flask (100 mL) equipped with a stirrer bar, followed by the addition of dichloromethane (18.3 mL). To the aforementioned solution, was added trifluoroacetic acid (8.2 mL, 4 equiv., 106 mmol) while stirring. The mixture was analyzed by TLC to judge conversion of the starting material ester. Upon reaching full conversion of starting material, the mixture was concentrated on the rotary evaporator, followed by repeated addition and concentration of toluene (2×20 mL) to remove any excess acid from the crude product. The crude product was distributed between Et$_2$O (100 mL) and water (100 mL). The phases were separated and the aqueous phase was concentrated to afford the desired product as a clear sticky oil. The product was advanced in the synthesis without further purification.

Methyl (S)-4-bromo-2-((1-(N-(2-(diethoxyphosphoryl)acetyl)-N-methylglycyl)-4,4-difluoropyrrolidin-2-yl)methoxy)benzoate (INT43)

The starting material carbamate derivative, (INT40, 1.90 g, 1.0 equiv., 4.00 mmol) was placed a one-necked flask (100 mL) equipped with a stirrer bar and the flask was placed in an ice-bath. Addition of 4 M hydrochloric acid in dioxane (10.0 mL) was made at 0 degrees and the mixture was stirred for 0.5 hours at room temperature, at which time, TLC analysis indicated full conversion of starting material. Repeated addition of Et$_2$O (2×50 mL) and concentration afforded the amine hydrochloride as a white solid, that was used directly in the subsequent coupling step. A flame-dried flask (100 mL) equipped with a stirrer bar under an argon atmosphere was charged with the amine hydrochloride (an estimated 1.45 g, 1.0 equiv., 3.76 mmol) and the phosphonate acid derivative (INT42, 1.26 g, 1.25 equiv., 4.70 mmol). Addition of anhydrous dimethylformamide (18.8 mL) was made and the mixture was cooled to 0° C. using an ice bath followed by subsequent addition of TBTU (1.78 g, 1.25 equiv., 4.70 mmol). Finally, addition of DIPEA (1.97 mL, 3.0 equiv., 11.3 μmol) was made at 0° C. and the reaction mixture was slowly allowed to reach room temperature overnight. The mixture was monitored by TLC analysis to determine product formation. Upon completion, the reaction was quenched using water (50 mL) and 1 M aqueous hydrochloric acid solution (25 mL) and the mixture was diluted with EtOAc/ether (3:1, 60 mL). The phases were separated, and the aqueous phase was extracted with EtOAc/ether (3:1, 3×40 mL). The combined organic extracts were washed with water (40 mL), saturated aqueous sodium bicarbonate (40 mL) and brine (40 mL), before being dried over sodium sulphate and concentrated to afford a crude isolate. The crude isolate was purified by flash column chromatography on silica gel using an elution system of CH$_2$Cl$_2$/iPrOH as follows: 100:0 (0 min)→100:0 (1 min)→85:15 (30 min) (80 g column, 45 mL/min, CH$_2$Cl$_2$ load, 2×4.0 mL), to afford the desired product as an amorphous sticky solid.

(S)-4-bromo-2-((1-(N-(2-(diethoxyphosphoryl)acetyl)-N-methylglycyl)-4,4-difluoropyrrolidin-2-yl)methoxy)benzoic acid (INT44)

The starting material methyl ester derivative (INT43, 2.12 g, 1.0 equiv., 3.54 mmol), was dissolved in tetrahydrofuran (26.6 mL), followed by the addition of water (4.4 mL) and MeOH (4.4 mL). Subsequent addition of lithium hydroxide monohydrate (223 mg, 1.5 equiv., 5.31 mmol) was made and the mixture was stirred at room temperature while being followed by TLC analysis. Upon reaching full conversion of starting material as indicated by TLC analysis, the mixture was poured into a separatory funnel, containing water (40 mL), brine (40 mL) and EtOAc (60 mL) before the mixture was adjusted to pH <4, using 1.0 M aqueous hydrochloric acid solution. The phases were separated, and the aqueous phase was extracted with EtOAc (3×40 mL). The combined organic extracts were washed with brine (40 mL), before being dried over sodium sulphate, filtered, and concentrated. The crude isolate was directly advanced in the synthesis without further purification.

Diethyl (2-((2-((S)-2-((5-bromo-2-(((R)-1-hydroxy-3-((triisopropylsilyl)-oxy)propan-2-yl)carbamoyl)phenoxy)methyl)-4,4-difluoropyrrolidin-1-yl)-2-oxoethyl)(methyl)amino)-2-oxoethyl)phosphonate (INT45)

To a stirring mixture of the free acid (INT44, 1.99 g, 1.00 equiv., 3.40 mmol) in anhydrous dichloromethane (9.0 mL) in a one-necked flask (100 mL) equipped with a stirrer bar, under an argon atmosphere, was added DEPBT (2.08 g, 2.0 equiv., 6.80 mmol), and triethylamine (1.42 mL, 3.0 equiv., 10.2 mmol), followed by addition of the serinolamine ((R)-INT59, 1.01 g, 1.2 equiv., 4.08 mmol) in anhydrous dichloromethane (8.8 mL). After being stirred overnight at room temperature, the reaction was quenched by addition of water (50 mL) and 1 M aqueous hydrochloric acid solution (25 mL), the mixture was diluted with EtOAc (100 mL) and the layers were separated. The aqueous phase was extracted with EtOAc (3×40 mL). The combined organic phases were washed with water (50 mL), 1 M aqueous potassium carbonate (2×50 mL), and brine (50 mL), dried over sodium sulphate, filtered, and concentrated to afford a crude isolate. The crude material was purified by flash column chromatography on silica gel using an elution system of CH$_2$Cl$_2$/iPrOH as follows: 100:0 (0 min)→100:0 (2 min)→80:20 (25 min), 80 g column, 60 mL/min, dichloromethane load (2×6.0 mL), to afford the desired product as an amorphous sticky solid with a yellow discoloration.

Diethyl (2-((2-((S)-2-((5-(dodec-1-yn-1-yl)-2-(((R)-1-hydroxy-3-((triisopropylsilyl)oxy)propan-2-yl)carbamoyl)phenoxy)methyl)-4,4-difluoropyrrolidin-1-yl)-2-oxoethyl)(methyl)amino)-2-oxoethyl)-phosphonate (INT46)

A flame-dried, one-necked flask (10 mL) was charged with the bromoarene derivative (INT45, 407 mg, 1.0 equiv., 500 µmol), CuI (19 mg, 0.2 equiv., 100 µmol), PdCl$_2$(PPh$_3$)$_2$ (28 mg, 0.1 equiv., 50 µmol), and the atmosphere of the reaction vessel was evacuated and replaced with argon. Anhydrous dimethylformamide (2.5 mL), 1-dodecyne (214 µL, 2.0 equiv., 1.00 mmol) and Et$_3$N (209 µL, 3.0 equiv., 1.50 mmol) was added. The mixture was heated to 75° C., and after 4 hours of reaction time, the mixture was distributed between water (20 mL), 1 M aqueous hydrochloric acid solution (10 mL) and EtOAc/Et$_2$O 2:1 (30 mL). The aqueous phase was extracted with EtOAc/Et$_2$O 2:1 (2×30 mL), before being washed with water (30 mL) and brine (30 mL). The combined organic extracts were dried over sodium sulphate, filtered, and concentrated to afford a crude isolate. The crude product was purified by flash column chromatography on silica gel using an elution system of Heptane/Acetone 85:15 (0 min)→85:15 (1 min)→30:70 (14.5 min), (12 g column, 45 mL/min, CH$_2$Cl$_2$ load (2×3.0 mL)) to afford the desired product as a clear amorphous solid.

Diethyl (2-((2-((S)-2-((5-dodecyl-2-(((R)-1-hydroxy-3-((triisopropylsilyl)oxy)propan-2-yl)carbamoyl)phenoxy)methyl)-4,4-difluoropyrrolidin-1-yl)-2-oxoethyl)(methyl)amino)-2-oxoethyl)-phosphonate (INT47)

A one-necked flask (50 mL) equipped with a stirrer bar under an argon atmosphere, containing the starting material alkyne derivative (INT46, 315 mg, 1.0 equiv., 350 µmol) was charged with Pd/C (10% Pd, 19 mg, 0.05 equiv., 18 µmol). Subsequently, MeOH (7.0 mL) was added. The atmosphere in the reaction vessel was exchanged to hydrogen, and the reaction mixture was stirred overnight under a hydrogen atmosphere maintained by a balloon. After being stirred overnight, the reaction mixture was filtered celite, and the filter cake was washed successively with EtOAc (2×30 mL) to afford the desired product as a pale-yellow sticky oil.

(19aS,E)-16-dodecyl-2,2-difluoro-7-methyl-11-(((triisopropylsilyl)-oxy)methyl)-2,3,6,7,11,12,19,19a-octahydro-1H,5H-benzo[n]pyrrolo[2,1-c][1]oxa[4,7,12]triazacyclopentadecine-5,8,13-trione (INT48)

To a stirring solution of the phosphonate alcohol (INT470, 330 mg, 1.0 equiv. 365 µmol) in dichloromethane (7.3 mL) in a one-necked flask (25 mL) equipped with a stirrer bar was added Dess-Martin periodinane (310 mg, 2.0 equiv., 730 µmol). After stirring the mixture for 1.0 hour at ambient temperature, the reaction was poured into a separatory funnel containing saturated aqueous NaHCO$_3$ (10 mL) and saturated aqueous Na$_2$S$_2$O$_3$ (10 mL), using EtOAc (25 mL) to wash the reaction vessel and dilute the organic phase in the separatory funnel. The mixture was shaken vigorously until the organic phase became clear. The aqueous phase was extracted with EtOAc (3×20 mL). The combined organic extracts were washed with brine (20 mL), dried over sodium sulphate, filtered, and concentrated. The crude product was directly advanced in the synthetic sequence.

The aldehyde precursor directly applied from the oxidation reaction (approximately 329 mg, 1.0 equiv., 365 µmol) was dissolved in anhydrous tetrahydrofuran (146 mL) in a one-necked flask (250 mL) equipped with a stirrer bar under an argon atmosphere, and anhydrous Et$_3$N (254 µL, 5.0 equiv., 1.82 mmol) was added followed immediately by TMEDA (111 µL, 2.0 equiv., 730 µmol) and Zn(OTf)$_2$ (542 mg, 4.0 equiv., 1.46 mmol). The mixture was left stirring at room temperature overnight. Upon being deemed complete based on TLC analysis, the reaction was concentrated down to a total volume of approximately 20 mL, before being transferred to a separatory funnel containing water (40 mL) and brine (40 mL) and 1.0 M aqueous HCl solution (20 mL), using EtOAc (40 mL) to allow quantitative transfer to the separation funnel. The layers were separated, the aqueous phase was extracted with EtOAc (3×40 mL). The combined organic phases were washed with water (40 mL), 1 M aqueous potassium carbonate (40 mL) and brine (40 mL) before being dried over sodium sulphate, filtered, and concentrated to afford a crude isolate. The crude material was purified by flash column chromatography using an elution system of Heptane/Acetone as follows: 90:10 (0 min)→90:10 (1 min)→30:70 (22 min) (12 g column, dichloromethane load (2×4.0 mL), 30 mL/min). The desired product was afforded as an amorphous colorless solid.

(19aS,E)-16-dodecyl-2,2-difluoro-11-(hydroxymethyl)-7-methyl-2,3,6,7,11,12,19,19a-octahydro-1H, 5H-benzo[n]pyrrolo[2,1-c][1]oxa[4,7,12]triazacyclopentadecine-5,8,13-trione (INT49)

The starting material silyl-ether (INT48, 36 mg, 1.0 equiv., 50 µmol), was charged into a one-necked flask (10 mL) equipped with a stirrer bar under an argon atmosphere. The starting material was dissolved in anhydrous tetrahydrofuran (1.0 mL) and the solution was cooled to 0° C. in an ice-bath. Subsequent addition of tetrabutylammonium fluoride (1 M solution in tetrahydrofuran, 75 µL, 1.5 equiv., 75 µmol) was made at 0° C. and subsequent, the ice-bath was removed, and the mixture was stirred at room temperature. After 1 hour of reaction time, addition of Et$_2$O (5.0 mL) was made and the solution was concentrated using a stream of nitrogen to afford a crude product. The crude product was purified by flash column chromatography on silica gel using an elution system of EtOAc/MeOH as follows: 100:0 (0 min)→100:0 (1 min)→88:12 (16 min), 12 g column, 30 mL/min, EtOAc load (2×1.0 mL), to afford the desired product as a colorless solid.

(S,E)-16-dodecyl-2,2-difluoro-7-methyl-11-methylene-2,3,6,7,11,12,19,19a-octahydro-1H,5H-benzo[n]pyrrolo[2,1-c][1]oxa-[4,7,12]triazacyclopentadecine-5,8,13-trione (PH905)

The starting material alcohol (INT49, 24 mg, 1.0 equiv., 42 µmol) was dissolved in anhydrous MeCN/tetrahydrofuran (1.0:1.0 mL) under an argon atmosphere, to become a colorless, clear solution. Addition of DSC (23 mg, 2.0 equiv., 83 µmol) and DIPEA (22 µL, 3.0 equiv., 125 µmol) was made to the reaction mixture at room temperature. The reaction was stirred for 17 hours at 45° C. The reaction mixture was cooled to room temperature before being concentrated using a flow of nitrogen. The crude product was analyzed by $^1$H-NMR spectroscopy to evaluate product formation. The crude product was purified by preparative HPLC using an elution system of acetonitrile/water, followed by concentration to afford the desired product as a colorless solid. The isolated compound exists as two conformational isomers. Spectroscopic data is reported with relative integrals for each signal. $^1$H NMR (400 MHz, DMSO-d$_6$) δ=9.68 (s, 0.38H), 9.28 (s, 0.55H), 7.78 (d, J=7.9 Hz, 0.54H), 7.35-7.31 (m, 0.50H), 7.11 (s, 0.56H), 7.01 (s, 0.37H), 6.98-6.83 (m, 2.04H), 6.22-6.02 (m, 1.53H), 5.45 (s, 0.37H), 5.39 (s, 0.37H), 5.32 (s, 0.59H), 4.98 (d, J=12.4 Hz, 0.52H), 4.65 (d, J=17.2 0., 0.88H), 4.56-4.44 (m, 1.29H), 4.43-4.29 (m, 1.15H), 4.28-4.12 (m, 1.72H), 4.11-3.92 (m, 1.71H), 3.68 (q, J=14.2 Hz, 0.39H), 2.99 (s, 1.75H), 2.91 (s, 1.21H), 2.61 (q, J=7.7 Hz, 2.06H), 1.65-1.51 (m, 2.02H), 1.35-1.16 (m, 18H), 0.85 (t, J=6.6, 3H).

Example 9—Synthesis of PH921

Figure 8:
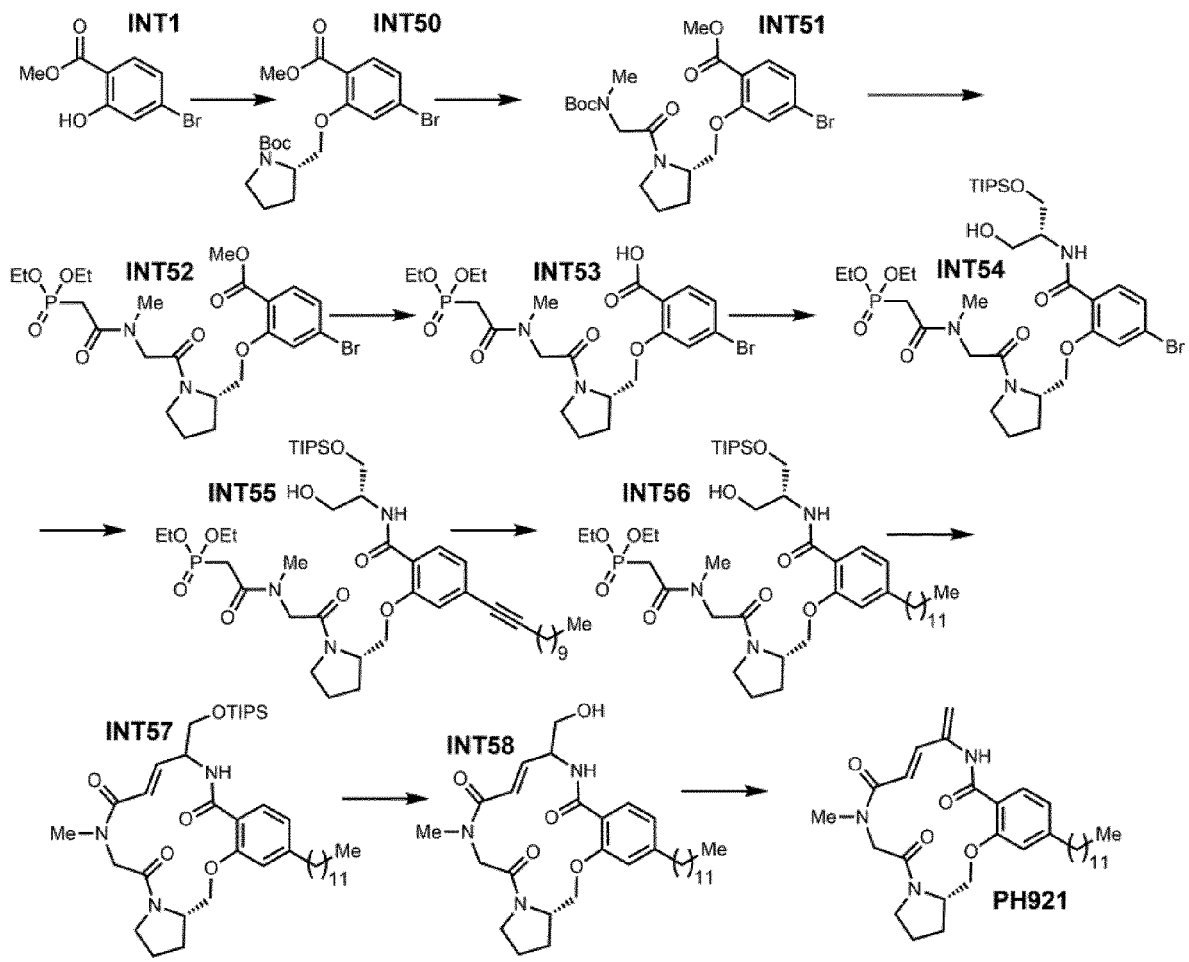
FIG. 8 shows the synthetic route to PH921.

In the following is described the synthesis of PH921 and its specific intermediates (INT) (see FIG. 8).

tert-butyl (S)-2-((5-bromo-2-(methoxycarbonyl) phenoxy)methyl)-pyrrolidine-1-carboxylate (INT50)

To a stirred solution of methyl 4-bromo-2-hydroxybenzoate (INT1, 924 mg, 1.0 equiv., 4.00 mmol), the Boc-protected amino alcohol, N-Boc-L-prolinol (886 mg, 1.1 equiv., 4.40 mmol) and $Ph_3P$ (1.03 g, 1.1 equiv., 4.40 mmol) in anhydrous toluene (16 mL) and the solution was cooled to 0° C. in an ice-bath, diethyl azodicarboxylate (40 wt % in toluene, 2.00 mL, 1.10 equiv., 4.40 mmol) was added dropwise at 0° C. and the reaction mixture was stirred at room temperature. After 2 hours, the mixture was concentrated, before being directly purified by flash column chromatography on silica gel using an elution system of Heptane/EtOAc as follows: 100:0 (0 min)→100:0 (2 min)→50:50 (30 min) (80 g column, 45 mL/min., $CH_2Cl_2$ load (2×3.0 mL) to afford the desired product as a clear sticky oil.

(S)-2-((5-bromo-2-(methoxycarbonyl)phenoxy) methyl)pyrrolidin-1-ium chloride (INT51)

The starting material carbamate derivative, (INT50, 1.63 g, 1.0 equiv., 3.94 mmol) was placed in a one-necked flask (100 mL) equipped with a stirrer bar and the flask was placed in an ice-bath. Addition of 4 M hydrochloric acid in 1,4-dioxane (9.9 mL) was made at 0° C. and the mixture was stirred for 0.5 hours at room temperature, at which time, TLC analysis indicated full conversion of starting material. Repeated addition of $Et_2O$ (2×50 mL) and concentration afforded the amine hydrochloride as a white solid, that was used directly in the subsequent coupling step. A flame-dried flask (50 mL) equipped with a stirrer bar under an argon atmosphere was charged with the amine-derived hydrochloride (an estimated 1.34 g, 1.00 equiv., 3.83 mmol), Boc-Sar-OH (1.34 g, 1.25 equiv., 4.79 mmol) followed by the addition of anhydrous dimethylformamide (19.2 mL). The mixture was cooled to 0° C. using an ice bath followed by addition of TBTU (1.54 g, 1.25 equiv., 4.79 mmol), followed by the addition of DIPEA (2.0 mL, 3.0 equiv., 11.5 mmol). The mixture was stirred at room temperature. Upon completion, the reaction was quenched using water (50 mL) and 1 M aqueous hydrochloric acid solution (25 mL) and the mixture was diluted with EtOAc/ether (3:1, 60 mL). The phases were separated, and the aqueous phase was extracted with EtOAc/ether (3:1, 3×40 mL). The combined organic extracts were washed with water (40 mL), saturated aqueous sodium bicarbonate (40 mL) and brine (40 mL), before being dried over sodium sulphate and concentrated to afford a crude isolate. The crude material was purified by flash column chromatography on silica gel using an elution system of Heptane/EtOAc as follows: 100:0 (0 min)→100:0 (1 min)→60:40 (20 min), 25 g column, 45 mL/min., $CH_2Cl_2$ load (2×3.0 mL) to afford the desired product as a colorless oil.

(S)-2-(2-((5-bromo-2-(methoxycarbonyl)phenoxy) methyl)pyrrolidin-1-yl)-N-methyl-2-oxoethan-1-aminium chloride (INT52)

The starting material carbamate derivative, (INT51, 1.83 g, 1.0 equiv., 3.76 mmol) was placed a flame-dried one-necked flask (100 mL) equipped with a stirrer bar and the flask was placed in an ice-bath. Addition of 4 M hydrochloric acid in 1,4-dioxane (9.4 mL) was made at 0° C. and the mixture was stirred for 0.5 hours at room temperature, at which time, TLC analysis indicated full conversion of starting material. Repeated addition of $Et_2O$ (2×50 mL) and concentration afforded the amine hydrochloride as a an amorphous solid, that was used directly in the subsequent coupling step. A flame-dried flask (100 mL) equipped with a stirrer bar under an argon atmosphere was charged with the amine-derived hydrochloride (an estimated 1.59 g, 1.00 equiv., 3.76 mmol), diethylphosphonoacetic acid (922 mg, 1.25 equiv., 4.70 mmol) followed by the addition of anhydrous dimethylformamide (18.8 mL). The mixture was cooled to 0° C. using an ice bath followed by addition of TBTU (1.51 g, 1.25 equiv., 4.70 mmol), followed by the addition of DIPEA (1.96 mL, 3.0 equiv., 11.3 mmol). The mixture was stirred at room temperature. Upon completion, the reaction was quenched using water (50 mL) and 1 M aqueous hydrochloric acid solution (25 mL) and the mixture was diluted with EtOAc/ether (3:1, 60 mL). The phases were separated, and the aqueous phase was extracted with EtOAc/ether (3:1, 3×40 mL). The combined organic extracts were washed with water (40 mL), saturated aqueous sodium bicarbonate (40 mL) and brine (40 mL), before being dried over sodium sulphate and concentrated to afford a crude isolate. The crude material was purified by flash column chromatography on silica gel using an elution system of dichloromethane/iPrOH as follows: 100:0 (0 min)→100:0 (0 min)→86:14 (30 min), 40 g column, 45 mL/min, dichloromethane load (2×3.5 mL) to afford the desired product as a clear oil.

(S)-4-bromo-2-((1-(N-(2-(diethoxyphosphoryl) acetyl)-N-methylglycyl)-pyrrolidin-2-yl)methoxy) benzoic acid (INT53)

The starting material methyl ester derivative (INT52, 1.91 g, 1.0 equiv., 3.39 mmol), was dissolved in tetrahydrofuran (25.4 mL), followed by the addition of water (4.2 mL) and MeOH (4.2 mL). Subsequent addition of lithium hydroxide monohydrate (213 mg, 2.0 equiv., 5.09 mmol) was made and the mixture was stirred at room temperature while being followed by TLC analysis. Upon reaching full conversion of starting material as indicated by TLC analysis, the mixture was poured into a separatory funnel, containing water (40 mL), brine (40 mL) and EtOAc (60 mL) before the mixture was adjusted to pH <4, using 1.0 M aqueous hydrochloric acid solution. The phases were separated, and the aqueous phase was extracted with EtOAc (3×40 mL). The combined organic extracts were washed with brine (40 mL), before being dried over sodium sulphate, filtered, and concentrated. The crude isolate was analyzed by $^1$H-NMR spectroscopy, and the crude product was directly advanced in the synthesis without further purification.

Diethyl (2-((2-((S)-2-((5-bromo-2-(((R)-1-hydroxy-3-((triisopropylsilyl)-oxy)propan-2-yl)carbamoyl) phenoxy)methyl)pyrrolidin-1-yl)-2-oxoethyl) (methyl)amino)-2-oxoethyl)phosphonate (INT54)

To a stirring mixture of the free acid (INT53, 1.83 g, 1.00 equiv., 3.30 mmol) in anhydrous dichloromethane (8.4 mL) in a one-necked flask (100 mL) equipped with a stirrer bar, under an argon atmosphere, was added DEPBT (2.03 g, 2.0 equiv., 6.66 mmol), and triethylamine (1.39 mL, 3.0 equiv., 10.0 mmol), followed by addition of the serinolamine ((R)-

INT59, 989 mg, 1.2 equiv., 4.00 mmol) in anhydrous dichloromethane (8.3 mL). After being stirred for 6 hours at room temperature, the reaction was quenched by addition of water (50 mL) and 1 M aqueous hydrochloric acid solution (25 mL), the mixture was diluted with EtOAc (60 mL) and the layers were separated. The aqueous phase was extracted with EtOAc (3×40 mL). The combined organic phases were washed with water (50 mL), 1 M aqueous potassium carbonate (2×50 mL), and brine (50 mL), dried over sodium sulphate, filtered, and concentrated to afford a crude isolate. The crude material was purified by flash column chromatography on silica gel using an elution system of $CH_2Cl_2$/iPrOH as follows: 100:0 (0 min)→100:0 (2 min)→84:16 (25 min), 80 g column, 60 mL/min, dichloromethane load (2×6.0 mL), to afford the desired product as an amorphous sticky solid with a yellow discoloration.

Diethyl (2-((2-((S)-2-((5-(dodec-1-yn-1-yl)-2-(((R)-1-hydroxy-3-((triisopropylsilyl)oxy)propan-2-yl)carbamoyl)phenoxy)methyl)-pyrrolidin-1-yl)-2-oxoethyl)(methyl)amino)-2-oxoethyl)phosphonate (INT55)

A flame-dried, one-necked flask (10 mL) was charged with the bromoarene derivative (INT55, 312 mg, 1.0 equiv., 400 μmol), CuI (15 mg, 0.2 equiv., 80 μmol), $PdCl_2(PPh_3)_2$ (28 mg, 0.1 equiv., 40 μmol), and the atmosphere of the reaction vessel was evacuated and replaced with argon. Anhydrous dimethylformamide (2.0 mL), 1-dodecyne (167 μL, 2.0 equiv., 800 μmol) and $Et_3N$ (167 μL, 3.0 equiv., 1200 μmol) was added. The mixture was heated to 75° C., and after 4 hours of reaction time, the mixture was distributed between water (20 mL), 1 M aqueous hydrochloric acid solution (10 mL) and EtOAc/$Et_2O$ 2:1 (30 mL). The aqueous phase was extracted with EtOAc/$Et_2O$ 2:1 (2×30 mL), before being washed with water (30 mL) and brine (30 mL). The combined organic extracts were dried over sodium sulphate, filtered, and concentrated to afford a crude isolate. The crude product was purified by flash column chromatography on silica gel using an elution system of Heptane/Acetone 80:20 (0 min.)→80:20 (1 min.)→25:75 (17.5 min.), (25 g column, 45 mL/min., $CH_2Cl_2$ load (2×3.0 mL)) to afford the desired product as a clear amorphous solid.

Diethyl (2-((2-((S)-2-((5-dodecyl-2-(((R)-1-hydroxy-3-((triisopropylsilyl)oxy)propan-2-yl)carbamoyl)phenoxy)methyl)-pyrrolidin-1-yl)-2-oxoethyl)(methyl)amino)-2-oxoethyl)phosphonate (INT56)

A one-necked flask (50 mL) equipped with a stirrer bar under an argon atmosphere, containing the starting material alkyne derivative (INT55, 237 mg, 1.0 equiv., 274 μmol) was charged with Pd/C (10% Pd, 29 mg, 0.10 equiv., 27 μmol). Subsequently, MeOH (5.5 mL) was added. The atmosphere in the reaction vessel was exchanged to hydrogen, and the reaction mixture was stirred overnight under a hydrogen atmosphere maintained by a balloon. After being stirred overnight, the reaction mixture was filtered on celite, and the filter cake was washed successively with EtOAc (2×30 mL) to afford the desired product as a pale-yellow sticky oil.

(19aS,E)-16-dodecyl-7-methyl-11-(((triisopropylsilyl)oxy)methyl)-2,3,6,7,11,12,19,19a-octahydro-1H, 5H-benzo[n]pyrrolo[2,1-c][1]oxa[4,7,12]triazacyclopentadecine-5,8,13-trione (INT57)

To a stirring solution of the phosphonate alcohol (INT56, 245 mg, 1.0 equiv. 282 μmol) in dichloromethane (5.6 mL) in a one-necked flask (50 mL) equipped with a stirrer bar was added Dess-Martin periodinane (239 mg, 2.0 equiv., 564 μmol). After stirring the mixture for 1.0 hour at ambient temperature, the reaction was poured into a separatory funnel containing saturated aqueous $NaHCO_3$ (10 mL) and saturated aqueous $Na_2S_2O_3$ (10 mL), using EtOAc (25 mL) to wash the reaction vessel and dilute the organic phase in the separatory funnel. The mixture was shaken vigorously until the organic phase became clear. The aqueous phase was extracted with EtOAc (3×20 mL). The combined organic extracts were washed with brine (20 mL), dried over sodium sulphate, filtered, and concentrated. The crude product was directly advanced in the synthetic sequence.

The aldehyde precursor directly applied from the oxidation reaction (approximately 244 mg, 1.0 equiv., 282 μmol) was dissolved in anhydrous tetrahydrofuran (113 mL) in a one-necked flask (250 mL) equipped with a stirrer bar under an argon atmosphere, and anhydrous $Et_3N$ (196 μL, 5.0 equiv., 1.41 mmol) was added followed immediately by TMEDA (85 μL, 2.0 equiv., 564 μmol) and $Zn(OTf)_2$ (418 mg, 4.0 equiv., 1.13 mmol). The mixture was left stirring at room temperature overnight. Upon being deemed complete based on TLC analysis, the reaction was concentrated down to a total volume of approximately 20 mL, before being transferred to a separatory funnel containing water (40 mL) and brine (40 mL) and 1.0 M aqueous HCl solution (20 mL), using EtOAc (40 mL) to allow quantitative transfer to the separation funnel. The layers were separated, the aqueous phase was extracted with EtOAc (3×40 mL). The combined organic phases were washed with water (40 mL), 1 M aqueous potassium carbonate (40 mL) and brine (40 mL) before being dried over sodium sulphate, filtered and concentrated to afford a crude isolate. The crude material was purified by flash column chromatography using an elution system of Heptane/acetone as follows: 90:10 (0 min.)→90:10 (1 min)→40:60 (22 min) (12 g column, $CH_2Cl_2$ load (2×4.0 mL), 30 mL/min.). The desired product was afforded as an amorphous colorless solid.

(19aS,E)-16-dodecyl-11-(hydroxymethyl)-7-methyl-2,3,6,7,11,12,19,19a-octahydro-1H,5H-benzo[n]pyrrolo[2,1-c][1]oxa[4,7,12]triazacyclopentadecine-5,8,13-trione (INT58)

The starting material silyl-ether (INT57, 115 mg, 1.0 equiv., 161 μmol), was charged into a one-necked flask (25 mL) equipped with a stirrer bar under an argon atmosphere. The starting material was dissolved in anhydrous tetrahydrofuran (3.2 mL) and the solution was cooled to 0° C. in an ice-bath. Subsequent addition of TBAF (1 M solution in tetrahydrofuran, 201 μL, 1.25 equiv., 201 μmol) was made at 0° C. and subsequently, the ice-bath was removed, and the mixture was stirred at room temperature. After 1.5 hours of reaction time, addition of $Et_2O$ (5.0 mL) was made and the solution was concentrated using a stream of nitrogen to afford a crude product. The crude product was purified by flash column chromatography on silica gel using an elution system of EtOAc/MeOH as follows: 100:0 (0 min.)→100:0 (1 min.)→85:15 (20 min.), 12 g column, 30 mL/min., EtOAc load (2×2.0 mL), to afford the desired product as a colorless solid.

(S,E)-16-dodecyl-7-methyl-11-methylene-2,3,6,7,11,12,19,19a-octahydro-1H,5H-benzo[n]pyrrolo[2,1-c][1]oxa[4,7,12]triazacyclo-pentadecine-5,8,13-trione (PH921)

The starting material alcohol (INT58, 16 mg, 1.0 equiv., 30 μmol) was dissolved in anhydrous MeCN/tetrahydrofuran (1.0:1.0 mL) under an argon atmosphere. Addition of DSC (16 mg, 2.0 equiv., 60 μmol) and DIPEA (16 μL, 3.0 equiv., 90 μmol) was made to the reaction mixture at room temperature. The reaction was stirred for 17 hours at 45° C. The reaction mixture was cooled to room temperature before being concentrated using a flow of nitrogen. The crude product was purified by preparative HPLC using an elution system of acetonitrile/water to afford the desired product as a colorless solid. The isolated compound exists as two conformational isomers. Spectroscopic data is reported with relative integrals for each signal. $^1$H NMR (400 MHz, DMSO-$d_6$) δ=9.66 (s, 0.24H), 9.31 (s, 0.58H), 7.85 (d, J=7.9 Hz, 0.56H), 7.36 (d, J=7.6 Hz, 0.24H), 7.15 (s, 0.57H), 7.03 (s, 0.26H), 6.99-6.82 (m, 1.76H), 6.27 (d, J=15.2 Hz, 0.26H), 6.15 (s, 0.56H), 6.10 (d, J=15.5 Hz, 0.63H), 5.48 (s, 0.25H), 5.42 (s, 0.25H), 5.27 (s, 0.62H), 4.96 (d, J=12.5 Hz, 0.56H), 4.63-4.53 (m, 0.84H), 4.48 (d, J=17.7 Hz, 0.63H), 4.38-4.30 (m, 0.26H), 4.28-4.17 (m, 0.92H), 4.17-4.11 (m, 0.27H), 4.08-3.99 (m, 0.92H), 3.95 (t, J=9.7 Hz, 0.25H), 3.70-3.60 (m, 0.29H), 3.54-3.42 (m, 1.65H), 3.01 (s, 1.88H), 2.90 (s, 0.76H), 2.69-2.56 (m, 1.81H), 2.21-2.06 (m, 0.69H), 1.94-1.82 (m, 1.40H), 1.79-1.68 (m, 1.29H), 1.66-1.51 (m, 1.99H), 1.33-1.20 (m, 18.2H), 0.85 (t, J=6.6 Hz, 3.0H).

Example 10—Provision of Cells

PANC-1 and HaCat cells (PANC-1: RRID:CVCL 0480, taken from a 56-year-old male, HaCat: RRID:CVCL 0038) were cultured in DMEM (Gibco, Cat #: 21969-035) supplemented with FBS (10%, Gibco, Cat #: A31698-02), Penicillin/Streptomycin (1%, Sigma-Aldrich, Cat #: P0781), and Ala-Gln (200 μM, Sigma-Aldrich, Cat #: G8541). BxPC3 cells (RRID:CVCL 0186, taken from a 61-year-old female) were cultured in RPMI 1640 (Gibco, Cat #: 61870-010) supplemented with FBS (10%) and Penicillin/Streptomycin (1%). U2OS (RRID:CVCL 0042) and HCT116 cells (RRID:CVCL 0291, ATCC CCL-247) were cultured in McCoy's 5A (Sigma cat. no. M9309) supplemented with FBS (10%) and Penicillin/Streptomycin (1%). Cells were grown under normoxic conditions in T75 flasks (Biolite, Thermo Scientific, Cat #: 130190) in a humidified atmosphere with 5% $CO_2$ at 37° C. For hypoxic conditions cells were placed in a modular incubator chamber (MIC-101, Billups-Rothenberg) equipped with a 10-cm dish with milliQ water and flushed with $CO_2/N_2$ (5%/95%, BioNERT, AGA Cat #: 100466065) for 8 minutes at 20-25 L/minute. Cells were passaged approximately every third day by trypsination (Sigma-Aldrich, Cat #: T4049) followed by transfer of ⅕$^{th}$ of the cells to a new flask. All cell cultures were handled aseptically in a laminar air flow bench and grown in sterile-filtered (Jetbiofil, Cat #: FPE204500) medium according to ATCC's recommendations. All human cell lines were correctly identified by short tandem repeat analysis and tested free of mycoplasma contamination by MycoAlert (Lonza, Cat #: LT07-218).

Example 11—Chemical Stability Measurements

The stability of compounds under neutral or basic conditions were tested by dissolving compounds to 20 μM in PBS (pH 7.4) or sodium tetraborate buffer (pH 10) both mixed with 30% MeOH. The mixtures were shaken vigorously and injected immediately in the HPLC. The reactions were allowed to run at 23° C. for 9 hours and injections were performed once per hour. The concentrations of unreacted compounds were determined by UPLC-UV (Agilent 1260 infinity II) at 262 nm by injecting 5 μL on a PFP column (Poroshell 120 PFP, 3.0×100 mm, 2.7 micron). The compounds were eluted by a 1 mL/minute-gradient of acetonitrile in $H_2O$ from 5% to 95% over 8 minutes, then 95% for 1 minute and then 5% acetonitrile in $H_2O$ in 30 seconds. The results can be seen in FIGS. 11A and 11B.

Figure 11:
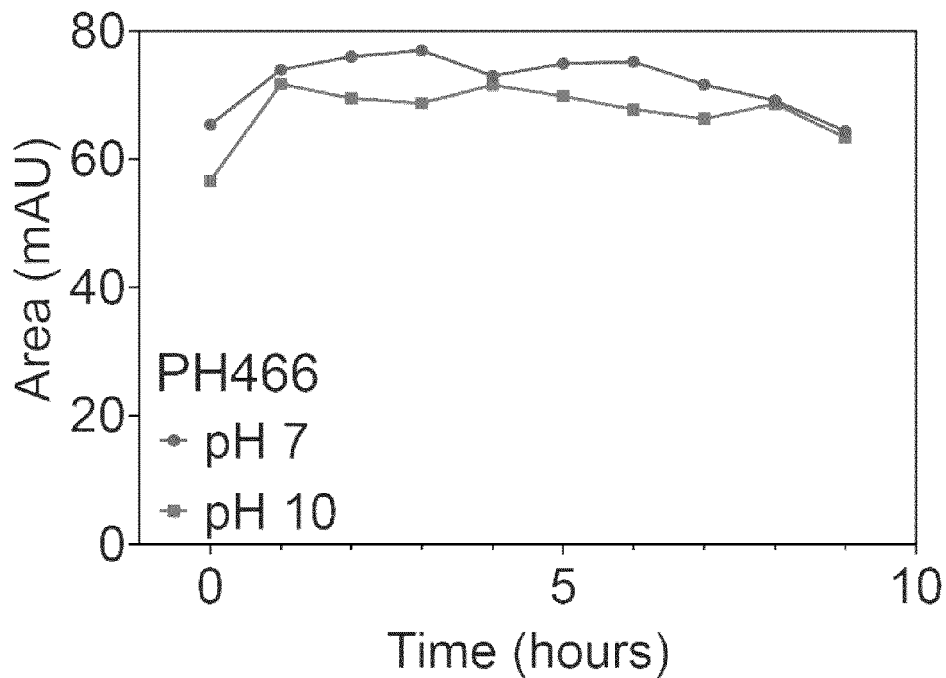
FIG. 11 shows chemical stability measurements for A) PH466, and B) rakicidin D when subjected to physiological pH (7) and elevated pH (10) for a period of up to 9 hours.
Figure 11:
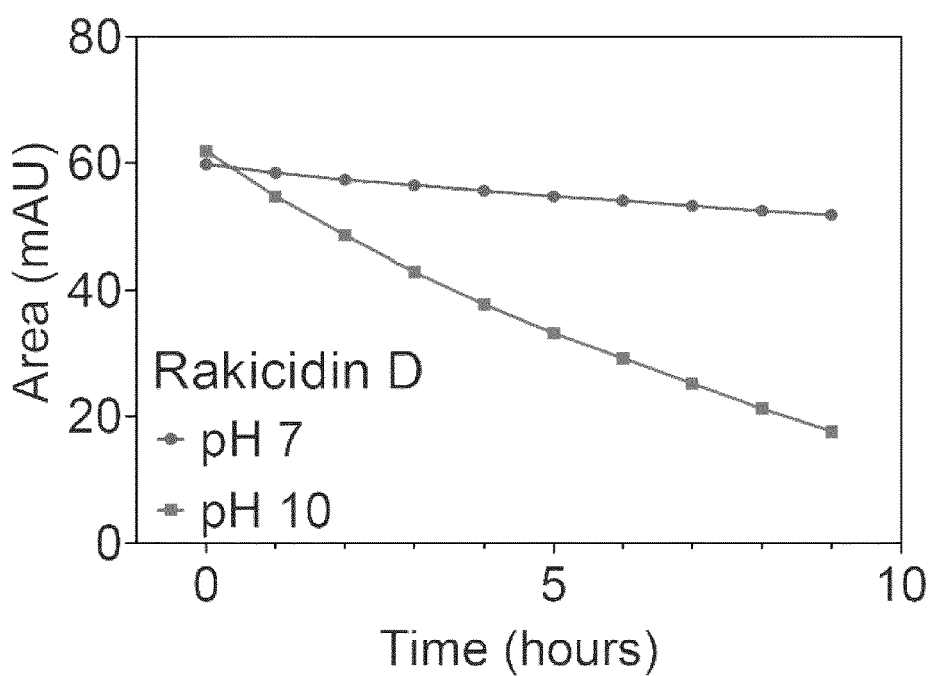
Figure 12:
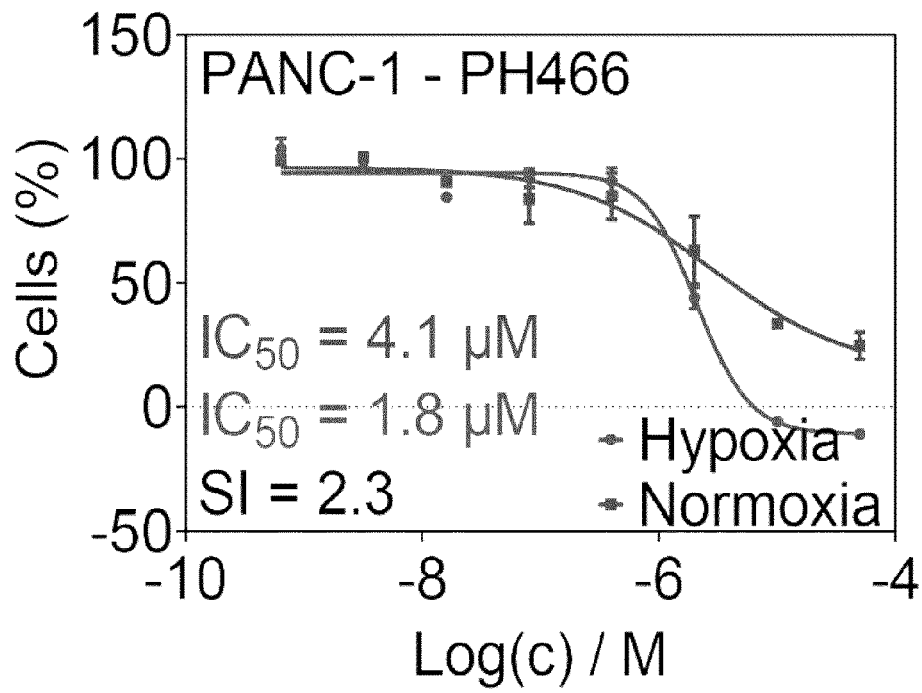
FIG. 12 shows dose-response curves obtained under hypoxic and normoxic conditions when subjecting PANC-1 cells to A) PH466, and B) evofosfamide (TH302).
Figure 12:
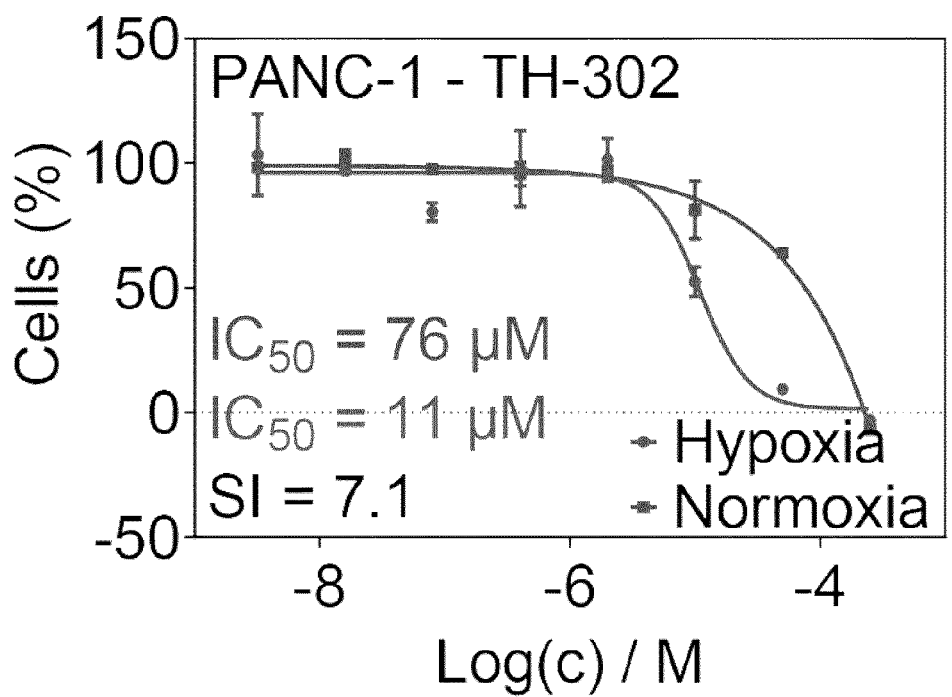
Figure 13:
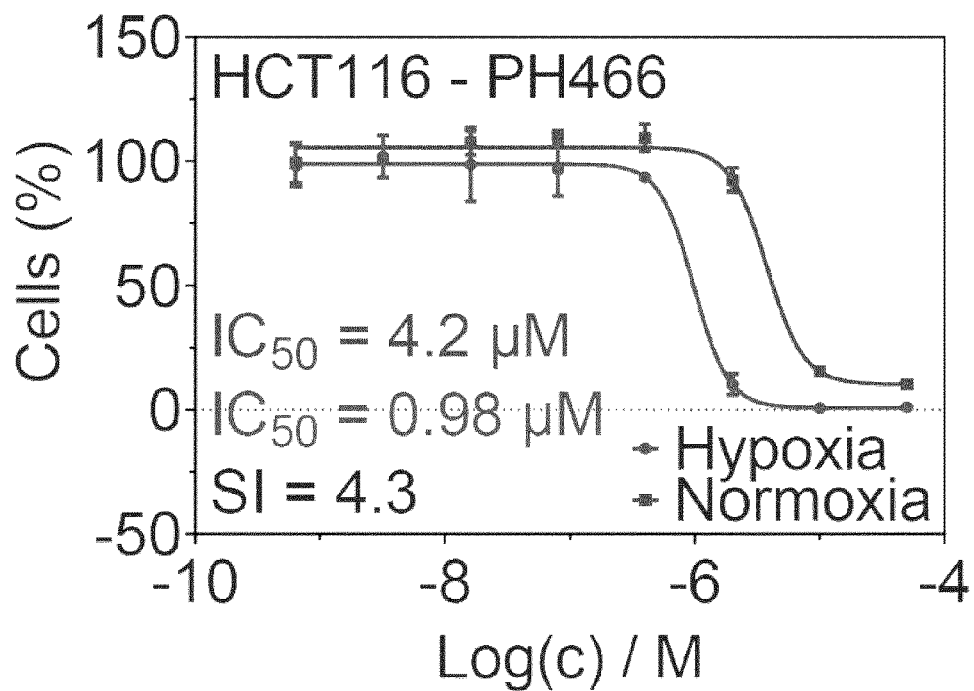
FIG. 13 shows dose-response curves obtained under hypoxic and normoxic conditions when subjecting HCT116 cells to A) PH466, and B) tirapazamine (TPZ).
Figure 13:
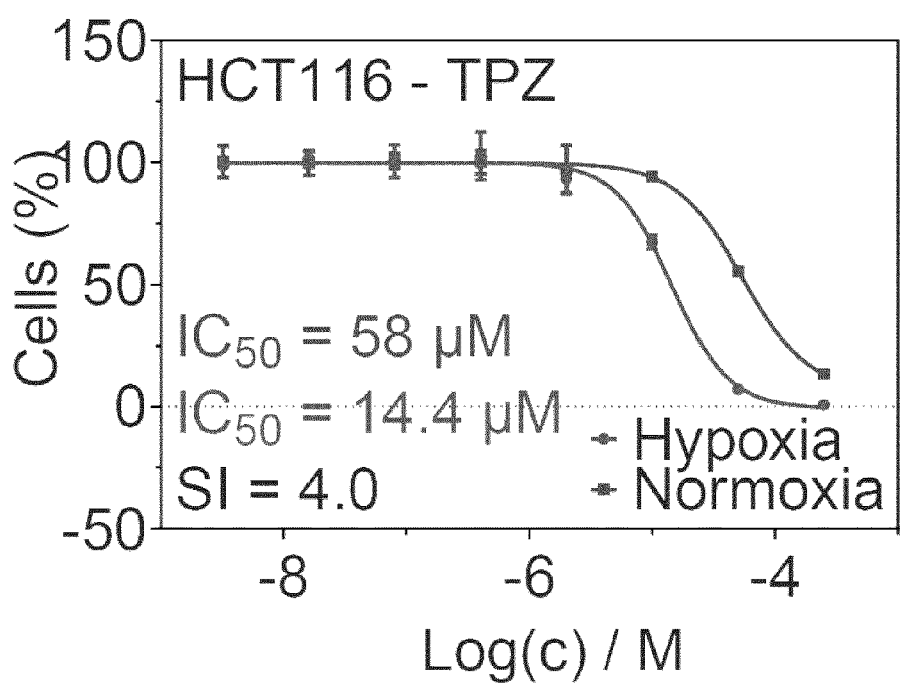
Figure 14:
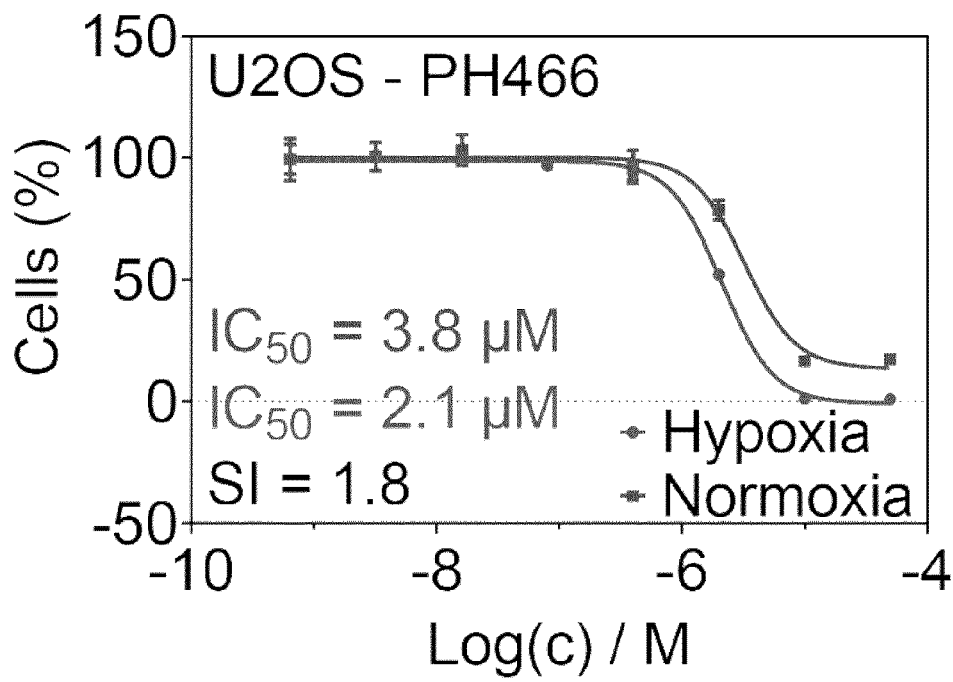
FIG. 14 shows dose-response curves obtained under hypoxic and normoxic conditions when subjecting U2OS cells to A) PH466, and B) TPZ.
Figure 14:
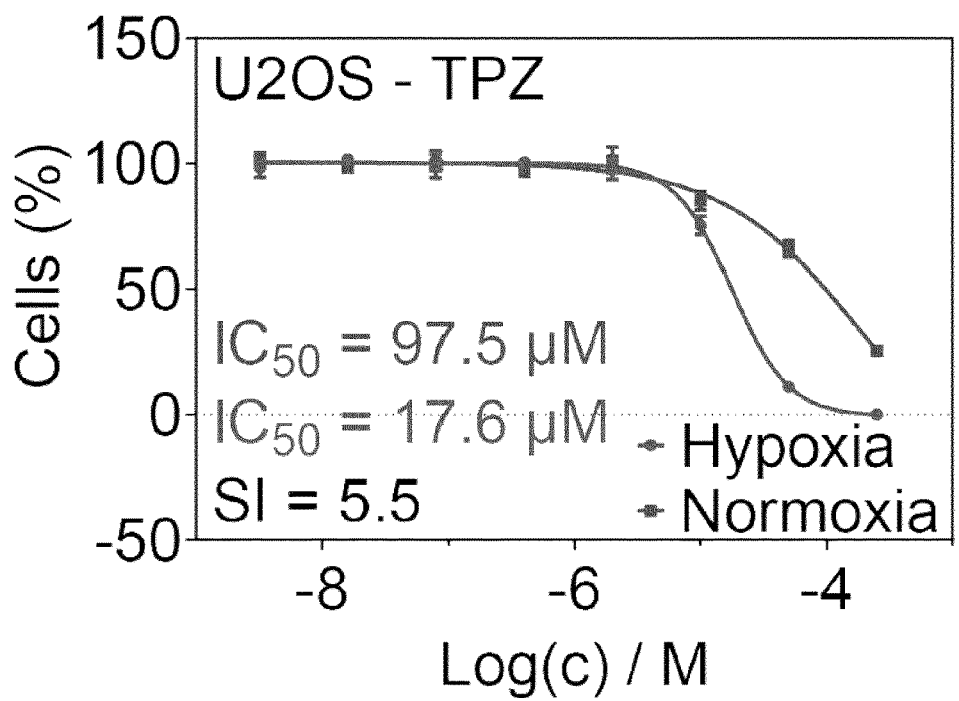
Figure 15:
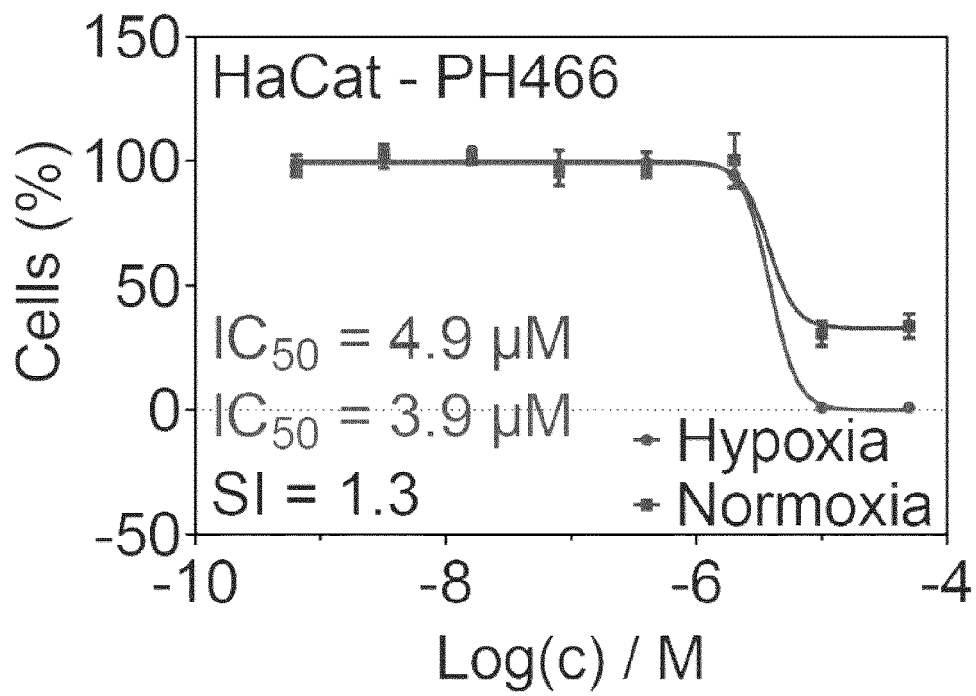
FIG. 15 shows dose-response curves obtained under hypoxic and normoxic conditions when subjecting HaCat cells to A) PH466, and B) TPZ.
Figure 15:
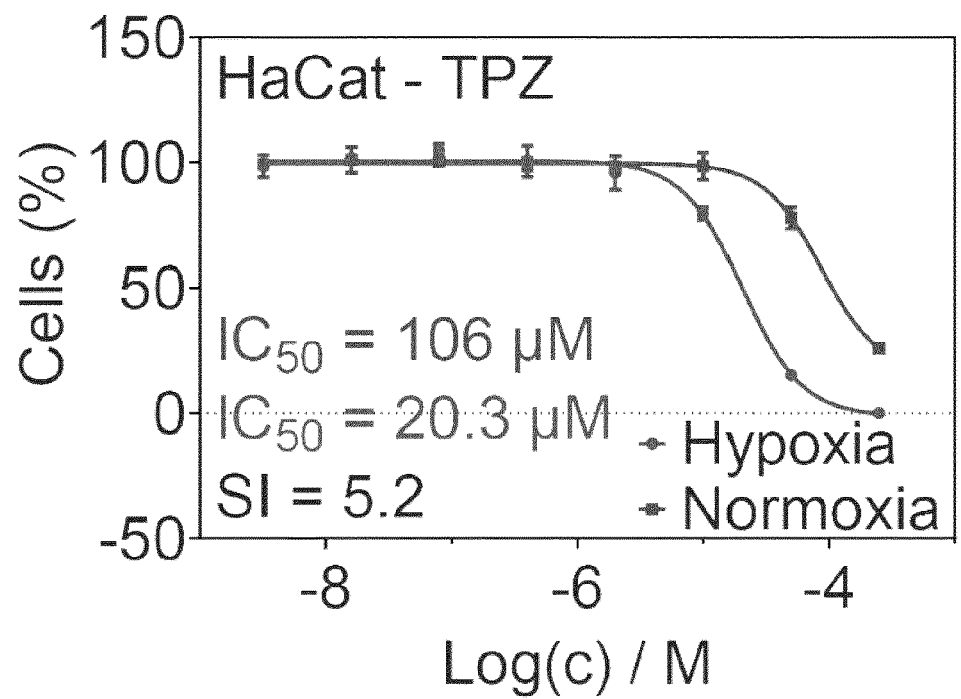
Figure 16:
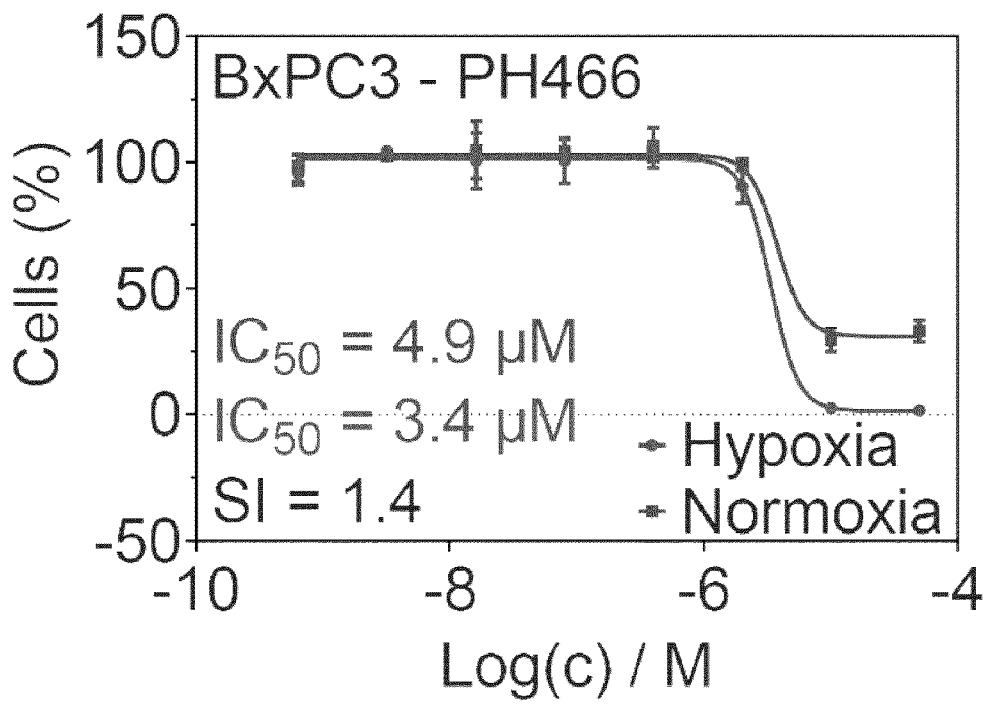
FIG. 16 shows dose-response curves obtained under hypoxic and normoxic conditions when subjecting BxPC3 cells to A) PH466, and B) TH302.
Figure 16:
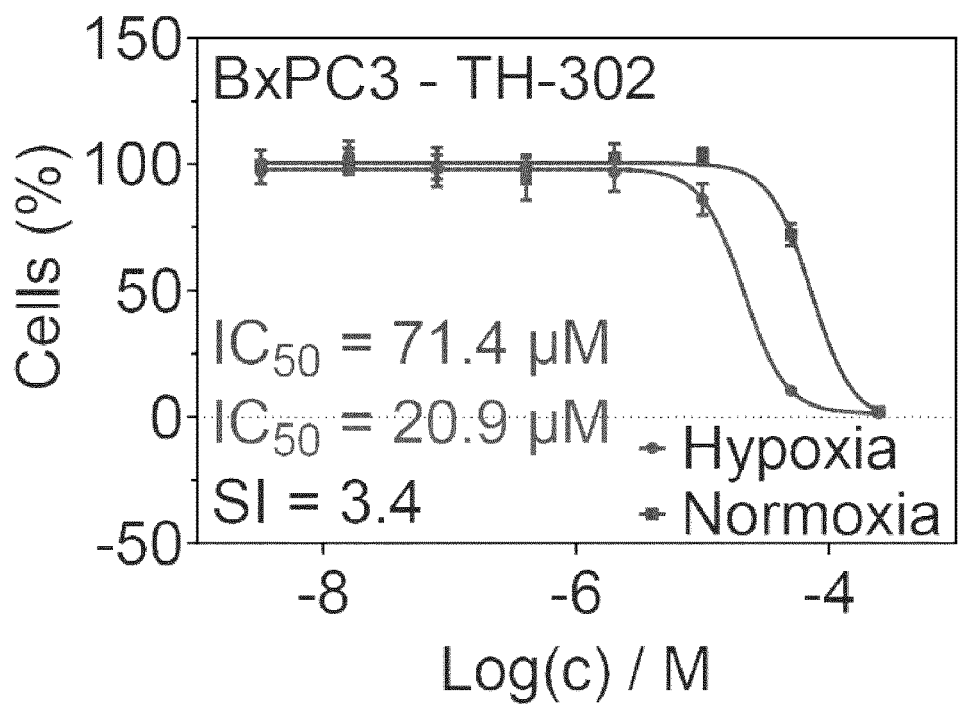
Figure 17:
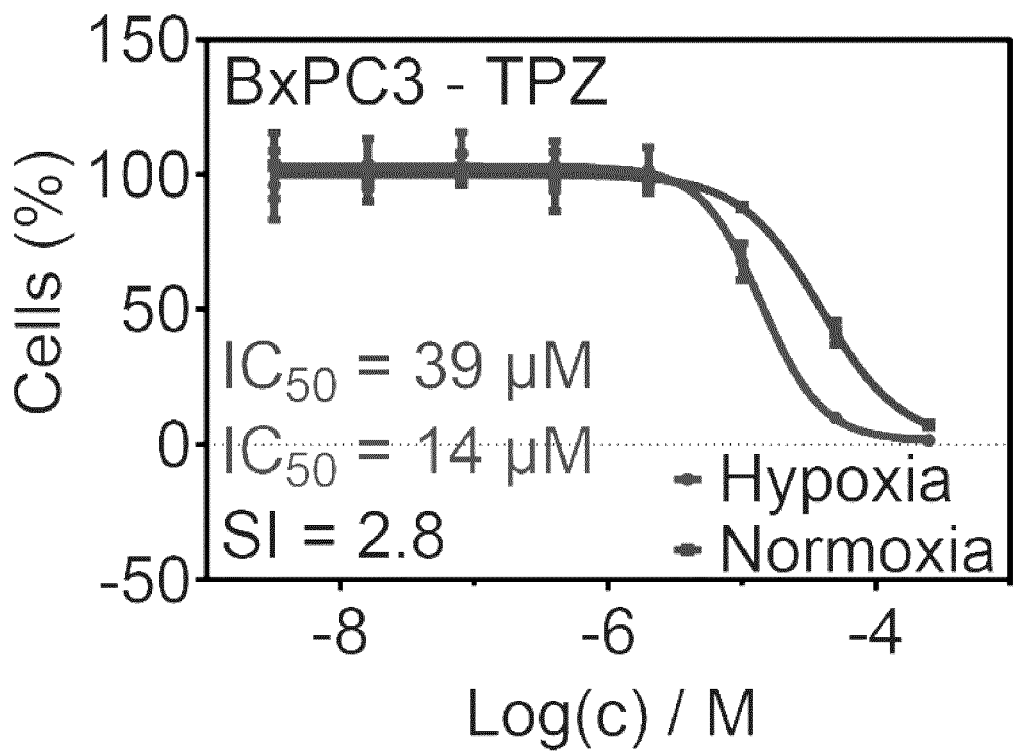
FIG. 17 shows dose-response curves obtained under hypoxic and normoxic conditions when subjecting BxPC3 cells to TPZ.

The data in FIG. 11A, shows that PH466 is stable at both physiological and elevated pH. In comparison, rakicidin D (FIG. 11B) displays decreased stability at elevated pH which might be a consequence of the ester functionality embedded within the macrocyclic ring system.

Example 12—Viability Assays

Figure 9:
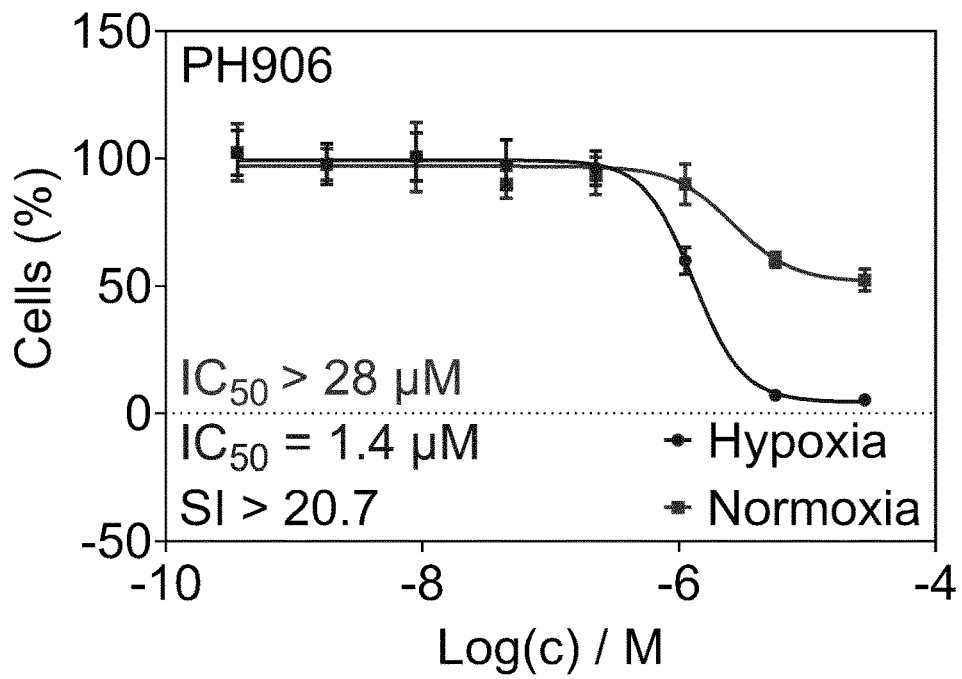
FIG. 9 shows dose-response curves obtained under hypoxic and normoxic conditions when subjecting HCT116 cells to A) PH906, and B) PH911.
Figure 9:
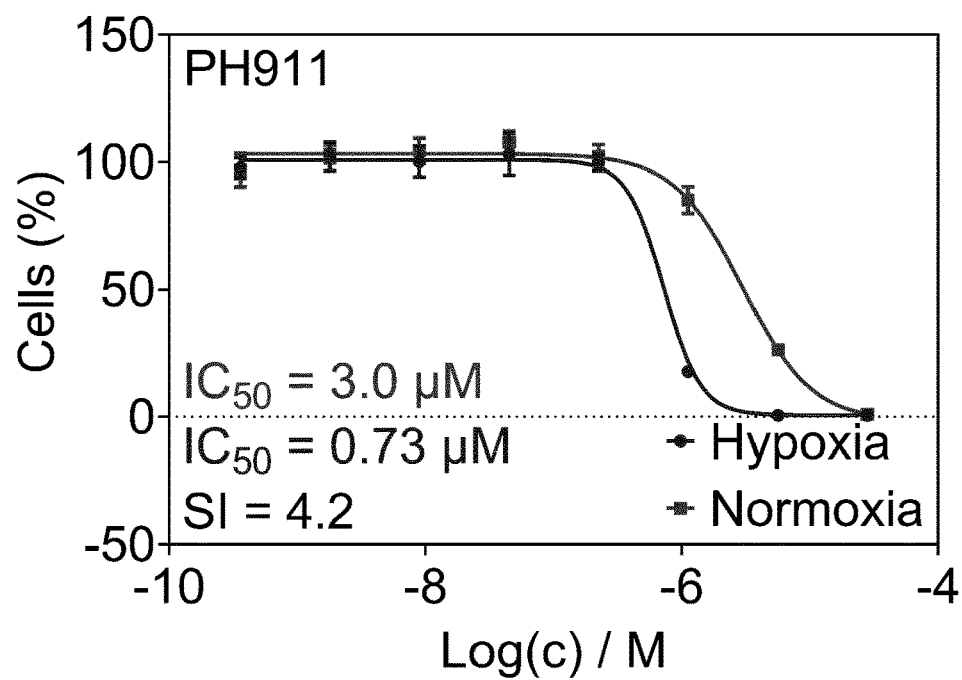
Figure 10:
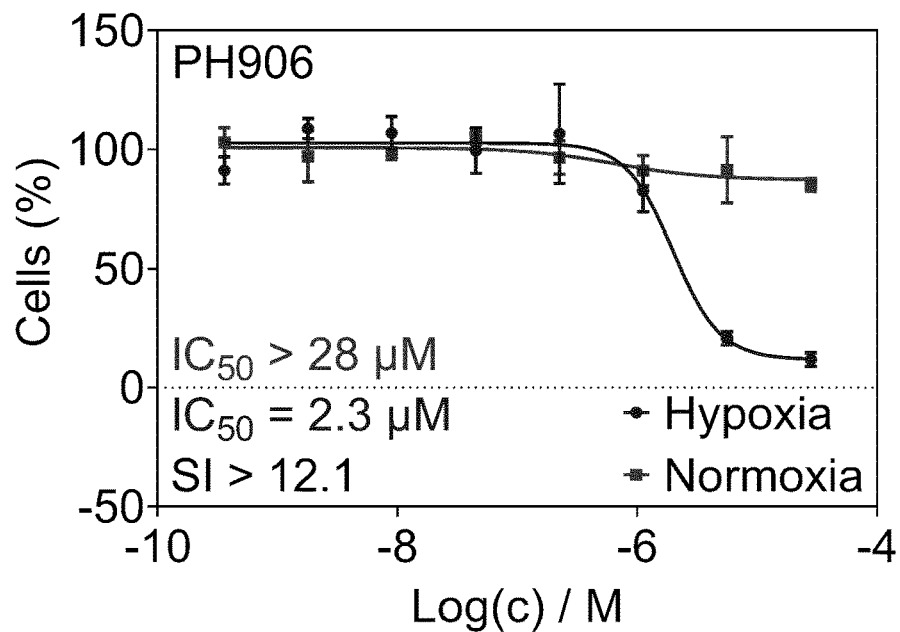
FIG. 10 shows dose-response curves obtained under hypoxic and normoxic conditions when subjecting PANC-1 cells to A) PH906, and B) PH911.
Figure 10:
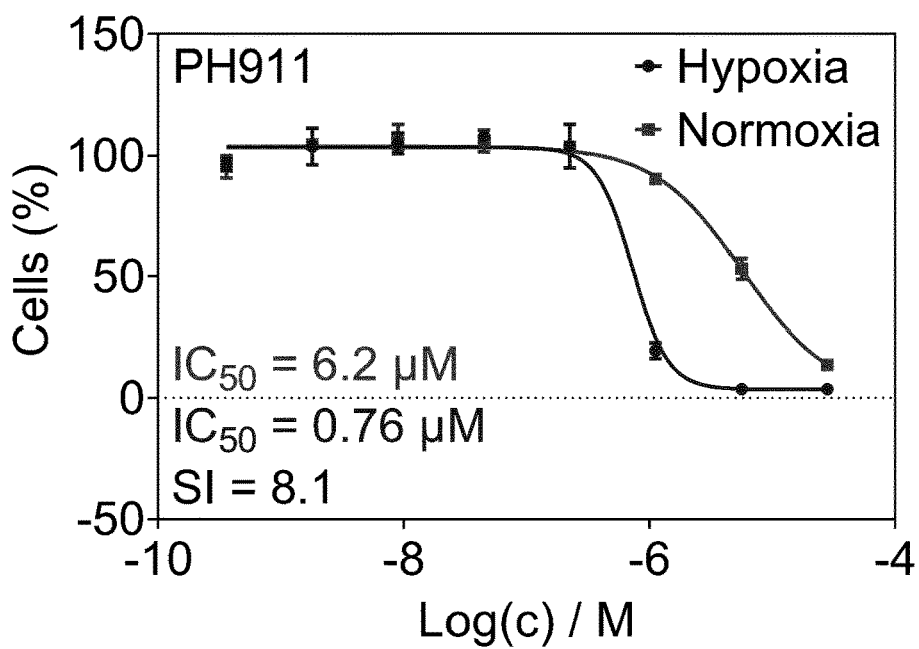

Cells were seeded in black 96-well plates (2000 cells/well, 75 μL/well, ThermoFisher Scientific, Cat #: 137103) in complete medium. Subsequently, the cells were allowed to adhere to the substratum overnight. The next day, compounds were serially diluted in DMSO as 200× solutions. The 200× solutions of compounds were initially diluted in complete medium to 4× solutions containing 2% DMSO. Finally, the compounds were given to cells by the addition of 25 μL/well in triplicates resulting in 1× solutions of compounds in 100 μL/well. The cells were then incubated under either normoxia or hypoxia. 90 minutes before the end of the experiment, all cells were given CellTiter Blue (20 μL/well, Promega, Cat #: G8080) and reincubated under normoxia for the remaining time of the experiment. The viability of the cells was assessed by measuring fluorescence in a plate reader (ex/em: 552±10/598±10, Tecan Spark 10M). Data were normalized to the two lowest concentrations of compound and fitted to a 4-parameter nonlinear regression in Prism 7.04 for Windows, GraphPad Software, La Jolla Calif. USA. $IC_{50}$ values were extrapolated as the X value at Y=50%. Results can be found in Table 1 and the corresponding dose-response curves seen in FIGS. 12 to 17 and in FIGS. 9 to 10.

Tirapazamine and Evofosfamide (TH302) was obtained from Sigma-Aldrich and Selleckchem respectively.

TABLE 1 viability data

| Compound | | Cell lines | | | | |
| --- | --- | --- | --- | --- | --- | --- |
| | | HCT116 | PANC1 | BxPC3 | U2OS | HaCat |
| PH466 | $IC_{50}$ (μM) [1] | 0.98 | 1.8 | 3.4 | 2.1 | 3.9 |
| | $IC_{50}$ (μM) [2] | 4.2 | 4.1 | 4.9 | 3.8 | 4.9 |
| | Index [3] | 4.3 | 2.3 | 1.4 | 1.8 | 1.3 |
| Tirapazamine | $IC_{50}$ (μM) [1] | 14.4 | 11.0 | 14.0 | 98.0 | 20.0 |
| | $IC_{50}$ (μM) [2] | 58.0 | 76.0 | 39.0 | 18.0 | 106.0 |
| | Index [3] | 4.0 | 7.1 | 2.8 | 5.5 | 5.2 |

TABLE 1-continued viability data

| Compound | | Cell lines | | | | |
|---|---|---|---|---|---|---|
| | | HCT116 | PANC1 | BxPC3 | U2OS | HaCat |
| TH302 | $IC_{50}$ (μM) [1] | 6.2 | 9.4 | 21.0 | ND | ND |
| | $IC_{50}$ (μM) [2] | 43 | 69.0 | 71.0 | ND | ND |
| | Index [3] | 6.9 | 7.2 | 3.4 | ND | ND |
| PH832 | $IC_{50}$ (μM) [1] | 5.0 | 4.3 | ND | ND | ND |
| | $IC_{50}$ (μM) [2] | 5.6 | 23.3 | ND | ND | ND |
| | Index [3] | 1.1 | 5.4 | ND | ND | ND |
| PH845 | $IC_{50}$ (μM) [1] | 4.2 | 3.1 | ND | ND | ND |
| | $IC_{50}$ (μM) [2] | >50 | >50 | ND | ND | ND |
| | Index [3] | >12.4 | >16.4 | ND | ND | ND |
| PH741 | $IC_{50}$ (μM) [1] | 3.3 | 7.8 | ND | ND | ND |
| | $IC_{50}$ (μM) [2] | 16.2 | 16.3 | ND | ND | ND |
| | Index [3] | 4.9 | 2.1 | ND | ND | ND |
| PH905 | $IC_{50}$ (μM) [1] | 3.7 | 5.4 | 5.5 | ND | ND |
| | $IC_{50}$ (μM) [2] | 3.5 | 5.8 | 6.3 | ND | ND |
| | Index [3] | 1.0 | 1.1 | 1.1 | ND | ND |
| PH921 | $IC_{50}$ (μM) [1] | 2.6 | 2.6 | 6.0 | ND | ND |
| | $IC_{50}$ (μM) [2] | 8.4 | 13.7 | 12.3 | ND | ND |
| | Index [3] | 3.3 | 5.3 | 2.1 | ND | ND |
| PH911 | $IC_{50}$ (μM) [1] | 0.73 | 0.76 | 1.2 | ND | ND |
| | $IC_{50}$ (μM) [2] | 3.0 | 6.2 | 4.7 | ND | ND |
| | Index [3] | 4.2 | 8.1 | 3.9 | ND | ND |
| PH906 | $IC_{50}$ (μM) [1] | 1.4 | 2.3 | ND | ND | ND |
| | $IC_{50}$ (μM) [2] | >28 | >28 | ND | ND | ND |
| | Index [3] | >20.7 | >12.1 | ND | ND | ND |

[1] Hypoxic conditions,
[2] Normoxic conditions,
[3] Selectivity index ($IC_{50}$ [2]/$IC_{50}$ [1]),
ND = not determined.

The difference in toxicity of PH466 when under hypoxic or normoxic conditions, stands out from the $IC_{50}$ values measured across the entire scope of cell lines. The results prove that the compounds described herein adopt the hypoxic selectivity of the natural APD-CLDs. Furthermore, it is revealed that compound PH466 is at least four times as toxic to the cells as the tested and synthetically available prodrugs tirapazamine and TH302 by comparison of the respective $IC_{50}$ values obtained under hypoxic conditions.

Furthermore, the difference in toxicity of PH845 when under hypoxic or normoxic conditions, and particularly the selectivity index, stands out from the $IC_{50}$ values measured across the entire scope of cell lines. The results prove that the compounds described herein adopt the hypoxic selectivity of the natural APD-CLDs. Furthermore, it is revealed that compound PH845 is at least two-three times as toxic to the cells as the tested and synthetically available prodrugs tirapazamine and TH302 by comparison of the respective $IC_{50}$ values obtained under hypoxic conditions.

PH911 displays very potent hypoxia-selective $IC_{50}$-values outperforming the conventional hypoxia-activated prodrugs TH302 and tirapazamine, while maintaining equal or better selectivity indices of four to eight-fold.

TABLE 2

Cellular activity of negative control compounds

| Compound | | Cell lines | | | | |
|---|---|---|---|---|---|---|
| | | HCT116 | PANC1 | BxPC3 | U2OS | HaCat |
| PH830 | $IC_{50}$ (μM) [1] | >50 | >50 | >50 | ND | ND |
| | $IC_{50}$ (μM) [2] | >50 | >50 | >50 | ND | ND |
| | Index [3] | ND | ND | ND | ND | ND |
| PH462 | $IC_{50}$ (μM) [1] | >50 | >50 | >50 | ND | ND |
| | $IC_{50}$ (μM) [2] | >50 | >50 | >50 | ND | ND |
| | Index [3] | ND | ND | ND | ND | ND |
| PH908 | $IC_{50}$ (μM) [1] | 14.7 | >50 | >50 | ND | ND |
| | $IC_{50}$ (μM) [2] | 17.4 | >50 | >50 | ND | ND |
| | Index [3] | 1.2 | ND | ND | ND | ND |

[1] Hypoxic conditions,
[2] Normoxic conditions,
[3] Selectivity index ($IC_{50}$ [2]/$IC_{50}$ [1]),
ND = not determined.

As is evident from table 2, the compounds without the APD-unit fails to obtain any relevant $IC_{50}$-values in the tested cell lines and thus underscores the importance of the APD-unit for the hypoxia-selective toxicity.

REFERENCES

M. Tsakos et al., Angew. Chem. Int. Ed., 2015, 55, 1030
WO03/076424

The invention claimed is:
1. A compound of Formula (1):

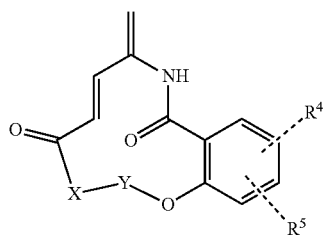

wherein, X is selected from the group consisting of a bond, or —NR$^{N1}$CHR$^1$C(O)—;
for which —' denotes the bond connecting X to Y,
Y is selected from the group consisting of —NR$^{N2}$CR$^2$R$^{2'}$CHR$^3$—*, and —NR$^{N2}$CR$^2$R$^{2'}$CHR$^3$CH$_2$—*, for which —* denotes the bond connecting Y to O,
R$^{N1}$ and R$^{N2}$ are each optionally substituted groups independently selected from the group consisting of hydrogen, (C$_1$-C$_{10}$)alkyl, (C$_2$-C$_{10}$)alkenyl, (C$_2$-C$_{10}$)alkynyl, (C$_1$-C$_{10}$)alkoxy, (C$_1$-C$_{10}$)alkyloxy(C$_1$-C$_{10}$)alkyl, methoxy(C$_1$-C$_6$)alkyl, carboxy(C$_1$-C$_{10}$)alkyl, carbamoyl(C$_1$-C$_{10}$)alkyl, (C$_1$-C$_{10}$)alkyloxycarbonyl(C$_3$-C$_{10}$)alkyl, (C$_1$-C$_{10}$)alkylcarbonyl, cyclo(C$_3$-C$_6$)alkyl, cyclo(C$_3$-C$_6$)alkyl(C$_1$-C$_{10}$)alkyl, fused bicyclyl, heterocyclyl, heterocyclyl(C$_1$-C$_{10}$)alkyl, aryl, aralkyl, heteroaryl, (C$_1$-C$_{10}$)alkylaryl, aryl(C$_1$-C$_{10}$)alkyl, heteroaryl(C$_1$-C$_{10}$)alkyl, (C$_1$-C$_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo(C$_1$-C$_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or R$^{N2}$ is forming an optionally substituted 3-, 4-, 5-, or 6-membered heterocycle together with R$^{2'}$ and the atoms to which they are connected,
R$^1$ is selected from the group consisting of halogen, hydrogen, formyl, azido, nitro, cyano, hydroxy, sulfanyl, amino, carboxy, carbamoyl, —N(R$^{1a}$)$_2$, —C(O)OR$^{1a}$, —(CH$_2$)$_q$C(O)OR$^{1a}$, —C(O)N(R$^{1a}$)$_2$, —(CH$_2$)$_q$C(O)N(R$^{1a}$)$_2$, an optionally substituted group selected from the group consisting of (C$_1$-C$_{10}$)alkyl, (C$_2$-C$_{10}$)alkenyl, (C$_2$-C$_{10}$)alkynyl, (C$_1$-C$_{10}$)alkoxy, (C$_1$-C$_{10}$)alkyloxy(C$_1$-C$_{10}$)alkyl, methoxy(C$_1$-C$_6$)alkyl, carboxy(C$_1$-C$_{10}$)alkyl, carbamoyl(C$_1$-C$_{10}$)alkyl, (C$_1$-C$_{10}$)alkyloxycarbonyl(C$_3$-C$_{10}$)alkyl, (C$_1$-C$_{10}$)alkylcarbonyl, cyclo(C$_3$-C$_6$)alkyl, cyclo(C$_3$-C$_6$)alkyl(C$_1$-C$_{10}$)alkyl, fused bicyclyl, heterocyclyl, heterocyclyl(C$_1$-C$_{10}$)alkyl, aryl, aralkyl, heteroaryl, (C$_1$-C$_{10}$)alkylaryl, aryl(C$_1$-C$_{10}$)alkyl, heteroaryl(C$_1$-C$_{10}$)alkyl, (C$_1$-C$_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo(C$_1$-C$_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil,
R$^2$ and R$^{2'}$ are each independently selected from the group consisting of halogen, hydrogen, formyl, azido, nitro, cyano, hydroxy, sulfanyl, amino, carboxy, carbamoyl, —N(R$^{2a}$)$_2$, —C(O)OR$^{2a}$, —(CH$_2$)$_q$C(O)OR$^{2a}$, —C(O)N(R$^{2a}$)$_2$, —(CH$_2$)$_q$C(O)N(R$^{2a}$)$_2$, —(CH$_2$)$_q$OC(O)R$^{2a}$, —(CH$_2$)$_q$NHC(O)R$^{2a}$, an optionally substituted group selected from the group consisting of (C$_1$-C$_{10}$)alkyl, (C$_2$-C$_{10}$)alkenyl, (C$_2$-C$_{10}$)alkynyl, (C$_1$-C$_{10}$)alkoxy, (C$_1$-C$_{10}$)alkyloxy(C$_1$-C$_{10}$)alkyl, methoxy(C$_1$-C$_6$)alkyl, carboxy(C$_1$-C$_{10}$)alkyl, carbamoyl(C$_1$-C$_{10}$)alkyl, (C$_1$-C$_{10}$)alkyloxycarbonyl(C$_3$-C$_{10}$)alkyl, (C$_1$-C$_{10}$)alkylcarbonyl, cyclo(C$_3$-C$_6$)alkyl, cyclo(C$_3$-C$_6$)alkyl(C$_1$-C$_{10}$)alkyl, fused bicyclyl, heterocyclyl, heterocyclyl(C$_1$-C$_{10}$)alkyl, (C$_1$-C$_{10}$)alkyl heterocyclyl, aryl, aralkyl, heteroaryl, (C$_1$-C$_{10}$)alkylaryl, aryl(C$_1$-C$_{10}$)alkyl, heteroaryl(C$_1$-C$_{10}$)alkyl, (C$_1$-C$_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo(C$_1$-C$_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil,
or R$^2$ is forming an optionally substituted 3-, 4-, 5-, or 6-membered ring together with R$^3$ and the atoms to which they are connected, or R$^{2'}$ is forming an optionally substituted 3-, 4-, 5-, or 6-membered heterocycle together with R$^{2N}$ and the atoms to which they are connected,
R$^3$ is selected from the group consisting of halogen, hydrogen, formyl, azido, nitro, cyano, hydroxy, sulfanyl, amino, carboxy, carbamoyl, —N(R$^{3a}$)$_2$, —C(O)OR$^{3a}$, —(CH$_2$)$_q$C(O)OR$^{3a}$, —C(O)N(R$^{3a}$)$_2$, —(CH$_2$)$_q$C(O)N(R$^{3a}$)$_2$, —(CH$_2$)$_q$OC(O)R$^{3a}$, (CH$_2$)$_q$NHC(O)R$^{3a}$, an optionally substituted group selected from the group consisting of (C$_1$-C$_{10}$)alkyl, (C$_2$-C$_{10}$)alkenyl, (C$_2$-C$_{10}$)alkynyl, (C$_1$-C$_{10}$)alkoxy, (C$_1$-C$_{10}$)alkyloxy(C$_1$-C$_{10}$)alkyl, methoxy(C$_1$-C$_6$)alkyl, carboxy(C$_1$-C$_{10}$)alkyl, carbamoyl(C$_1$-C$_{10}$)alkyl, (C$_1$-C$_{10}$)alkyloxycarbonyl(C$_3$-C$_{10}$)alkyl, (C$_1$-C$_{10}$)alkylcarbonyl, cyclo(C$_3$-C$_6$)alkyl, cyclo(C$_3$-C$_6$)alkyl(C$_1$-C$_{10}$)alkyl, fused bicyclyl, heterocyclyl, heterocyclyl(C$_1$-C$_{10}$)alkyl, (C$_1$-C$_{10}$)alkyl heterocyclyl, aryl, aralkyl, heteroaryl, (C$_1$-C$_{10}$)alkylaryl, aryl(C$_1$-C$_{10}$)alkyl, heteroaryl(C$_1$-C$_{10}$)alkyl, (C$_1$-C$_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo(C$_1$-C$_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or R$^3$ is forming an optionally substituted 3-, 4-, 5-, or 6-membered ring together with R$^2$ and the atoms to which they are connected,
R$^4$ and R$^5$ are each independently selected from the group consisting of halogen, hydrogen, formyl, azido, nitro, cyano, hydroxy, sulfanyl, amino, carboxy, carbamoyl, —N(R$^{4a}$)$_2$, —OR$^{4a}$, —C(O)OR$^{4a}$, —(CH$_2$)$_q$C(O)OR$^{4a}$, —C(O)N(R$^{4a}$)$_2$, —(CH$_2$)$_q$C(O)N(R$^{4a}$)$_2$, —(CH$_2$)$_q$OC(O)R$^{4a}$, —(CH$_2$)$_q$NHC(O)R$^{4a}$, an optionally substituted group selected from the group consisting of (C$_1$-C$_{18}$)alkyl, (C$_2$-C$_{18}$)alkenyl, (C$_2$-C$_{18}$)alkynyl, (C$_1$-C$_{18}$)alkoxy, (C$_1$-C$_{18}$)alkyloxy(C$_1$-C$_{18}$)alkyl, methoxy(C$_1$-C$_6$)alkyl, carboxy(C$_1$-C$_{10}$)alkyl, carbamoyl(C$_1$-C$_{10}$)alkyl, (C$_1$-C$_{10}$)alkyloxycarbonyl(C$_3$-C$_{10}$)alkyl, (C$_1$-C$_{10}$)alkylcarbonyl, cyclo(C$_3$-C$_6$)alkyl, cyclo(C$_3$-C$_6$)alkyl(C$_1$-C$_{18}$)alkyl, fused bicyclyl, heterocyclyl, heterocyclyl(C$_1$-C$_{18}$)alkyl, aryl, aralkyl, heteroaryl, (C$_1$-C$_{18}$)alkylaryl, aryl(C$_1$-C$_{18}$)alkyl, heteroaryl($C_1$-$C_{18}$)alkyl, ($C_1$-$C_{18}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo($C_1$-$C_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, $R^{1a}$, $R^{2a}$, $R^{3a}$, and $R^{4a}$ are each optionally substituted groups independently selected from the group consisting of hydrogen, ($C_1$-$C_{10}$)alkyl, ($C_2$-$C_{10}$)alkenyl, ($C_2$-$C_{10}$)alkynyl, ($C_1$-$C_{10}$)alkoxy, ($C_1$-$C_{10}$)alkyloxy($C_1$-$C_{10}$)alkyl, methoxy($C_1$-$C_6$)alkyl, carboxy($C_1$-$C_{10}$)alkyl, carbonyl($C_1$-$C_{10}$)alkyl, N—($C_1$-$C_{10}$)alkyl-N—($C_1$-$C_{10}$)alkylaminocarbonyl($C_1$-$C_{10}$)alkyl, ($C_1$-$C_{10}$)alkyloxycarbonyl($C_1$-$C_{10}$)alkyl, ($C_1$-$C_{10}$)alkylcarbonyl, cyclo($C_3$-$C_6$)alkyl, cyclo($C_3$-$C_6$)alkyl($C_1$-$C_{10}$)alkyl, fused bicyclyl, heterocyclyl, heterocyclyl($C_1$-$C_{10}$)alkyl, aryl, aralkyl, heteroaryl, ($C_1$-$C_{10}$)alkylaryl, aryl($C_1$-$C_{10}$)alkyl, heteroaryl($C_1$-$C_{10}$)alkyl, ($C_1$-$C_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo($C_1$-$C_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or wherein two identical $R^{1a}$, $R^{2a}$, $R^{3a}$, or $R^{4a}$ together form an optionally substituted 4-, 5- or 6-membered heterocycle comprising the heteroatom to which both groups are connected; q is an integer selected from the group consisting of 1, 2, 3, 4, 5, 6, 7, 8, 9 and 10.

2. The compound according to claim 1, wherein:

X is —$NR^{N1}CHR^1C(O)$—';

Y is —$NR^{N2}CR^2R^{2'}CHR^3$—*;

$R^{N1}$ is methyl;

$R^1$ is selected from the group consisting of halogen, hydrogen, formyl, azido, nitro, cyano, hydroxy, sulfanyl, amino, carboxy, carbamoyl, —$N(R^{1a})_2$, —$C(O)OR^{1a}$, —$(CH_2)_qC(O)OR^{1a}$, —$C(O)N(R^{1a})_2$, —$(CH_2)_qC(O)N(R^{1a})_2$, an optionally substituted group selected from the group consisting of ($C_1$-$C_{10}$)alkyl, ($C_2$-$C_{10}$)alkenyl, ($C_2$-$C_{10}$)alkynyl, ($C_1$-$C_{10}$)alkoxy, ($C_1$-$C_{10}$)alkyloxy($C_1$-$C_{10}$)alkyl, methoxy($C_1$-$C_6$)alkyl, carboxy($C_1$-$C_{10}$)alkyl, carbamoyl($C_1$-$C_{10}$)alkyl, ($C_1$-$C_{10}$)alkyloxycarbonyl($C_3$-$C_{10}$)alkyl, ($C_1$-$C_{10}$)alkylcarbonyl, cyclo($C_3$-$C_6$)alkyl, cyclo($C_3$-$C_6$)alkyl($C_1$-$C_{10}$)alkyl, fused bicyclyl, heterocyclyl, heterocyclyl($C_1$-$C_{10}$)alkyl, aryl, aralkyl, heteroaryl, ($C_1$-$C_{10}$)alkylaryl, aryl($C_1$-$C_{10}$)alkyl, heteroaryl($C_1$-$C_{10}$)alkyl, ($C_1$-$C_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo($C_1$-$C_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil;

$R^{N2}$ is an optionally substituted groups independently selected from the group consisting of hydrogen, ($C_1$-$C_{10}$)alkyl, ($C_2$-$C_{10}$)alkenyl, ($C_2$-$C_{10}$)alkynyl, ($C_1$-$C_{10}$)alkoxy, ($C_1$-$C_{10}$)alkyloxy($C_1$-$C_{10}$)alkyl, methoxy($C_1$-$C_6$)alkyl, carboxy($C_1$-$C_{10}$)alkyl, carbamoyl($C_1$-$C_{10}$)alkyl, ($C_1$-$C_{10}$)alkyloxycarbonyl($C_3$-$C_{10}$)alkyl, ($C_1$-$C_{10}$)alkylcarbonyl, cyclo($C_3$-$C_6$)alkyl, cyclo($C_3$-$C_6$)alkyl($C_1$-$C_{10}$)alkyl, fused bicyclyl, heterocyclyl, heterocyclyl($C_1$-$C_{10}$)alkyl, aryl, aralkyl, heteroaryl, ($C_1$-$C_{10}$)alkylaryl, aryl($C_1$-$C_{10}$)alkyl, heteroaryl($C_1$-$C_{10}$)alkyl, ($C_1$-$C_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo($C_1$-$C_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or $R^{N2}$ is forming an optionally substituted 3-, 4-, 5-, or 6-membered heterocycle together with $R^{2'}$ and the atoms to which they are connected;

$R^2$ and $R^{2'}$ are each independently selected from the group consisting of halogen, hydrogen, formyl, azido, nitro, cyano, hydroxy, sulfanyl, amino, carboxy, carbamoyl, —$N(R^{2a})_2$, —$C(O)OR^{2a}$, —$(CH_2)_qC(O)OR^{2a}$, —$C(O)N(R^{2a})_2$, —$(CH_2)_qC(O)N(R^{2a})_2$, —$(CH_2)_qOC(O)R^{2a}$, —$(CH_2)_qNHC(O)R^{2a}$, an optionally substituted group selected from the group consisting of ($C_1$-$C_{10}$)alkyl, ($C_2$-$C_{10}$)alkenyl, ($C_2$-$C_{10}$)alkynyl, ($C_1$-$C_{10}$)alkoxy, ($C_1$-$C_{10}$)alkyloxy($C_1$-$C_{10}$)alkyl, methoxy($C_1$-$C_6$)alkyl, carboxy($C_1$-$C_{10}$)alkyl, carbamoyl($C_1$-$C_{10}$)alkyl, ($C_1$-$C_{10}$)alkyloxycarbonyl($C_3$-$C_{10}$)alkyl, ($C_1$-$C_{10}$)alkylcarbonyl, cyclo($C_3$-$C_6$)alkyl, cyclo($C_3$-$C_6$)alkyl($C_1$-$C_{10}$)alkyl, fused bicyclyl, heterocyclyl, heterocyclyl($C_1$-$C_{10}$)alkyl, ($C_1$-$C_{10}$)alkyl heterocyclyl, aryl, aralkyl, heteroaryl, ($C_1$-$C_{10}$)alkylaryl, aryl($C_1$-$C_{10}$)alkyl, heteroaryl($C_1$-$C_{10}$)alkyl, ($C_1$-$C_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo($C_1$-$C_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or $R^2$ is forming an optionally substituted 3-, 4-, 5-, or 6-membered ring together with $R^3$ and the atoms to which they are connected, or $R^{2'}$ is forming an optionally substituted 3-, 4-, 5-, or 6-membered heterocycle together with $R^{2N}$ and the atoms to which they are connected;

$R^3$ is selected from the group consisting of halogen, hydrogen, formyl, azido, nitro, cyano, hydroxy, sulfanyl, amino, carboxy, carbamoyl, —$N(R^{3a})_2$, —$C(O)OR^{3a}$, —$(CH_2)_qC(O)OR^{3a}$, —$C(O)N(R^{3a})_2$, —$(CH_2)_qC(O)N(R^{3a})_2$, —$(CH_2)_qOC(O)R^{3a}$, —$(CH_2)_qNHC(O)R^{3a}$, an optionally substituted group selected from the group consisting of ($C_1$-$C_{10}$)alkyl, ($C_2$-$C_{10}$)alkenyl, ($C_2$-$C_{10}$)alkynyl, ($C_1$-$C_{10}$)alkoxy, ($C_1$-$C_{10}$)alkyloxy($C_1$-$C_{10}$)alkyl, methoxy($C_1$-$C_6$)alkyl, carboxy($C_1$-$C_{10}$)alkyl, carbamoyl($C_1$-$C_{10}$)alkyl, ($C_1$-$C_{10}$)alkyloxycarbonyl($C_3$-$C_{10}$)alkyl, ($C_1$-$C_{10}$)alkylcarbonyl, cyclo($C_3$-$C_6$)alkyl, cyclo($C_3$-$C_6$)alkyl($C_1$-$C_{10}$)alkyl, fused bicyclyl, heterocyclyl, heterocyclyl($C_1$-$C_{10}$)alkyl, ($C_1$-$C_{10}$)alkyl heterocyclyl, aryl, aralkyl, heteroaryl, ($C_1$-$C_{10}$)alkylaryl, aryl($C_1$-$C_{10}$)alkyl, heteroaryl($C_1$-$C_{10}$)alkyl, ($C_1$-$C_{10}$)alkylheteroaryl, aryloxyaryl, heteroaryloxyheteroaryl, heteroaryloxyaryl, aryloxyheteroaryl, heteroarylaryl, arylheteroaryl, biaryl, oxocyclo($C_1$-$C_6$)alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or $R^3$ is forming an optionally substituted 3-, 4-, 5-, or 6-membered ring together with $R^2$ and the atoms to which they are connected;

$R^{1a}$, $R^{2a}$, and $R^{3a}$ are each optionally substituted groups independently selected from the group consisting of hydrogen, $(C_1\text{-}C_{10})$alkyl, $(C_2\text{-}C_{10})$alkenyl, $(C_2\text{-}C_{10})$alkynyl, $(C_1\text{-}C_{10})$alkoxy, $(C_1\text{-}C_{10})$alkyloxy$(C_1\text{-}C_{10})$alkyl, methoxy$(C_1\text{-}C_6)$alkyl, carboxy$(C_1\text{-}C_{10})$alkyl, carbonyl$(C_1\text{-}C_{10})$alkyl, N—$(C_1\text{-}C_{10})$alkyl-N—$(C_1\text{-}C_{10})$alkylaminocarbonyl$(C_1\text{-}C_{10})$alkyl, $(C_1\text{-}C_{10})$alkyloxycarbonyl$(C_1\text{-}C_{10})$alkyl, $(C_1\text{-}C_{10})$alkylcarbonyl, cyclo$(C_3\text{-}C_6)$alkyl, cyclo$(C_3\text{-}C_6)$alkyl$(C_1\text{-}C_{10})$alkyl, fused bicyclyl, heterocyclyl, heterocyclyl$(C_1\text{-}C_{10})$alkyl, aryl, aralkyl, heteroaryl, $(C_1\text{-}C_{10})$alkylaryl, aryl$(C_1\text{-}C_{10})$alkyl, heteroaryl$(C_1\text{-}C_{10})$alkyl, $(C_1\text{-}C_{10})$alkylheteroaryl, aryloxyaryl, heteroaryloxyheteroaryl, heteroaryloxyaryl, aryloxyheteroaryl, heteroarylaryl, arylheteroaryl, biaryl, oxocyclo$(C_1\text{-}C_6)$alkyl, radical of (α-, β-, γ-, or δ-)lactam, radical of (α-, β-, γ-, or δ-)lactone, radical of sulfolane, radical of succinimide, radical of oxazolidone, radical of hydantoin, radical of cytosine, radical of thymine, and radical of uracil, or wherein two identical $R^{1a}$, $R^{2a}$, or $R^{3a}$ together form an optionally substituted 4-, 5- or 6-membered heterocycle comprising the heteroatom to which both groups are connected; q is an integer selected from the group consisting of 1, 2, 3, 4, 5, 6, 7, 8, 9 and 10.

3. The compound according to claim 1, wherein the compound is represented by formula (2):

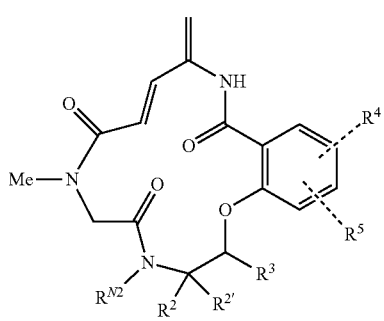

(2)

wherein $R^{N2}$ is selected from the group consisting of hydrogen, methyl, ethyl, isopropyl, benzyl, trifluoromethyl, and trifluoroethyl, or $R^{N2}$ is forming an optionally substituted 3-, 4-, 5-, or 6-membered heterocycle together with $R^{2'}$ and the atoms to which they are connected, $R^2$ and $R^{2'}$ are each independently selected from the group consisting of hydrogen, cyano, carboxy, carbamoyl, —$(CH_2)_qC(O)OR^{2a}$, —$(CH_2)_qC(O)N(R^{2a})_2$, —$(CH_2)_qOC(O)R^{2a}$, —$(CH_2)_qNHC(O)R^{2a}$, an optionally substituted group selected from the group consisting of $(C_1\text{-}C_{10})$alkyl, $(C_2\text{-}C_{10})$alkenyl, $(C_2\text{-}C_{10})$alkynyl, $(C_1\text{-}C_{10})$alkyloxy$(C_1\text{-}C_{10})$alkyl, cyclo$(C_3\text{-}C_6)$alkyl, heterocyclyl, heterocyclyl$(C_1\text{-}C_{10})$alkyl, $(C_1\text{-}C_{10})$alkyl heterocyclyl, aryl, aralkyl, heteroaryl, $(C_1\text{-}C_{10})$alkylaryl, aryl$(C_1\text{-}C_{10})$alkyl, heteroaryl$(C_1\text{-}C_{10})$alkyl, $(C_1\text{-}C_{10})$alkylheteroaryl, oxocyclo$(C_1\text{-}C_6)$alkyl, radical of (α-, β-, γ-, or δ-)lactam, and a radical of (α-, β-, γ-, or δ-)lactone, or $R^2$ is forming an optionally substituted 3-, 4-, 5-, or 6-membered ring together with $R^{2'}$ and the atoms to which they are connected, or $R^{2'}$ is forming an optionally substituted 3-, 4-, 5-, or 6-membered heterocycle together with $R^{2N}$ and the atoms to which they are connected, $R^3$ is selected from the group consisting of hydrogen, carboxy, carbamoyl, —$(CH_2)_qC(O)OR^{3a}$, —$(CH_2)_qC(O)N(R^{3a})_2$, —$(CH_2)_qOC(O)R^{3a}$, —$(CH_2)_qNHC(O)R^{3a}$, an optionally substituted group selected from the group consisting of $(C_1\text{-}C_{10})$alkyl, $(C_1\text{-}C_{10})$alkyloxy$(C_1\text{-}C_{10})$alkyl, cyclo$(C_3\text{-}C_6)$alkyl, heterocyclyl, heterocyclyl$(C_1\text{-}C_{10})$alkyl, $(C_1\text{-}C_{10})$alkyl heterocyclyl, aryl, aralkyl, heteroaryl, $(C_1\text{-}C_{10})$alkylaryl, and $(C_1\text{-}C_{10})$alkylheteroaryl, or $R^3$ is forming an optionally substituted 3-, 4-, 5-, or 6-membered ring together with $R^2$ and the atoms to which they are connected, $R^4$ and $R^5$ are each independently selected from the group consisting of halogen, hydrogen, —$N(R^{4a})_2$, —$OR^{4a}$, —$(CH_2)_qC(O)OR^{4a}$, —$(CH_2)_qC(O)N(R^{4a})_2$, —$(CH_2)_qOC(O)R^{4a}$, —$(CH_2)_qNHC(O)R^{4a}$, an optionally substituted group selected from the group consisting of $(C_1\text{-}C_{18})$alkyl, $(C_1\text{-}C_{18})$alkyloxy$(C_1\text{-}C_{18})$alkyl, cyclo$(C_3\text{-}C_6)$alkyl, cyclo$(C_3\text{-}C_6)$alkyl$(C_1\text{-}C_{18})$alkyl, fused bicyclyl, heterocyclyl, heterocyclyl$(C_1\text{-}C_{18})$alkyl, aryl, aralkyl, heteroaryl, $(C_1\text{-}C_{18})$alkylaryl, aryl$(C_1\text{-}C_{18})$alkyl, heteroaryl$(C_1\text{-}C_{18})$alkyl, and $(C_1\text{-}C_{18})$alkylheteroaryl, $R^{2a}$, $R^{3a}$, and $R^{4a}$ are each optionally substituted groups independently selected from the group consisting of hydrogen, $(C_1\text{-}C_{10})$alkyl, $(C_2\text{-}C_{10})$alkenyl, $(C_2\text{-}C_{10})$alkynyl, $(C_1\text{-}C_{10})$alkoxy, $(C_1\text{-}C_{10})$alkyloxy$(C_1\text{-}C_{10})$alkyl, carboxy$(C_1\text{-}C_{10})$alkyl, carbonyl$(C_1\text{-}C_{10})$alkyl, cyclo$(C_3\text{-}C_6)$alkyl, cyclo$(C_3\text{-}C_6)$alkyl$(C_1\text{-}C_{10})$alkyl, fused bicyclyl, heterocyclyl, heterocyclyl$(C_1\text{-}C_{10})$alkyl, aryl, aralkyl, heteroaryl, $(C_1\text{-}C_{10})$alkylaryl, aryl$(C_1\text{-}C_{10})$alkyl, heteroaryl$(C_1\text{-}C_{10})$alkyl, and $(C_1\text{-}C_{10})$alkylheteroaryl, or wherein two identical $R^{2a}$, $R^{3a}$, or $R^{4a}$ together form an optionally substituted 4-, 5- or 6-membered heterocycle comprising the heteroatom to which both groups are connected; q is an integer selected from the group consisting of 1, 2, 3, 4, 5, 6, 7, 8, 9 and 10.

4. The compound according to claim 1, wherein the optionally substituted 3-, 4-, 5-, or 6-membered heterocycle formed by $R^{N2}$ and $R^{2'}$ and the atoms to which they are connected is an optionally substituted 5- or 6-membered heterocycle.

5. The compound according to claim 1, wherein the optionally substituted 5-, or 6-membered heterocycle formed by $R^{N2}$ and $R^{2'}$ and the atoms to which they are connected is selected from the group consisting of (γ-, or δ-)lactam, pyrrolidine, pyrroline, pyrazolidine, imidazolidine, pyrazoline, imidazoline, oxazolidone, hydantoin, piperidine, piperazine, morpholine, thiomorpholine, and diazinane.

6. The compound according to claim 1, wherein the optionally substituted 3-, 4-, 5-, or 6-membered ring formed by $R^2$ and $R^3$ and the atoms to which they are connected is an optionally substituted 5- or 6-membered ring.

7. The compound according to claim 1, wherein the optionally substituted 5-, or 6-membered ring formed by $R^2$ and $R^3$ and the atoms to which they are connected is selected from the group consisting of (γ-, or δ-)lactam, (γ-, or δ-)lactone, cyclopentane, pyrrolidine, pyrroline, pyrazolidine, imidazolidine, pyrazoline, imidazoline, tetrahydrofuran, dioxolane, tetrahydrothiophene, oxathiolane, sulfolane, succinimide, oxazolidone, cyclohexane, piperidine, piperazine, tetrahydropyran, dioxane, thiane, dithiane, morpholine, thiomorpholine, and diazinane.

8. The compound according to claim 1, wherein the optionally substituted 4-, 5- or 6-membered heterocycle formed by two identical $R^{1a}$, $R^{2a}$, $R^{3a}$, or $R^{4a}$ and the heteroatom to which both groups are connected is an optionally substituted 5- or 6-membered heterocycle.

9. The compound according to claim 1, wherein the optionally substituted 5- or 6-membered heterocycle formed by two identical $R^{1a}$, $R^{2a}$, $R^{3a}$, or $R^{4a}$ and the heteroatom to which both groups are connected is selected from the group consisting of piperidine, pyrroline, pyrrole, pyrazolidine, imidazolidine, pyrazoline, imidazoline, pyrazole, imidazole, triazole, tetrazole, thiazolidinedione, succinimide, oxazolidone, hydantoin, piperidine, piperazine, morpholine, oxazine, thiomorpholine, thiazine, thymine, and uracil.

10. The compound according to claim 1, wherein the optional substituents on $R^{N1}$, $R^{N2}$, $R^1$, $R^2$, $R^{2'}$, $R^3$, $R^4$, $R^5$, $R^{1a}$, $R^{2a}$, $R^{3a}$, and $R^{4a}$ are each independently selected from the group consisting of halogen, methyl, silyl, azido, amino, nitro, cyano, hydroxy, sulfanyl, carboxy, and carbamoyl.

11. The compound according to claim 1, wherein the optional substituents on the rings and the heterocycles are a number of 1 to 3 substituents that are each independently selected from the group consisting of halogen, methyl, silyl, azido, amino, nitro, cyano, hydroxy, sulfanyl, carboxy, carbamoyl, and carbonyl.

12. The compound according to claim 1, wherein the compound is represented by formula (2a):

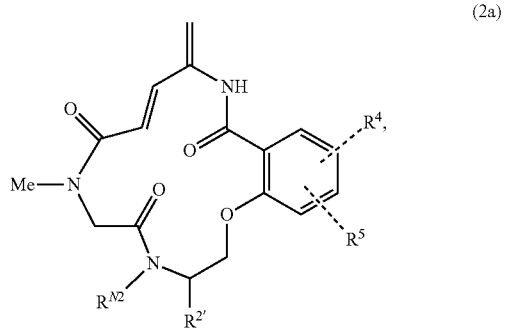

(2a)

wherein, $R^{N2}$ is hydrogen and $R^{2'}$ is selected from the group consisting of hydrogen, $-(CH_2)_qC(O)OR^{2a}$, $-(CH_2)_qC(O)N(R^{2a})_2$, and $-(CH_2)_qNHC(O)R^{2a}$, or $R^{2'}$ is forming an optionally substituted 5- or 6-membered heterocycle together with $R^{2N}$ which heterocycle is selected from the group consisting of (γ-, or δ-)lactam, pyrrolidine, pyrroline, pyrazolidine, imidazolidine, pyrazoline, imidazoline, oxazolidone, hydantoin, piperidine, piperazine, morpholine, thiomorpholine, and diazinane; q is an integer selected from the group consisting of 1, 2, 3, 4, 5, 6, 7, 8, 9 and 10; $R^{2a}$ is independently selected from the group consisting of hydrogen, $(C_1-C_{10})$alkyl, $(C_2-C_{10})$alkenyl, $(C_1-C_{10})$alkoxy, $(C_2-C_{10})$alkynyl, carboxy$(C_1-C_{10})$alkyl, cyclo$(C_3-C_6)$alkyl, cyclo$(C_3-C_6)$alkyl$(C_1-C_{10})$alkyl, fused bicyclyl, heterocyclyl$(C_1-C_{10})$alkyl, aralkyl, aryl$(C_1-C_{10})$alkyl, and heteroaryl$(C_1-C_{10})$alkyl, or $R^{2a}$ is forming an optionally substituted 4-, 5- or 6-membered heterocycle together with another $R^{2a}$ which heterocycle comprises the heteroatom to which both groups are connected and is selected from the group consisting of piperidine, pyrroline, pyrrole, pyrazolidine, imidazolidine, pyrazoline, imidazoline, pyrazole, imidazole, triazole, tetrazole, thiazolidinedione, succinimide, oxazolidone, hydantoin, piperidine, piperazine, morpholine, oxazine, thiomorpholine, thiazine, thymine, and uracil;

$R^4$ and $R^5$ are independently selected from the group consisting of hydrogen, an optionally substituted group selected from the group consisting of $(C_1-C_{18})$alkyl, $(C_1-C_{18})$alkyloxy$(C_1-C_{18})$alkyl, cyclo$(C_3-C_6)$alkyl$(C_1-C_{18})$alkyl, heterocyclyl$(C_1-C_{18})$alkyl, aryl, heteroaryl, aryl$(C_1-C_{18})$alkyl, and heteroaryl$(C_1-C_{18})$alkyl.

13. The compound according to claim 12, wherein $R^{N2}$ is hydrogen and $R^{2'}$ is selected from the group consisting of hydrogen, $-(CH_2)_qC(O)OR^{2a}$, $-(CH_2)_qC(O)N(R^{2a})_2$, and $-(CH_2)_qNHC(O)R^{2a}$, or $R^{2'}$ together with $R^{2N}$ form an optionally substituted pyrrolidine heterocycle; q is an integer selected from the group consisting of 1, 2, 3, 4, 5 and 6; $R^{2a}$ is independently selected from the group consisting of hydrogen, $(C_1-C_{10})$alkyl, $(C_2-C_{10})$alkenyl, $(C_1-C_{10})$alkoxy, $(C_2-C_{10})$alkynyl and cyclo$(C_3-C_6)$alkyl, or $R^{2a}$ together with another $R^{2a}$ form an optionally substituted morpholine heterocycle; $R^4$ and $R^5$ are independently selected from the group consisting of hydrogen, and $(C_1-C_{18})$alkyl; the optional substituents for the heterocycles are a number of 1 to 3 substituents that are each independently selected from the group consisting of chloro, fluoro, bromo, iodo, and fluoro, optionally wherein the $(C_1-C_{10})$alkyl is a radical selected from the group consisting of methyl, ethyl, propyl, isopropyl, butyl, tert-butyl, pentyl, hexyl, heptyl, octyl, nonyl, decyl, and methyl, and optionally wherein the cyclo$(C_3-C_6)$alkyl is a radical selected from the group consisting of cyclopropyl, cyclobutyl, cyclopentyl, and cyclohexyl.

14. The compound according to claim 12, wherein the $(C_1-C_{10})$alkoxy is a radical selected from the group consisting of methoxy, ethoxy, propoxy, isopropoxy, butyloxy, tert-butyloxy, pentyloxy, hexyloxy, heptyloxy, octyloxy, nonyloxy, decyloxy, and tert-butyloxy, optionally wherein the $(C_2-C_{10})$alkynyl is a radical selected from the group consisting of ethynyl, propargyl, butynyl, pentynyl, hexynyl, and propargyl.

15. The compound according to claim 12, wherein the compound is selected from the group consisting of:

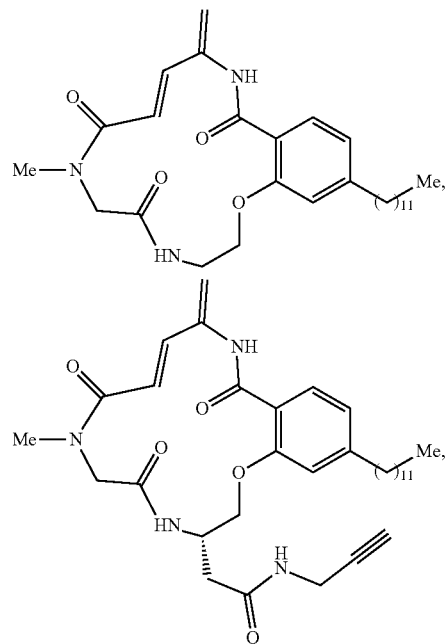

-continued
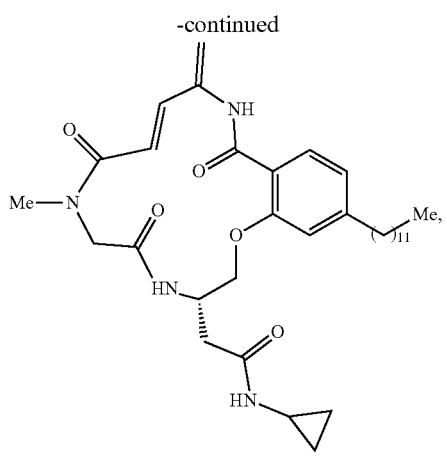
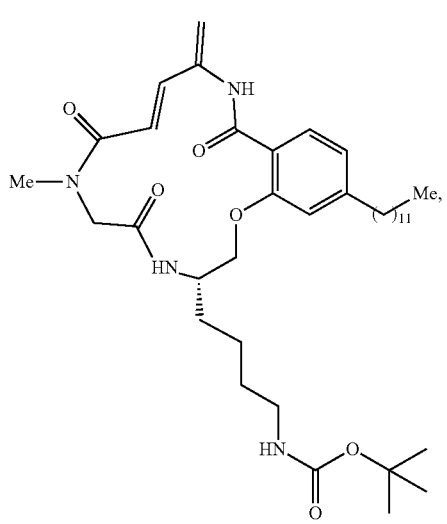
-continued
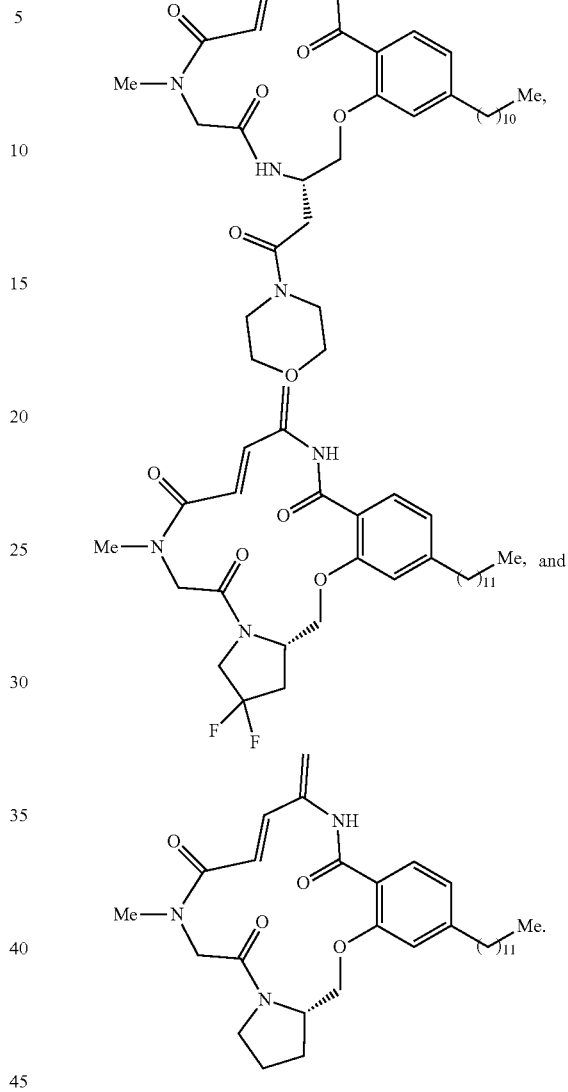
16. The compound according to claim 1, wherein the compound is represented by formula (3):
(3)
wherein,
t is an integer between 1 and 15.
17. A pharmaceutical composition comprising the compound according to claim 1, or a pharmaceutically acceptable salt thereof and/or wherein the pharmaceutical composition further comprises a pharmaceutically acceptable carrier, diluent, excipient and/or adjuvant and/or wherein the pharmaceutical composition further comprises one or more additional therapeutic agents.

18. A method of depleting hypoxic cells in a subject that has a cancer comprising administering the compound according to claim 1 or a pharmaceutically acceptable salt thereof or a pharmaceutical composition comprising the compound according to claim 1 or a pharmaceutically acceptable salt thereof to the subject that has a cancer.

19. The method of depleting hypoxic cells in a subject that has a cancer according to claim 18, wherein the compound or the pharmaceutically acceptable salt thereof or the pharmaceutical composition selectively kills hypoxic cancer cells.

20. The method of depleting hypoxic cells in a subject that has a cancer according to claim 18, wherein the cancer is selected from the group consisting of leukemia, bladder cancer, bone and soft tissue cancer, bone cancer, ocular cancer, fallopian tube cancer, gastric cancer, head and neck cancer, kidney cancer, liver cancer, central nervous system cancer, thyroid cancer, uterus cancer, vulvar cancer, vaginal cancer, prostate cancer, colon cancer, breast cancer, lung cancer, oral cancer, pancreatic cancer, and ovarian cancer.

* * * * *